US010436630B2

(12) United States Patent
Kovacs et al.

(10) Patent No.: US 10,436,630 B2
(45) Date of Patent: Oct. 8, 2019

(54) SCALE-BASED USER-PHYSIOLOGICAL DATA HIERARCHY SERVICE APPARATUSES AND METHODS

(71) Applicant: Physiowave, Inc., Santa Clara, CA (US)

(72) Inventors: Gregory T. Kovacs, Palo Alto, CA (US); Richard M. Wiard, Campbell, CA (US)

(73) Assignee: Physiowave, Inc., Menlo Park, CA (US)

( * ) Notice: Subject to any disclaimer, the term of this patent is extended or adjusted under 35 U.S.C. 154(b) by 189 days.

(21) Appl. No.: 15/354,953

(22) Filed: Nov. 17, 2016

(65) Prior Publication Data

US 2017/0146388 A1 May 25, 2017

Related U.S. Application Data

(63) Continuation of application No. PCT/US2016/062484, filed on Nov. 17, 2016, and a continuation of application No. PCT/US2016/062505, filed on Nov. 17, 2016.

(60) Provisional application No. 62/258,238, filed on Nov. 20, 2015, provisional application No. 62/266,403, filed on Dec. 11, 2015, provisional application No. 62/266,523, filed on Dec. 11, 2015.

(51) Int. Cl.
*G01G 19/50* (2006.01)
*A61B 5/00* (2006.01)

(52) U.S. Cl.
CPC .......... *G01G 19/50* (2013.01); *A61B 5/0002* (2013.01); *A61B 5/0006* (2013.01)

(58) Field of Classification Search
CPC ...... G01G 19/50; A61B 5/0002; A61B 5/0006
See application file for complete search history.

(56) References Cited

U.S. PATENT DOCUMENTS

| | | |
|---|---|---|
| 3,702,113 A | 11/1972 | Blockley et al. |
| 4,195,643 A | 4/1980 | Pratt, Jr. |
| 4,362,164 A | 12/1982 | Little et al. |
| 4,557,271 A | 12/1985 | Stoller et al. |
| 4,657,025 A | 4/1987 | Orlando |
| 4,679,569 A | 7/1987 | Lee |
| 4,765,321 A | 8/1988 | Mohri |
| 4,836,215 A | 6/1989 | Lee |

(Continued)

*Primary Examiner* — Randy W Gibson
(74) *Attorney, Agent, or Firm* — Crawford Maunu PLLC

(57) ABSTRACT

Certain aspects of the disclosure are directed to an apparatus including a weighing scale and external circuitry. The weighing scale includes a platform including force sensor circuitry and a plurality of electrodes to collect signals indicative of the user's identity and cardio-related physiologic data while the user is standing on the platform and processing circuitry. The processing circuitry configured with the force sensor circuitry and the plurality of electrodes to collect the cardio-related physiologic data from the user and output at least portions of the cardio-related physiologic data as user data. The external circuitry receives user data from a plurality of weighing scales include the weighing scale and provides a hierarchy of services using scale-obtained data, wherein the hierarchy of services include different services enabled in response to user selection of the service and activation of subscription levels of different weighted values.

16 Claims, 33 Drawing Sheets

(56) References Cited

U.S. PATENT DOCUMENTS

| | | | |
|---|---|---|---|
| 4,898,182 A | 2/1990 | Hawkins et al. | |
| 4,947,857 A | 8/1990 | Albert et al. | |
| 4,958,638 A | 9/1990 | Sharpe et al. | |
| 5,314,389 A | 5/1994 | Dotan | |
| 5,431,170 A | 7/1995 | Mathews | |
| 5,620,003 A | 4/1997 | Sepponen | |
| 5,678,562 A | 10/1997 | Sellers | |
| 5,682,902 A | 11/1997 | Herleikson | |
| 5,701,894 A | 12/1997 | Cherry et al. | |
| 5,750,937 A | 5/1998 | Johnson et al. | |
| 5,782,238 A | 7/1998 | Beitler | |
| 5,833,623 A | 11/1998 | Mann et al. | |
| 6,047,203 A | 4/2000 | Sackner et al. | |
| 6,080,110 A | 6/2000 | Thorgersen | |
| 6,168,563 B1 | 1/2001 | Brown | |
| 6,198,394 B1 | 3/2001 | Jacobsen et al. | |
| 6,205,547 B1 | 3/2001 | Davis | |
| 6,228,033 B1 | 5/2001 | Koobi et al. | |
| 6,256,532 B1* | 7/2001 | Cha | A61B 5/0537 177/245 |
| 6,292,690 B1 | 9/2001 | Petrucelli | |
| 6,331,162 B1 | 12/2001 | Mitchell | |
| 6,402,699 B1* | 6/2002 | Kodama | A61B 5/0537 600/551 |
| 6,403,897 B1* | 6/2002 | Bluth | A61B 5/0002 128/920 |
| 6,454,708 B1 | 9/2002 | Ferguson et al. | |
| 6,454,719 B1 | 9/2002 | Greenhut | |
| 6,496,842 B1* | 12/2002 | Lyness | G06F 3/0482 707/E17.012 |
| 6,516,221 B1 | 2/2003 | Hirouchi et al. | |
| 6,551,252 B2 | 4/2003 | Sackner et al. | |
| 6,594,759 B1 | 7/2003 | Wang | |
| 6,640,134 B2 | 10/2003 | Raymond et al. | |
| 6,685,634 B1 | 2/2004 | Fry | |
| 6,702,754 B2 | 3/2004 | Ogura et al. | |
| 6,705,990 B1* | 3/2004 | Gallant | A61B 5/0205 128/903 |
| 6,734,856 B2 | 5/2004 | Ishikawa et al. | |
| 6,755,783 B2 | 6/2004 | Cosentino et al. | |
| 6,781,067 B2* | 8/2004 | Montagnino | G01G 19/44 177/142 |
| 6,783,498 B2 | 8/2004 | Sackner et al. | |
| 6,790,178 B1 | 9/2004 | Mault et al. | |
| 6,814,705 B2 | 11/2004 | Kawaguchi | |
| 6,847,892 B2 | 1/2005 | Zhou et al. | |
| 6,875,174 B2 | 4/2005 | Braun et al. | |
| 6,898,299 B1 | 5/2005 | Brooks | |
| 6,962,566 B2 | 11/2005 | Quistgaard et al. | |
| 6,963,035 B2 | 11/2005 | Honda et al. | |
| 6,974,075 B1* | 12/2005 | Duke | A61B 5/02405 235/375 |
| 7,137,955 B2 | 11/2006 | Bartels et al. | |
| 7,257,438 B2 | 8/2007 | Kinast | |
| 7,313,435 B2 | 12/2007 | Nakada et al. | |
| 7,316,648 B2 | 1/2008 | Kelly et al. | |
| 7,336,266 B2 | 2/2008 | Hayward et al. | |
| 7,382,247 B2 | 6/2008 | Welch et al. | |
| 7,384,410 B2 | 6/2008 | Eggers et al. | |
| 7,417,536 B2 | 8/2008 | Lakshmanan et al. | |
| 7,459,644 B2 | 12/2008 | Kenmochi | |
| 7,502,643 B2 | 3/2009 | Farringdon et al. | |
| 7,593,632 B2 | 9/2009 | Schnell | |
| 7,668,588 B2 | 2/2010 | Kovacs | |
| 7,787,946 B2 | 8/2010 | Stahmann et al. | |
| 7,796,013 B2 | 9/2010 | Murakami et al. | |
| 7,846,104 B2 | 12/2010 | MacQuarrie et al. | |
| 7,899,522 B1 | 3/2011 | Koh et al. | |
| 8,200,320 B2 | 6/2012 | Kovacs | |
| 8,200,453 B2* | 6/2012 | Gage | G06F 19/00 702/173 |
| 8,332,026 B2 | 12/2012 | Cha et al. | |
| 8,369,936 B2 | 2/2013 | Farringdon et al. | |
| 8,452,390 B2 | 5/2013 | Jensen | |
| 8,473,041 B2 | 6/2013 | Bartnik et al. | |
| 8,475,367 B1* | 7/2013 | Yuen | G06F 19/3418 600/300 |
| 8,475,368 B2 | 7/2013 | Tran et al. | |
| 8,529,409 B1 | 9/2013 | Lesea-Ames | |
| 8,548,556 B2 | 10/2013 | Jensen | |
| 8,639,226 B2 | 1/2014 | Hutchings et al. | |
| 8,682,424 B2 | 3/2014 | Tsoglin et al. | |
| 8,698,014 B1 | 4/2014 | Walstad | |
| 8,704,110 B2* | 4/2014 | Forshaw | G01G 19/44 177/238 |
| 8,858,449 B2 | 10/2014 | Inan et al. | |
| 8,870,780 B2 | 10/2014 | Inan et al. | |
| 9,011,346 B2 | 4/2015 | Wiard et al. | |
| 9,055,871 B2 | 6/2015 | Inan et al. | |
| 9,215,991 B2 | 12/2015 | Inan et al. | |
| 9,241,637 B2 | 1/2016 | Wiard et al. | |
| 9,770,206 B2* | 9/2017 | Ashokan | A61B 5/4872 |
| 9,778,095 B2* | 10/2017 | Carreel | G01G 19/50 |
| 9,891,095 B2* | 2/2018 | Villard | G01G 19/4146 |
| 2001/0030546 A1 | 10/2001 | Yamada et al. | |
| 2001/0044588 A1 | 11/2001 | Mault | |
| 2002/0002326 A1 | 1/2002 | Causey, III et al. | |
| 2002/0062090 A1 | 5/2002 | Chai et al. | |
| 2002/0188205 A1 | 12/2002 | Mills | |
| 2003/0050537 A1 | 3/2003 | Wessel | |
| 2003/0088196 A1 | 5/2003 | Steve | |
| 2003/0126593 A1 | 7/2003 | Mault | |
| 2003/0130567 A1 | 7/2003 | Mault et al. | |
| 2003/0130595 A1 | 7/2003 | Mault | |
| 2003/0149349 A1 | 8/2003 | Jensen | |
| 2003/0197614 A1 | 10/2003 | Smith et al. | |
| 2003/0233034 A1 | 12/2003 | Varri et al. | |
| 2004/0068379 A1 | 4/2004 | Morgan et al. | |
| 2004/0073127 A1 | 4/2004 | Istvan et al. | |
| 2004/0097802 A1 | 5/2004 | Cohen | |
| 2004/0138517 A1 | 7/2004 | Osorio et al. | |
| 2004/0211599 A1 | 10/2004 | Kasinoff | |
| 2004/0238228 A1* | 12/2004 | Montague | G01G 19/44 177/25.13 |
| 2004/0249258 A1 | 12/2004 | Tupin, Jr. et al. | |
| 2005/0004483 A1 | 1/2005 | Lin | |
| 2005/0017602 A1 | 1/2005 | Arms et al. | |
| 2005/0033124 A1 | 2/2005 | Kelly et al. | |
| 2005/0043645 A1 | 2/2005 | Ono et al. | |
| 2005/0113703 A1 | 5/2005 | Farringdon et al. | |
| 2005/0119711 A1 | 6/2005 | Cho et al. | |
| 2005/0171451 A1 | 8/2005 | Yeo et al. | |
| 2005/0203349 A1 | 9/2005 | Nanikashvili | |
| 2005/0206518 A1 | 9/2005 | Welch et al. | |
| 2005/0215868 A1 | 9/2005 | Kenjou et al. | |
| 2005/0247494 A1 | 11/2005 | Montagnino | |
| 2005/0283198 A1 | 12/2005 | Haubrich et al. | |
| 2006/0049955 A1 | 3/2006 | Blum et al. | |
| 2006/0079942 A1 | 4/2006 | Deno et al. | |
| 2006/0106646 A1 | 5/2006 | Squilla et al. | |
| 2006/0111641 A1 | 5/2006 | Manera et al. | |
| 2006/0116589 A1 | 6/2006 | Park | |
| 2006/0122525 A1 | 6/2006 | Shusterman | |
| 2006/0149139 A1 | 7/2006 | Bonmassar et al. | |
| 2006/0154642 A1 | 7/2006 | Scannell | |
| 2006/0155589 A1 | 7/2006 | Lane et al. | |
| 2006/0161478 A1* | 7/2006 | Turner | G06Q 30/02 705/14.17 |
| 2007/0055324 A1 | 3/2007 | Thompson et al. | |
| 2007/0069887 A1 | 3/2007 | Welch et al. | |
| 2007/0161913 A1 | 7/2007 | Farrell et al. | |
| 2007/0167286 A1 | 7/2007 | Roes | |
| 2007/0197878 A1 | 8/2007 | Shklarski | |
| 2007/0208232 A1 | 9/2007 | Kovacs | |
| 2007/0208233 A1 | 9/2007 | Kovacs | |
| 2007/0287928 A1 | 12/2007 | Kiviniemi et al. | |
| 2007/0293770 A1 | 12/2007 | Bour et al. | |
| 2008/0027679 A1 | 1/2008 | Shklarski | |
| 2008/0073128 A1 | 3/2008 | Umemoto | |
| 2008/0154645 A1 | 6/2008 | Takehara | |
| 2008/0161700 A1 | 7/2008 | Sachanandani et al. | |
| 2008/0183090 A1 | 7/2008 | Farringdon et al. | |
| 2008/0194975 A1 | 8/2008 | MacQuarrie et al. | |

(56) References Cited

U.S. PATENT DOCUMENTS

| | | |
|---|---|---|
| 2008/0208009 A1 | 8/2008 | Shklarski |
| 2008/0221404 A1 | 9/2008 | Tso |
| 2008/0246629 A1 | 10/2008 | Tsui et al. |
| 2008/0281222 A1 | 11/2008 | Fukada |
| 2008/0306393 A1 | 12/2008 | Ting et al. |
| 2009/0016582 A1 | 1/2009 | Penn et al. |
| 2009/0024044 A1 | 1/2009 | Virtanen et al. |
| 2009/0102296 A1 | 4/2009 | Greene et al. |
| 2009/0118589 A1 * | 5/2009 | Ueshima ............... A61B 5/0002 600/300 |
| 2009/0182204 A1 | 7/2009 | Semler et al. |
| 2009/0203972 A1 | 8/2009 | Heneghan et al. |
| 2009/0240194 A1 | 9/2009 | Keimel et al. |
| 2009/0284496 A1 | 11/2009 | Oki |
| 2009/0287933 A1 | 11/2009 | Beckwith et al. |
| 2009/0315733 A1 | 12/2009 | Bischoff |
| 2010/0004715 A1 | 1/2010 | Fahey |
| 2010/0016685 A1 | 1/2010 | Muehlsteff et al. |
| 2010/0094147 A1 * | 4/2010 | Inan ..................... A61B 5/7207 600/500 |
| 2010/0174205 A1 | 7/2010 | Wegerif |
| 2010/0210921 A1 | 8/2010 | Park et al. |
| 2010/0262044 A1 | 10/2010 | Siegler |
| 2011/0040352 A1 | 2/2011 | Gerber et al. |
| 2011/0054359 A1 | 3/2011 | Sazonov et al. |
| 2011/0080181 A1 | 4/2011 | Sato et al. |
| 2011/0152695 A1 | 6/2011 | Granqvist et al. |
| 2011/0240379 A1 | 10/2011 | Forshaw et al. |
| 2011/0245710 A1 | 10/2011 | Jensen |
| 2011/0310005 A1 | 12/2011 | Chen |
| 2012/0003933 A1 | 1/2012 | Baker et al. |
| 2012/0065895 A1 | 3/2012 | Saul |
| 2012/0071792 A1 | 3/2012 | Pfeffer et al. |
| 2012/0123219 A1 | 5/2012 | Georgiev et al. |
| 2012/0165622 A1 | 6/2012 | Rodriguez et al. |
| 2012/0245476 A1 | 9/2012 | Skeri et al. |
| 2012/0266250 A1 | 10/2012 | Uhl |
| 2012/0283587 A1 | 11/2012 | Gosh et al. |
| 2012/0302843 A1 | 11/2012 | Otsubo et al. |
| 2012/0318869 A1 | 12/2012 | Edmonds |
| 2013/0006669 A1 | 1/2013 | Nakamura |
| 2013/0056285 A1 | 3/2013 | Meagher |
| 2013/0113506 A1 | 5/2013 | Poupyrev et al. |
| 2013/0226601 A1 | 8/2013 | Razmi et al. |
| 2013/0289889 A1 | 10/2013 | Yuen et al. |
| 2013/0310700 A1 | 11/2013 | Wiard et al. |
| 2014/0089836 A1 | 3/2014 | Damani et al. |
| 2014/0094707 A1 | 4/2014 | Farringdon et al. |
| 2014/0121540 A1 | 5/2014 | Raskin |
| 2014/0142396 A1 | 5/2014 | Ricks et al. |
| 2014/0142437 A1 | 5/2014 | Inan et al. |
| 2014/0172314 A1 | 6/2014 | Baarman et al. |
| 2014/0182952 A1 | 7/2014 | Yuen et al. |
| 2014/0221849 A1 | 8/2014 | Farringdon et al. |
| 2014/0221850 A1 | 8/2014 | Farringdon et al. |
| 2015/0107910 A1 | 4/2015 | Villard et al. |
| 2015/0112209 A1 | 4/2015 | Blaber et al. |
| 2015/0160068 A1 | 6/2015 | Carreel et al. |
| 2015/0168205 A1 | 6/2015 | Lee |
| 2015/0193497 A1 | 7/2015 | Tallamy et al. |
| 2015/0201844 A1 | 7/2015 | Nakagawa |
| 2015/0289802 A1 | 10/2015 | Thomas et al. |
| 2015/0331491 A1 | 11/2015 | Rumreich |
| 2015/0335291 A1 | 11/2015 | Saadi et al. |
| 2015/0338265 A1 | 11/2015 | Carreel et al. |
| 2016/0029905 A1 | 2/2016 | Kovacs |
| 2016/0116326 A1 | 4/2016 | Sharma |
| 2016/0317043 A1 | 11/2016 | Campo et al. |

* cited by examiner

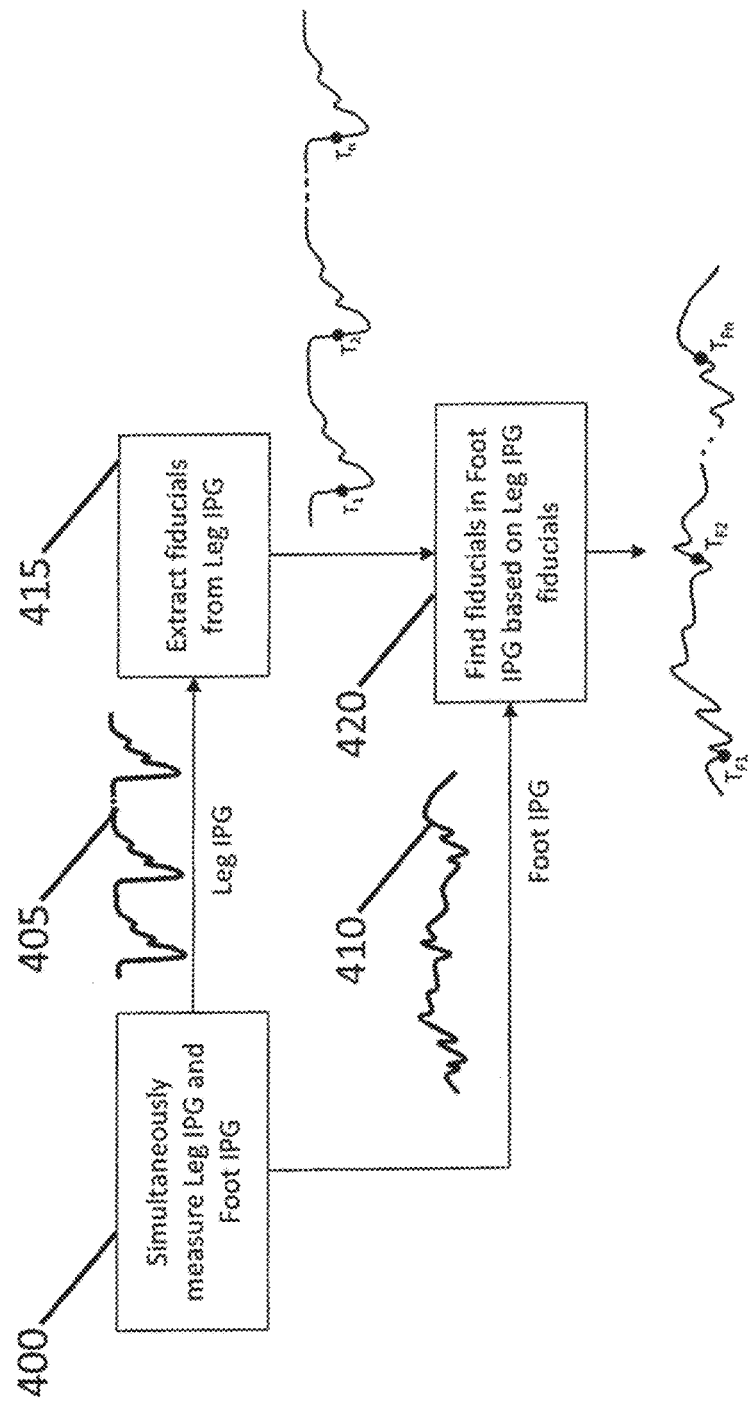

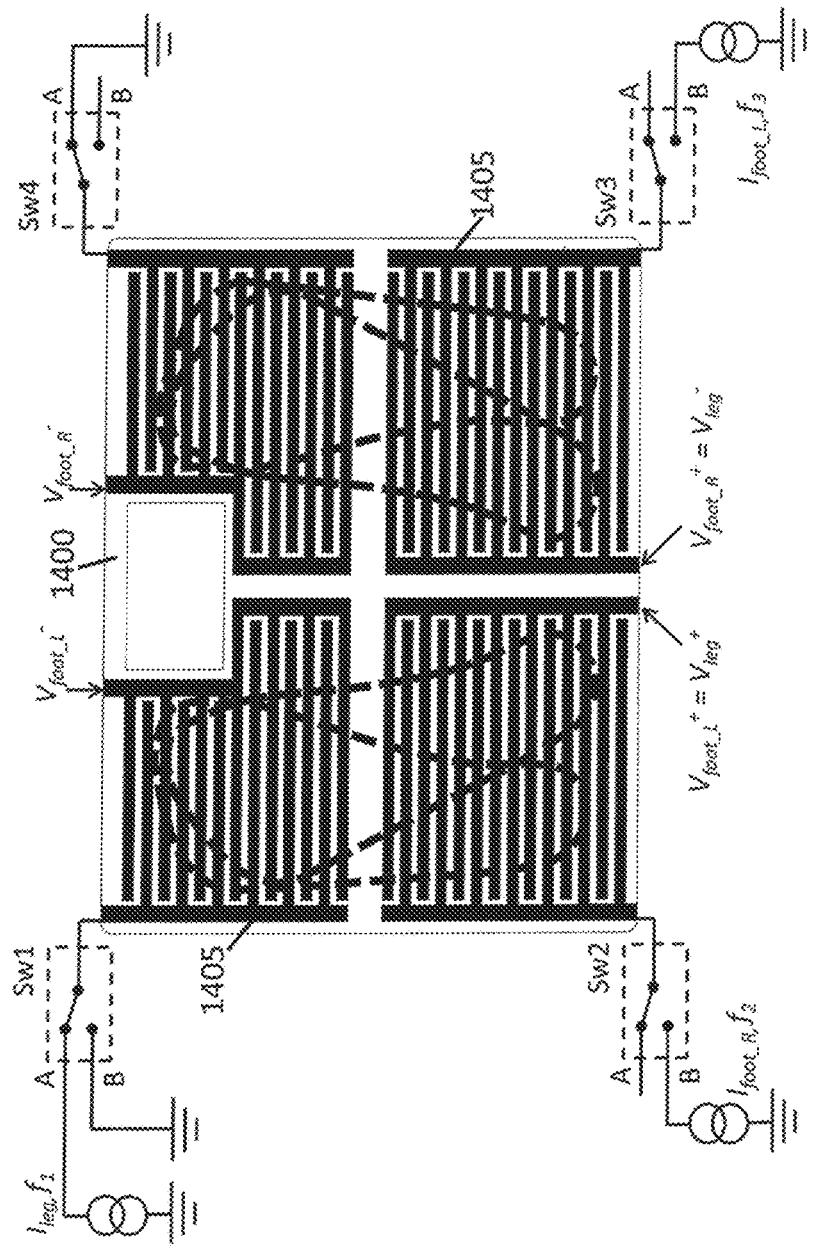

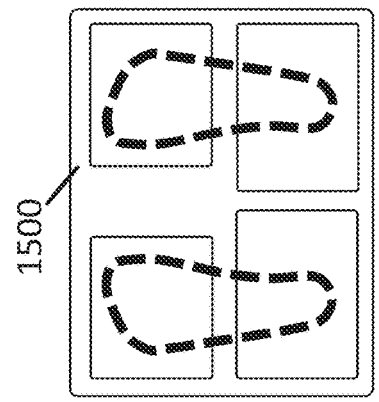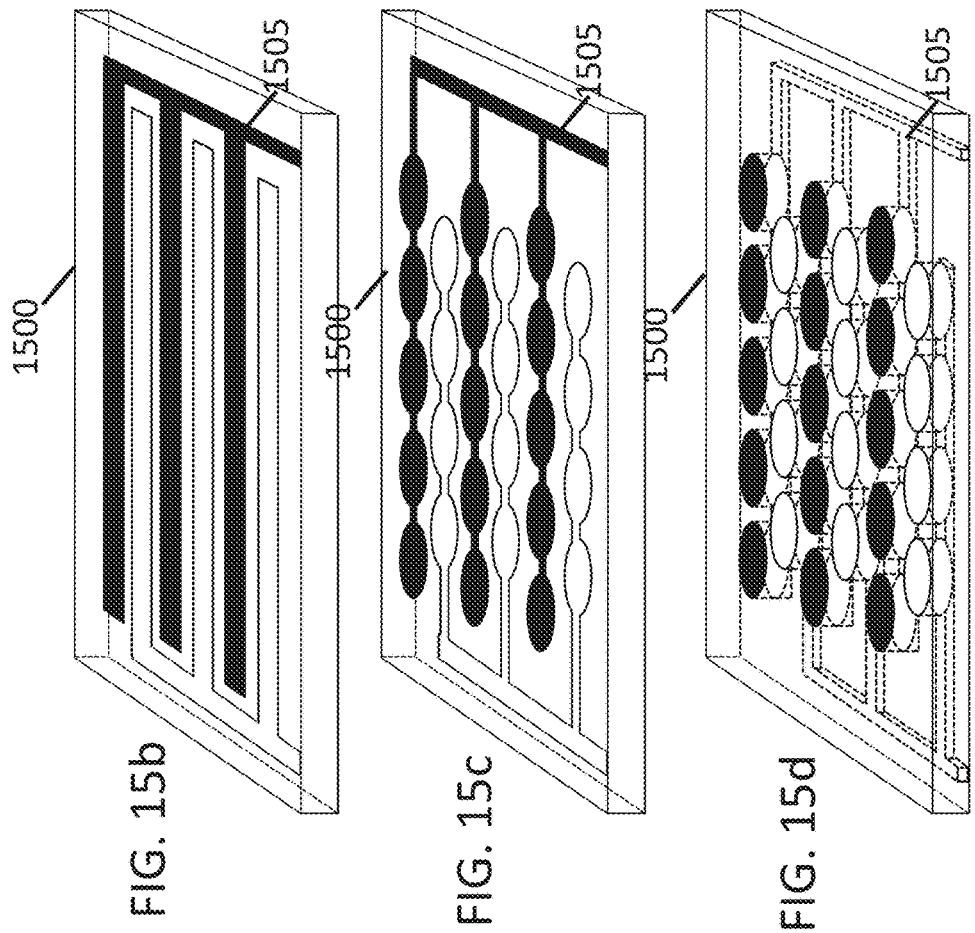

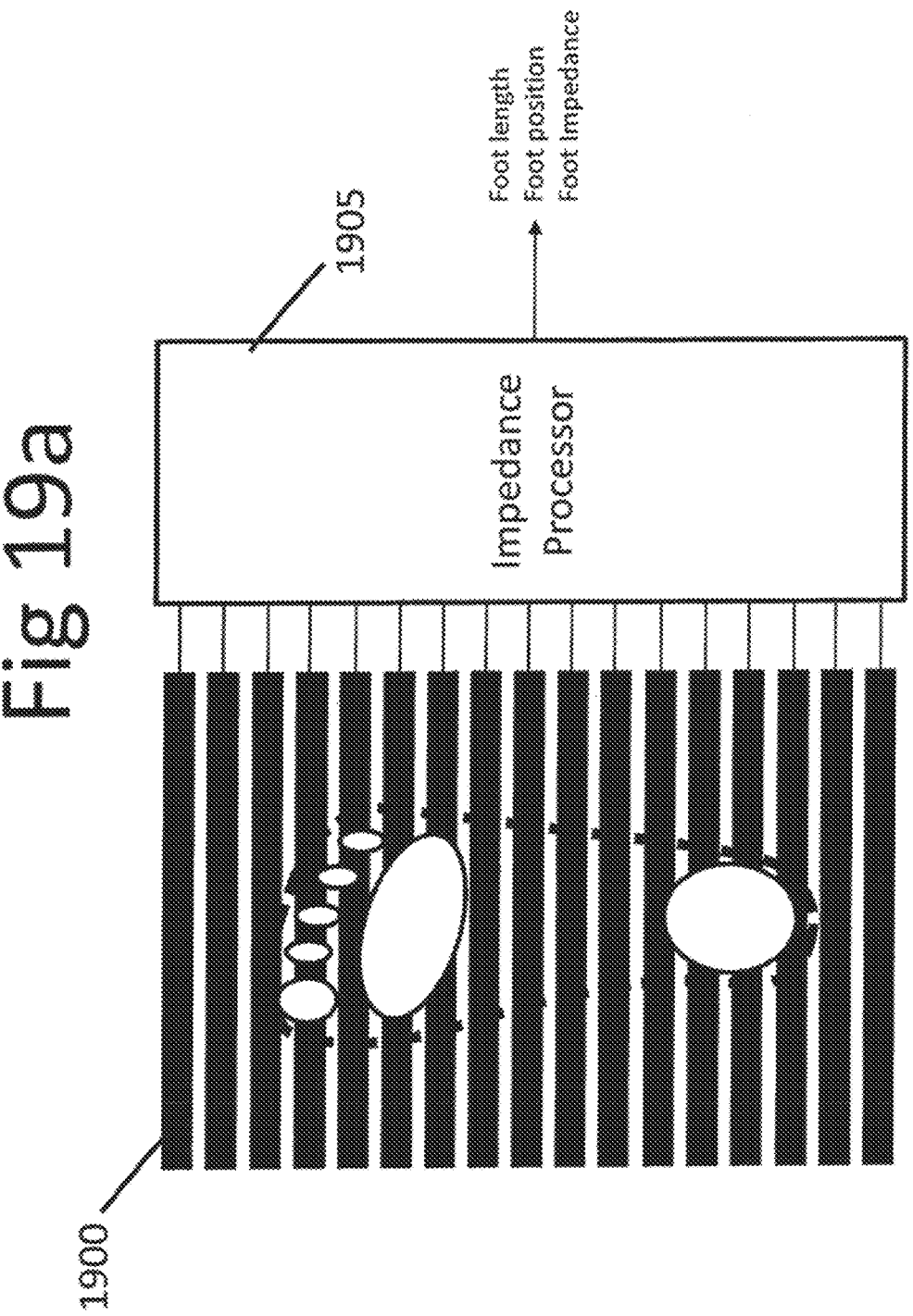

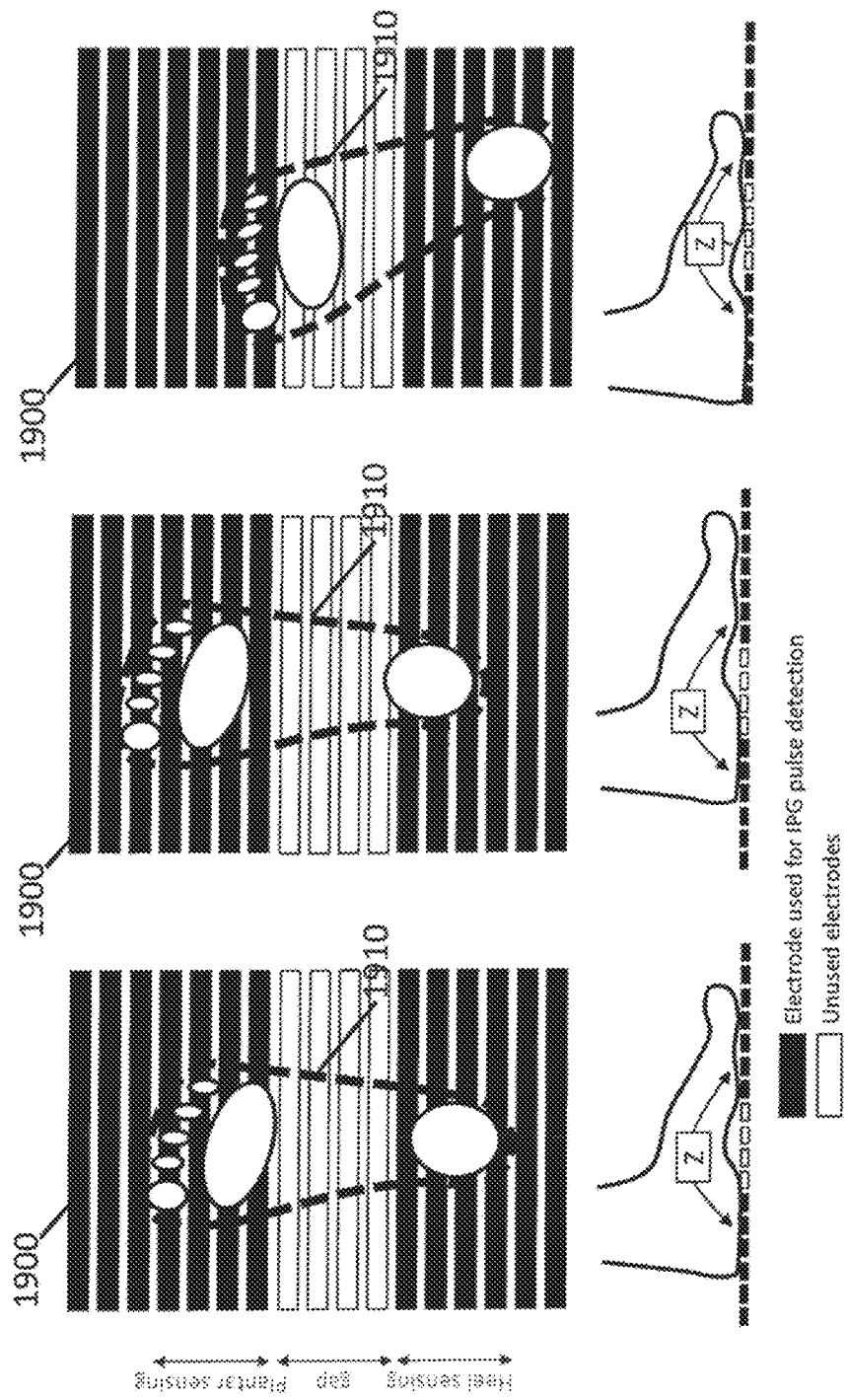

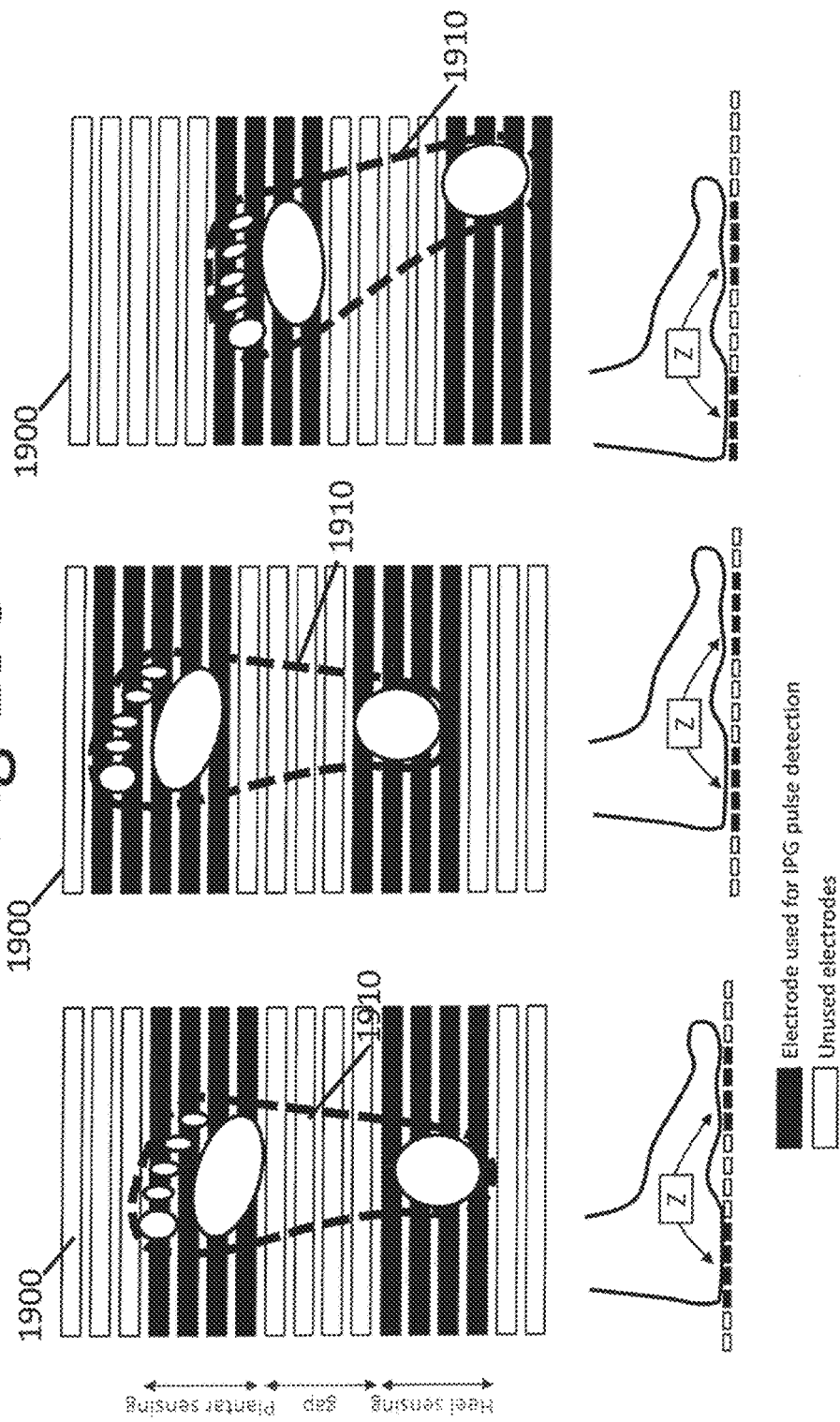

SCALE-BASED USER-PHYSIOLOGICAL DATA HIERARCHY SERVICE APPARATUSES AND METHODS

RELATED APPLICATION DATA

This application is related to PCT Application (Ser. No. PCT/US2016/062484), entitled "Scale-Based Parameter Acquisition Methods and Apparatuses", filed on Nov. 17, 2016, PCT Application (Ser. No. PCT/US2016/062505), entitled "Remote Physiologic Parameter Assessment Methods and Platform Apparatuses", filed on Nov. 17, 2016, U.S. Provisional application (Ser. No. 62/258,238), entitled "Condition or Treatment Assessment Methods and Platform Apparatuses", filed Nov. 20, 2015, U.S. Provisional application (Ser. No. 62/266,403), entitled "Scale-Based User-Physiological Data Hierarchy Service System", filed Dec. 11, 2015, and U.S. Provisional application (Ser. No. 62/266,523) entitled "Social Grouping Using a User-Specific Scale-Based Enterprise System", filed Dec. 11, 2015", which are fully incorporated herein by reference.

OVERVIEW

Various aspects of the present disclosure are directed toward methods, systems and apparatuses that are useful for providing a hierarchy of services using scale-based user physiological data.

Various aspects are directed to monitoring different physiological characteristics for many different applications. For instance, physiological monitoring instruments are often used to measure a number of patient vital signs, including blood oxygen level, body temperature, respiration rate and electrical activity for electrocardiogram (ECG) or electroencephalogram (EEG) measurements. For ECG measurements, a number of electrocardiograph leads may be connected to a patient's skin, and are used to obtain a signal from the patient. Obtaining physiological signals (e.g., data) can often require specialty equipment and intervention with medical professionals.

Databases are used for a large number of different applications. In some instances, the databases are used to store sensitive information that calls for a measure of security. Depending upon the importance of the information and the potential for misuse of the information, different levels of security are implemented. One type of information that typically requires a high level of security is health information, such as identification of user health information.

For many applications, such requirements may be costly or burdensome. These and other matters have presented challenges to monitoring physiological characteristics.

Aspects of the present disclosure are directed to a platform system, including a platform apparatus and external circuitry, which provides a hierarchy of services using scale-obtained data. The platform apparatus, such as a body weight scale, collects scale-obtained data from the user and, optionally, outputs the scale-obtained data to external circuitry, such as a standalone CPU and/or a server CPU. In specific aspects, the external circuitry includes a server CPU that pools user data from a plurality of scales and is used, in connection with the scale, to provide a hierarchy of services. A service, as used herein, includes a function and/or action performed using the platform system and uses and/or is in response to scale-obtained data. A hierarchy of services include different services enabled in response to user selection and activation of subscription levels of different weighted values. For example, the scale-obtained data from the particular scale drives a physiological related prompt for a service. The physiological related prompt is displayed on a user interface of the scale and/or is displayed on an external user interface that is in communication with the scale. The user selection of the prompt drives another physiological related prompt for a (more) specific service. The specific service has a weighted value pertaining to subscribed access for data resulting from the specific service. In further specific aspects, the service includes generic health information pertaining to the scale-obtained data, products or services correlated to the scale-obtained data, and/or additional tests to perform responsive to the scale-obtained data. The specific service, in other aspects, includes diagnosis by a physician, prescriptions, social groups based on the scale-obtained data, and/or participating in studies/experiments. The hierarchy of services is responsive to scale-obtained data and user selection of previous services. In other specific aspects, the different services include different levels of social groupings, such as a general consumer level, a physiological scale-based level, and a professional physiological level.

In certain aspects, the present disclosure is directed to apparatuses and methods including a scale and external circuitry. The scale is configured to collect signals from a plurality of users and associate the respective collected signals with a user among the plurality using a scale-based biometric. The scale includes a user display to display data to a user while the user is standing on the scale, a platform for a user to stand on, and processing circuitry. The scale further can include data-procurement circuitry that includes force sensor circuitry and a plurality of electrodes integrated with the platform for engaging the user with electrical signals and collecting signals indicative of the user's identity and cardio-physiological measurements while the user is standing on the platform. The processing circuitry includes a CPU and a memory circuit with user corresponding data stored in the memory circuit. The processing circuitry is arranged with (e.g., electrically integrated with or otherwise in communication) with the force sensor circuitry and the plurality of electrodes and configured to process data obtained by the data-procurement circuitry while the user is standing on the platform and therefrom generate cardio-related physiologic data corresponding to the collected signals. For example, the processing circuitry collects cardio-related physiologic data from the user while the user is standing on the platform, output at least portions of the cardio-related physiologic data as user data, and provides a hierarchy of services using scale-obtained data. The hierarchy of services include different services enabled in response to user selection of one or more of the different services and activation of subscription levels of different weighted values As a specific example, a user stands on a platform apparatus. The platform apparatus collects scale-obtained data and outputs the scale-obtained data to a server central processing unit (CPU). The server CPU processes the scale-obtained data and identifies that the user is at risk for atrial fibrillation based on demographic information and cardiac-information of the user and various reference health information accessible by the server CPU. The server CPU derives generic health information related to atrial fibrillation and outputs the generic health information to the scale. The scale receives the generic health information correlated to atrial fibrillation, and in response, displays a notification using the user interface of the scale that indicates additional health information is available. The notification asks the user if the user is interested in viewing the information. The information, in specific aspects, is correlated to a zero level subscription, such that all users with scales are able to obtain such information. The user provides a user input to the user interface indicating an interest in viewing the information, such as on the user's smartphone. In response to the user input, the scale displays another notification asking if the user is interested in their scale-obtained data being viewed by a physician for diagnosis purposes and indicating that such a service is associated with a first level subscription correlated with a weighted factor (e.g., monthly subscription). In response to a user input indicating the user is interested in the diagnostic service and enabling the first level subscription, a physician views the user data by accessing the pooled user data and/or the scale outputs the data directly to the physician. In response to the physician diagnosing the user with atrial fibrillation, the scale displays notifications of various advertisements that correlate to atrial fibrillation such as prescriptions and/or exercise programs. If the user selects the advertisement, the provider of the system, in some aspects, is provided a return by the advertiser. Further, the scale displays a notification asking if the user is interested in participating in a study that is related to atrial fibrillation. The trial, in some specific aspects, includes a program by a physician to assist with atrial fibrillation and/or a titration of a prescription drug that is offered as a second level subscription with a higher weighted factor than the first level subscription. Alternatively and/or in addition, the trial includes a study by a researcher, which may include the physician that is offered as a third level subscription to the researcher. The researcher, and not the user, in such instances, is responsible for the higher weighted factor. Further, the third level subscription, in some specific aspects, provides a return to the user for their time.

In various more specific aspects, the external circuitry receives scale-obtained data from a plurality of platform apparatuses and pools the data in a database. The database of pooled user data is accessible to various sources for research, studies, education, and/or for other purposes. The external circuitry can securely pool the user data using a variety of security techniques. Each platform apparatus, such as a body weight scale, communicates secure scale-obtained data. For example, each platform apparatus collects scale-obtained data from a user while the user is standing on the platform apparatus and secures the scale-obtained data by removing portions of the scale-obtained data that identifies the user, and, in some aspects, adds a scale identifier (ID) and a user ID to the scale-obtained data. The external circuitry (and/or the scale) securely stores the scale-obtained data by replacing the scale ID and user ID with an alias ID, and storing the scale-obtained data with the alias ID in a first database and storing identification of which scale and user corresponds to the respective alias ID in a second database. The external circuitry outputs a subset of the user data with alias IDs, such as circuitry of a requester, such as to one of the plurality of scales or to a researcher as part of a hierarchy service, based on analysis parameters and security parameters. The analysis parameters include such parameters as user demographics, conditions or diseases, lifestyle and/or a pseudo-random. In some instances, the data is provided for research purposes and the analysis parameters are provided by the researchers. The security parameters include parameters that restrict the subset of data provided to reduce a likelihood of the identities of the users being compromised and/or based on security level and/or measures of the circuitry the data is being provided to.

In various aspects, the external circuitry further provides features such as revising the alias IDs each time data is requested. By providing scale-obtained data with alias IDs based on security level and/or measures of the requester of the data, the requester has a lower risk of inappropriately determining the user's identities as compared to providing the complete scale-obtained data sets for the users.

In certain embodiments, aspects as described herein are implemented in accordance with and/or in combination with aspects of the PCT Application (Ser. No. PCT/US2016/062484), entitled "Scale-Based Parameter Acquisition Methods and Apparatuses", filed on Nov. 17, 2016, PCT Application (Ser. No. PCT/US2016/062505), entitled "Remote Physiologic Parameter Assessment Methods and Platform Apparatuses", filed on Nov. 17, 2016, U.S. Provisional application (Ser. No. 62/258,238), entitled "Condition or Treatment Assessment Methods and Platform Apparatuses", filed Nov. 20, 2015, U.S. Provisional application (Ser. No. 62/266,403), entitled "Scale-Based User-Physiological Data Hierarchy Service System", filed Dec. 11, 2015, and U.S. Provisional application (Ser. No. 62/266,523) entitled "Social Grouping Using a User-Specific Scale-Based Enterprise System", filed Dec. 11, 2015", to which benefit is claimed and which are fully incorporated herein by reference.

The above discussion/summary is not intended to describe each embodiment or every implementation of the present disclosure. The figures and detailed description that follow also exemplify various embodiments.

BRIEF DESCRIPTION OF THE DRAWINGS

Various example embodiments may be more completely understood in consideration of the following detailed description in connection with the accompanying drawings, in which:

FIG. 1e shows current paths through the body for the IPG trigger pulse and Foot IPG, consistent with various aspects of the present disclosure;

FIG. 4 shows an example block diagram depicting signal processing steps to obtain fiducial references from the individual Leg IPG "beats," which are subsequently used to obtain fiducials in the Foot IPG, consistent with various aspects of the present disclosure;

FIG. 14a shows another example of a scale with interleaved foot electrodes to inject and sense current from one foot to another foot, and measure Foot IPG signals in both feet, consistent with various aspects of the present disclosure;

FIGS. 15a-d show an example breakdown of a scale with interleaved foot electrodes to inject and sense current from one foot to another foot, and within one foot, consistent with various aspects of the present disclosure;

FIGS. 19a-c show example impedance as measured through different parts of the foot based on the foot position, consistent with various aspects of the present disclosure.

Figure 1A:
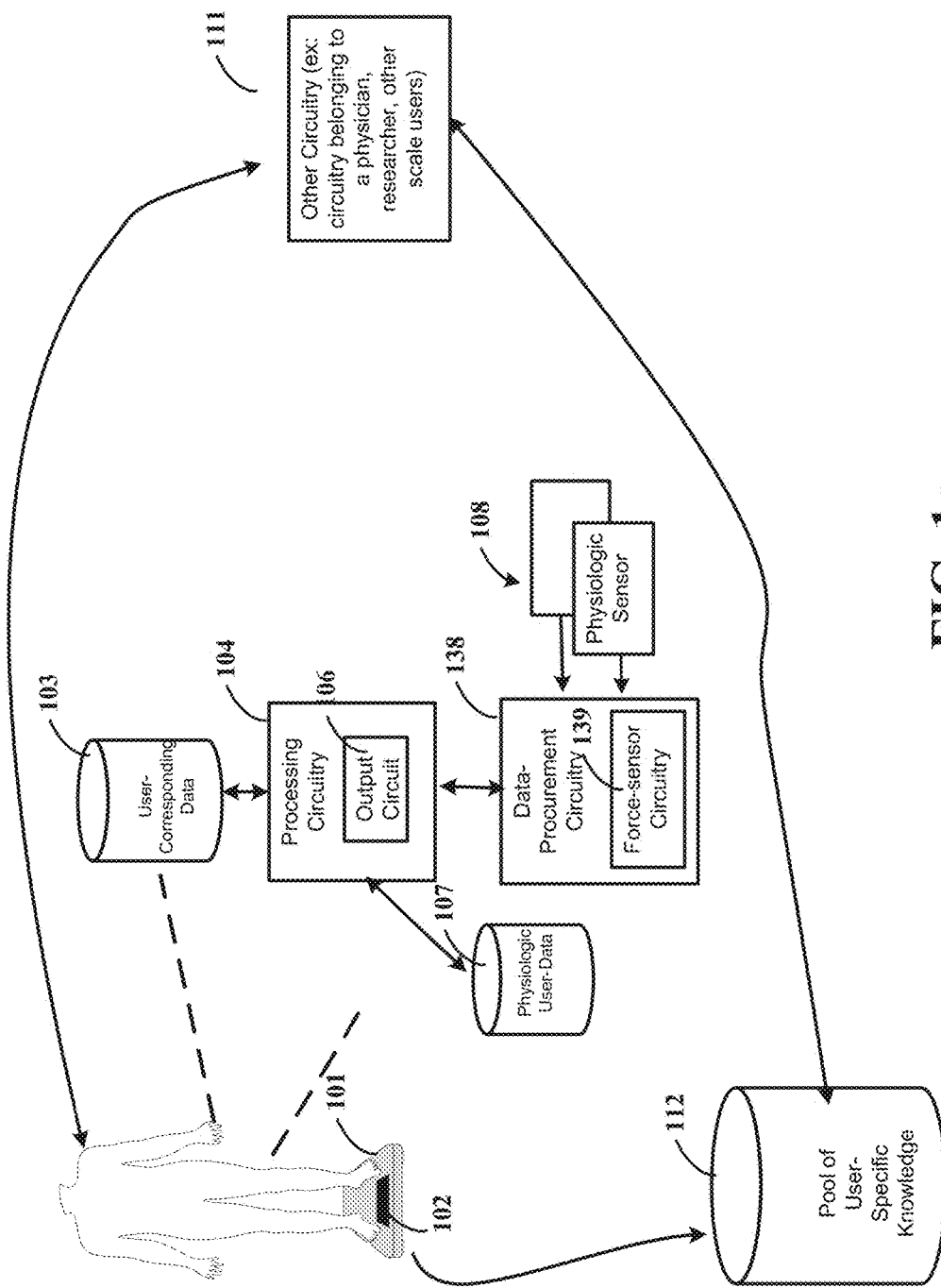
FIG. 1a shows a scale-based user-physiological heuristic system consistent with aspects of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DESCRIPTION

Aspects of the present disclosure are believed to be applicable to a variety of different types of apparatuses, systems, and methods involving providing a hierarchy of services using scale-based user physiological data and a scale-based user-physiological heuristic system. Aspects of the present disclosure have been shown to be beneficial when used in the context of a weighing scale with electrodes configured for engaging with the user and generating cardio-related physiologic data, such as data indicative of a BCG or ECG of a user. In some specific embodiments, a plurality of scales output scale-obtained user data to external circuitry, such as a server CPU, which pools the user data and is used to provide a hierarchy of services. The hierarchy of services are enabled in response to user selection of prompts and activation of different subscription levels of different weighted values. In various specific embodiments, the external circuitry identifies various risks that the user has a condition using the scale-obtained data and outputs a prompt to the scale which identifies that generic health information related to the risks is available. In response to the user selecting the prompt as displayed on the scale and/or another user device, the generic health information is provided to the user and the scale displays another prompt which identifies that a specific service is available to the user that has a weighted value pertaining to the subscription level of the specific service. In a number of specific embodiments, the user is prompted through the hierarchy until the user does not select a prompt and/or activate the subscription level. These and other aspects can be implemented to address challenges, including those discussed in the background above. While not necessarily so limited, various aspects may be appreciated through a discussion of examples using such exemplary contexts.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element. Also, although aspects and features may in some cases be described in individual figures, it will be appreciated that features from one figure or embodiment can be combined with features of another figure or embodiment even though the combination is not explicitly shown or explicitly described as a combination.

Various embodiments of the present disclosure are directed to providing a hierarchy of services using scale-based user data. The scale, in various embodiments, collects various data indicative of cardio-related information of the user and communicates data to an external circuitry. The external circuitry, such as a server CPU, receives user data from a plurality of scales and pools the user data to provide various services to the users and/or to other personnel. The user data is compared to other user data and/or various reference health information to determine correlations for the users. The correlations, in some embodiments, include potential risks for conditions, such as disorders or diseases, and/or social groupings of users with similar patterns of user data (e.g., demographic, conditions, scale-obtained data, user goals and/or lifestyle). A service, as used herein, includes a function and/or action performed using scale-obtained data. A hierarchy of services includes different services enabled in response to user selection and activation of subscription levels. The subscription levels have different weighted values that activate the subscription level. Further, each subscription level is associated with one or more services.

As a specific example, a system includes three subscription levels. The first subscription level does not have a weighted value (e.g., weighted value is zero), the second subscription level has a first weighted value, and the third subscription level has a second weighted value, which is greater than the first weighted value. The first subscription level is provided to any user with a scale. The user stands on the scale, the scale collects user data, and the scale prompts the user to access a first service of the first subscription level. As an example, the first service includes providing the user with generic health information that is tailored based on the scale-obtained data, such as cardio-data, user goals, diagnosis/health history, demographic information, among other data. The user selects the prompt, using the user interface of the scale and/or another user interface, and is provided the first service. In response to the providing the user with the first service, the scale and/or other user display, provides another prompt for a second service of the second subscription level. As an example, the second service includes providing the user access to a social grouping of users with similar physiological data. In response to the user selecting the prompt and activating the second service level based on the first weighted value, the user is provided with the second service. Further, the scale and/or other user display, provides an additional prompt for a third service of a third subscription level. In response to the user selecting the additional prompt and activating the third service level based on the second weighted value, the user is provided with the third service, such as providing the user data to a physician for diagnosis purposes.

In response to the user not selecting a prompt and/or not activating one of the service levels, the scale, in some embodiments, provides a prompt for a service of a service level that is activated for the specific users. For example, various other services includes advertisements for products and/or services, physician-provided advice over a longer period of time, participation in a study and/or experiment, social groupings based on professional (e.g., physician lead and/or participation by physician in the social grouping), among other services.

The weighted values of the subscription levels, in some embodiments, is based on the value of the service or corresponding data to the user, the sensitivity of the user data (e.g., user-sensitive data) and/or regulation of the corresponding data, the value of the corresponding data to the service provider/provider of the scales, and the value of the corresponding data to the requester. In various embodiments, the value of the service and/or corresponding data is determined based on a level of security of the data, a level of technical detail of the data, and/or a likelihood of diagnosing the user based on the data. The requester of the data provided by the service, in various embodiments, includes a third party, such as a researcher, physician, government entity, and/or other entity. The different subscription levels have different weighted values that, in some embodiments, increase with the levels of subscription. Alternatively and/or in addition, the weighted values are provided to activate the different levels by different parties. For example, in some embodiments, one or more of the subscription levels are activated by the user selecting the prompt and a third party providing the weighted value, such as a researcher. As another specific example, a gym may offer gym subscriptions whose cost decreases as fitness of the user increases, which is determined using scale-obtained data. The cost maybe offset by insurance companies (e.g., health insurance) which offer contributions to a gym subscription if the user goes a threshold number of times in a month and/or based on other health factors.

In various specific embodiments, the hierarchy of services includes providing a subset of the (securely) pooled user data to a requester, such as a physician and/or other researcher, and/or using the scales to participate in a study and/or experiment. Further, in related embodiments, to secure the user data and prevent identification of particular users, the external circuitry stores user data with an alias ID that replaces code that uniquely identifies the respective users and the respective scales. The subset of user data provided to a requester is provided, in various embodiments, based on analysis parameters and security parameters. The analysis parameters are input by the requester for the data, and include parameters such as demographics of users, conditions or diseases, parameter values, lifestyle, and/or pseudo-random selection. The security parameters include restrictions on the user data output to protect the identity of the users and the user data, which include sensitive data.

Embodiments of the present disclosure are directed to securely pooling user data from scales. The pooled data is securely and anonymously communicated to requestors based on analysis parameters and security parameters. The security and anonymity is accomplished in various embodiments by replacing an identifier that indicates an identity of the scale and the user with an alias ID and restricting access to specific data. Scales, in various embodiments, communicate with external circuitry for various processing of user data. The external circuitry securely pools user data and identifies potential correlations or patterns of risks for conditions or diseases of users. The user data, however, includes various user-sensitive data and/or data that is subject to various government regulations, such as Food and Drug Administration (FDA) regulation and HIPA disclosure requirements. To securely communicate the data, the scale removes portions of the scale-obtained data that identifies the user and adds an identifier to the scale-obtained data to identify that the user-data corresponds to one user. The scale, optionally, secures the user data by encrypting all and/or portions of the user data, such as the identifier. The scale outputs the secure data to the external circuitry. Alternatively and/or in addition, the identifier is encrypted that identifies the user and the scale, and the external circuitry replaces the identifier with an alias ID. The external circuitry stores the user data with the alias ID in a first database and stores the identification of the scale and user that corresponds to the alias ID in a second database. In this manner, the user data stored in the first database does not identify the user. Further, by storing the user data in a separate database from the identification of the alias ID and scale/user, preferably at a separate location, the pooled user data has a lower risk of being inappropriately accessed such that an external entity and/or source, such as a security hacker, identifies the respective user corresponding to the user data. Thereby, the user data is more secure and the user's identity remains unknown.

The (securely) pooled user data is used for various analytics. For example, various sources/entities request access to the user data. In some instances, the requester for the securely pooled user data includes a researcher intending to perform research on the user data. Example sources/entities include government entities for research or census studies, environment groups, scientific research groups, including both private, academic, and public source, among other entities. The research is performed on existing user data and/or the requester requests for specific data that is consequently obtained. For example, in response to analytics performed and/or prior to, the researcher requests that the external circuitry contact particular users to perform an experiment. Various users are contacted based on the analysis parameters (e.g., the parameters of the research) such as user demographic information, parameter values, and/or lifestyle indicators. The users are contacted through the user display of the scale and asked if they are interested in participating in a statistic study, an experimental study, and/or an observation study. In some embodiments, a portion of the users are used as a control group and the remaining portion as an experimental group. The scale, in some embodiments, is used to perform the study and/or encourage the user to actively participate.

In other embodiments, the requester for the securely pooled user data includes a user of one of the plurality of scales. For example, the user may be interested in learning about a particular disorder. The user may know that they have a disorder/condition or have a goal or may be interested in learning more for someone they know. The user provides the various analysis parameters using their scale and/or another user device. The scale communicates with the external circuitry to authorize the communication and outputs data to the scale. The scale, in some embodiments, outputs the user data to user circuitry such that the user can more easily view the data but the communication with the external circuitry is through the scale and responsive to identification of the user.

The external circuitry identifies the various user data to output to the requester based on the analysis parameters and the security parameters. In various embodiments, the analysis parameters identify various types of user data, such as demographics of users, conditions/disorders, lifestyle, user goals, etc., that the requester is interested in. In some embodiments, the analysis parameters establish various bias parameters and/or request for pseudo-random selection to provide analytics on a statistically random sample population. The analysis parameters further include sample size (e.g., number of users) and/or data of the data obtained. In other embodiments, the analysis parameters identify various parameters, conditions or goals the requester is interested in learning about and potential failures, successes, and/or correlated diagnosis. The external circuitry scans the pool of user-specific knowledge to identify various securely pooled user data related to the analysis parameters and collects the respective securely pooled user data.

Based on the security parameters, the external circuitry removes portions of the respective user data and/or does not include the portions in the collected securely pooled user data. Thereby, the security parameters restrict access to the securely pooled user data. User data sets corresponding to each user includes data that is unrelated to the analysis parameters and/or otherwise not used for the purpose of analysis as requested. Such data is not provided to the requester. In various embodiments, the security parameters include specific data that cannot be accessed by requesters, combinations of data, and/or a threshold sensitivity value of the user data. The identification is based on the risk of the data, such as location data and/or date of birth. In various aspects, the user data has a sensitivity value that identifies a security risk of the data. The sensitivity values are set by the external circuitry and/or the users of the scales. User data types with a sensitivity value above a threshold value (e.g., a threshold sensitivity value of the user data) may not be provided to requesters. Alternatively, data is provided based on a security of the requester. For example, if the requester has a high amount of security measures in place, a greater amount of data and/or data with higher sensitivity values are provided. If the requester has a low amount of security in place, a lower amount of data and/or only data with lower sensitivity values are provided. Examples of security measures in place include firewalls, encryption schemes used, access to the requesters database by external sources, authentication of people when accessing the data, such as tokens, passwords, and/or biometrics, among other security measures.

In various related embodiments, the security parameters include a set of rules restricting combinations of user data provided. For example, a particular requester is provided user data of particular combinations. The rules may include "can receive 2 out of the three: height, date of birth, and location data." The set of rules mitigates the risk of the requester being able to identify the user's identities. Further, the external circuitry, in some embodiments, changes the alias IDs each time a requester requests user data to prevent the requester from correlating a first data set with a second data set and obtaining the combination of user data that the set of rules are designed to prevent.

In a number of embodiments, the securely pooled user data includes a bias. For example, the user of the scale may include health conscious users and/or unhealthy or sick users. In some embodiments, the bias is such that the pooled user data does not represent a random sample census of user data from a population. The external circuitry, optionally, identifies what the bias is. The external circuitry provides the identified bias to the requester such that the requester can correct for the bias by adjusting the selection of user data and/or the external circuitry adjusts the selection of user data to correct for the bias.

In accordance with a number of embodiments, physiological parameter data is collected using an apparatus, such as a weighing scale or other platform that the user stands on. The user (e.g., owners of a scale or persons related to the owner, such as co-workers, friends, roommates, colleagues), may use the apparatus in the home, office, doctors office, or other such venue on a regular and frequent basis. The present disclosure is directed to a substantially-enclosed apparatus, as would be a weighing scale, wherein the apparatus includes a platform which is part of a housing or enclosure and a user display to output user-specific information for the user while the user is standing on the platform. The platform includes a surface area with electrodes that are integrated and configured and arranged for engaging a user as he or she steps onto the platform. Within the housing is processing circuitry that includes a CPU (e.g., one or more computer processor circuits) and a memory circuit with user-corresponding data stored in the memory circuit. The platform, over which the electrodes are integrated, is integrated and communicatively connected with the processing circuitry. The processing circuitry is programmed with modules as a set of integrated circuitry which is configured and arranged for automatically obtaining a plurality of measurement signals (e.g., signals indicative of cardio-physiological measurements) from the plurality of electrodes. The processing circuitry generates, from the signals, cardio-related physiologic data manifested as user data.

The scale, in various embodiments, includes output circuitry that outputs various data to external circuitry. For example, using the output circuitry, the scale outputs user data to external circuitry, such as a smartphone, a smartwatch, a tablet, an external server and/or processor, and/or other circuitry and devices. The external circuitry pools user data from a plurality of scales in a user-specific knowledge database and, in some embodiments, identifies correlations between user data and potential patterns of conditions and/or diseases of users using the user data. However, in various instances, the user data includes information that is regulated by a government agency, such as FDA and/or HIPPA, and/or is otherwise user-sensitive that the user does not want compromised, accessed by others, and/or otherwise manipulated by other people. Combining and storing the user data in a database can, for example, present security risks to the user data, such as another person identifying whom the particular users are and health information about the particular users. Embodiments in accordance with the present disclosure include securely storing user data by removing user identifying data from the user data and adding an alias ID to the user data so that all data associated with the same user is associated with the same alias ID. The external circuitry stores the user data with the alias ID in the user-specific knowledge database and identification of which scale and user corresponds to the respective alias ID in a separate database at a different locations. In various embodiments, the external circuitry changes the alias IDs for the user data in response to access of the user data, periodically, and/or in response to an event.

In various specific embodiments, user data from a plurality of different scales is combined to identify potential risks for conditions. For example, a plurality of users may use different scales and the user data is combined in a user-specific knowledge database. The external circuitry compares the user data within the user-specific knowledge database, which includes other user's user data and conditions they have, to determine various correlations and patterns. The user-specific knowledge database, in various embodiments, is dynamically updated overtime as more information is learned from different users. For example, the user-specific knowledge database stores data collected from a plurality of users. A first user is known to have a heart condition and has various parameters that are measured and that correlate to symptoms of the heart condition. A second user is not known to have the same heart condition but has similar parameter values as the first user. The external circuitry uses the information of the first user to determine or review a potential risk for the condition for the second user. Furthermore, if the second user is subsequently diagnosed with a different (or same) heart disease than the first user, the user-specific knowledge database is updated with this information. Thereby, the user-specific knowledge database is updated with potential risk factors and parameter values associated with a condition in response to additional information from users of the scales.

The external circuitry can optionally group respective sets of user data into groups. The groups are based on demographics, user goals, symptoms, physiological parameter values, diagnosis, prescription drug usage, lifestyle habits, medical history, family medical history, and a combination thereof. For example, the external circuitry groups user data based on fitness goals (current or historical). The correlation, in some instances, is provided to the user, without identifying specific other users. For example, correlation can provide information to the user indicative of how other users of a similar demographic reached their fitness goals. In other embodiments, the correlation includes users with a specific condition, disorder, and/or disease and causes of improvements or potential lack of improvement of symptoms of the condition, disorder and/or disease, such as lifestyle changes, prescription drugs, and/or change in exercise habits or geographic location. The pooled user data can be used to educate users based on other user's successes, failures, and/or general results.

In accordance with a number of embodiments, the hierarchy of services is based on a grouping of users. For example, one or more services of one or more subscription levels includes providing access to a social group of users. For example, in some embodiments, the access to a social group includes access to a forum, blog, webpage, and/or application. Alternatively and/or in addition, the access is to reports and/or dashboards of scale-obtained data from the users of the social group over a period of time, such as changes in physiological parameters and/or weights and potential causes of the changes (e.g., treatments, exercise, lifestyle changes). A social group, as used herein, includes grouping of a set of scale users based on scale-obtained data. The forum, blog, webpage, and/or application provided as the service includes automatically linking the uses of the group and providing the users access. In various embodiments, the forum, blog, webpage and/or application is automatically populated with reports of the user, such as rankings, progress of the users, new observation, and/or other information. In a number of embodiments, users in the social group remain anonymous and are identified by their alias ID and/or another ID selected by the user. In some embodiments, the social groups are intra scale or inter scale. For example, the scale is configured to collect user data for two or more users and correlate the respective data with a user profile of each respective users. The social grouping includes the users of the scale (e.g., intra scale) and/or users of other scales based on the pooled database of user data (e.g., inter scale).

In a number of specific embodiments, social groupings are provided as services in a plurality of different subscription levels. For example, in a first subscription level, a user is provided access to a social group based on exercise interest and/or goals or other general consumer related interests. The social group at the first level can include a consumer based social group. A consumer based social group includes or refers to a social group based on consumer interests and/or facts. At a second subscription level, a user is provided access to a physiological social group, which is based on scale-obtained data and/or diagnosis of the scale-obtained data by a physician. At a third subscription level, a user is provided access to a (more) professional social group. For example, a physician participated in the professional social group with other users and/or actively tracks the progress of the user. Alternatively and/or in addition, the physician uses the professional social group to perform a study and/or experiment.

In accordance with various embodiments, the user data is based on sensing, detection, and quantification of at least two simultaneously acquired impedance-based signals. The simultaneously acquired impedance-based signals are associated with quasi-periodic electro-mechanical cardiovascular functions, and simultaneous cardiovascular signals measured by the impedance sensors, due to the beating of an individual's heart, where the measured signals are used to determine at least one cardiovascular related characteristic of the user for determining the heart activity, health, or abnormality associated with the user's cardiovascular system. The sensors can be embedded in a user platform, such as a weighing scale-based platform, where the user stands stationary on the platform, with the user's feet in contact with the platform, where the impedance measurements are obtained where the user is standing with bare feet.

In certain embodiments, the plurality of impedance-measurement signals includes at least two impedance-measurement signals between the one foot and the other location. Further, in certain embodiments, a signal is obtained, based on the timing reference, which is indicative of synchronous information and that corresponds to information in a BCG. Additionally, the methods can include conveying modulated current between selected ones of the electrodes. The plurality of impedance-measurement signals may, for example, be carried out in response to current conveyed between selected ones of the electrodes. Additionally, the methods, consistent with various aspects of the present disclosure, include a step of providing an IPG measurement within the one foot. Additionally, in certain embodiments, the two electrodes contacting one foot of the user are configured in an inter-digitated pattern of positions over a base unit that contains circuitry communicatively coupled to the inter-digitated pattern. The circuitry uses the inter-digitated pattern of positions for the step of determining a plurality of pulse characteristic signals based on the plurality of impedance-measurement signals, and for providing an IPG measurement within the one foot. As discussed further herein, and further described in U.S. patent application Ser. No. 14/338, 266 filed on Oct. 7, 2015 (now U.S. Pat. No. 10,130,273), which is herein fully incorporated by reference for its specific teaching of inter-digitated pattern and general teaching of sensor circuitry, the circuitry can obtain the physiological data in a number of manners.

In medical (and security) applications, for example, the impedance measurements obtained from the plurality of integrated electrodes can then be used to provide various cardio-related information that is user-specific including, as non-limiting examples, synchronous information obtained from the user that corresponds to information in a ballisto-cardiogram (BCG) and impedance plethysmography (IPG) measurements. By ensuring that the user, for whom such data was obtained, matches other bio-metric data as obtained concurrently for the same user, medical (and security) personnel can then assess, diagnose and/or identify with high degrees of confidence and accuracy.

Turning now to the figures, FIG. 1a shows a scale-based user-physiologic heuristic system consistent with aspects of the present disclosure. The system includes one or more scales and external circuitry that pools user data from the one or more scales into a user-specific knowledge database 112. In various embodiments, the system optionally includes reference information. The scales collects user data that is indicative of cardio-related measurements and outputs the user data to external circuitry. The external circuitry includes the reference information and/or the user-specific knowledge database 112 and/or is in communication with the same. The system is used to provide a hierarchy of services to users of the scale based on scale-obtained data.

The hierarchy of services, as used herein, include different services that are enabled in response to user selection and activation of subscription levels of different weighted values. Each subscription level, in various embodiments, includes one or more services. As a specific example, a system includes five subscription levels and each subscription level includes one to ten services. Once a subscription level is activated, the user has access to each service of the particular subscription level. A service, as used herein, includes a function and/or action performed using scale-obtained data. Example services include providing generic health information (e.g., articles based on user interest and scale-obtained data, information based on risks identified, general correlation information or misdiagnosis information, and advertisements), tracking data from additional devices, performing additional tests, providing scale-obtained data to a physician for diagnosis purposes, providing physician reports based on scale-obtained data, providing access to social groups, and providing access to subsets of the user data (e.g., to other circuitry 111), among other services.

The weighted values include numerical values based on the value of the service or corresponding data to the user, the user-sensitivity and/or regulation of the corresponding data, the value of the corresponding data to the service provider/provider of the scales, value of the corresponding data to the requester. In various embodiments, the value of the service and/or corresponding data is determined based on a level of security of the data, a level of technical detail of the data, and/or a likelihood of diagnosing the user based on the data. The requester of the data provided by the service, in various embodiments, includes a third party, such as a researcher, physician, government entity, and/or other entity. The different subscription levels have different weighted values that, in some embodiments, increase with the levels of subscription. Alternatively and/or in addition, the weighted values are provided to activate the different subscription levels by different parties. For example, in some embodiments, one or more of the subscription levels are activated by the user selecting the prompt and a third party providing the weighted value, such as a researcher. The weighted values, in various embodiments, are provided by the user and/or third party periodically (e.g., monthly or yearly) to activate the subscription level.

The scale-obtained data used to provide the various services is collected by each scale of the system. Each scale of the system includes a platform 101 and a user display 102. The user, as illustrated by FIG. 1a is standing on the platform 101 of the apparatus. The scale, in various embodiments, is configured to collect scale-obtained data for a plurality of users and associate the respective scale-obtained data with each respective user based on scale-obtained biometrics and user profiles, as discussed in further detail herein. The user display 102 is arranged with the platform 101. As illustrated by the dashed-lines of FIG. 1a, the scale includes processing circuitry 104, data-procurement circuitry 138, and physiologic sensors 108. That is, the dashed-lines illustrate a closer view of components of an example scale.

The physiologic sensors 108, in various embodiments, include a plurality of electrodes and force-sensor circuitry 138 integrated with the platform 101. The electrodes and corresponding force sensor circuitry 139 are configured to engage the user with electrical signals and to collect signals indicative of the user's identity and cardio-physiological measurements while the user is standing on the platform 101. For example, the signals are indicative of physiological parameters of the user and/or are indicative of or include physiologic data, such as data indicative of a BCG or ECG and/or actual body weight or heart rate data, among other data. Although the embodiment of FIG. 1a illustrates the force sensor circuitry 139 as separate from the physiological sensors 108, one of skill in the art may appreciate that the force sensor circuitry 139 are physiological sensors. Optionally, the user display 102 is arranged with the platform 101 and the electrodes to output user-specific information for the user while the user is standing on the platform 101. The processing circuitry 104 includes CPU and a memory circuit with user-corresponding data 103 stored in the memory circuit. The processing circuitry 104 is arranged under the platform 101 upon which the user stands, and is electrically integrated with the force sensor circuitry 139 and the plurality of electrodes (e.g., the physiologic sensors 108).

The data indicative of the identity of the user includes, in various embodiments, user-corresponding data, biometric data obtained using the electrodes and/or force sensor circuitry, voice recognition data, images of the user, input from a user's device, and/or a combination thereof and as discussed in further detail herein. The user-corresponding data includes information about the user (that is or is not obtained using the physiologic sensors 108,) such as demographic information or historical information. Example user-corresponding data includes height, gender, age, ethnicity, exercise habits, eating habits, cholesterol levels, previous health conditions or treatments, family medical history, and/or a historical record of variations in one or more of the listed data. The user-corresponding data is obtained directly from the user (e.g., the user inputs to the scale) and/or from another circuit (e.g., a smart device, such a cellular telephone, smart watch and/or fitness device, cloud system, etc.). The user-corresponding data 103 is input and/or received prior to and/or in response to the user standing on the scale.

In various embodiments, the processing circuitry 104 is electrically integrated with the force sensor circuitry 139 and the plurality of electrodes and configured to process data obtained by the data-procurement circuitry 138 while the user is standing on the platform 101. The processing circuitry 104, for example, generates cardio-related physiologic data corresponding to the collected signals that is manifested as user data. Further, the processing circuitry 104 generates data indicative of the identity of the user, such as a user ID and/or other user identification metadata. The user ID is, for example, in response to confirming the identification of the user using the collected signals indicative of the user's identity.

For example, the scale identifies the user, in various embodiments, by verifying a scale-based biometric using the signals indicative of the user's identity and a user profile corresponding to the user. The scale can identify the user based on the time of day, length of foot, shape of foot, toe print, toe-tapped password, spoken words from the user, weight, height, facial features, and among other biometrics or identification data. A plurality of users may use the scale and configure the scale to include user profiles corresponding to each respective user. The user profiles include various scale-obtained biometrics that are learned by the scale (such as in an initialization mode) and used to identify the user. For example, the scale compares collected signals to the user profile to verify the scale-based biometric. In response to a match with one of the user profiles, the scale identifies the user standing on the scale as the user corresponding to the matching user profile.

Biometrics, as used herein, are metrics related to human characteristics and used as a form of identification and access control. Scale-based biometrics includes biometrics that are obtained using signals collected by the data-procurement circuitry of the scale (e.g., using electrodes and/or force sensors). Example scale-based biometrics include foot length, foot width, weight, voice recognition, facial recognition, an ECG-to-BCG timing relationship, BCG or ECG characteristics, a passcode tapped and/or picture drawn with a foot of the user on the FUI/GUI of the user display, among other biometrics. In some specific embodiments, a scale-based biometric includes a toe-print (e.g., similar to a finger print) that is recognized using a toe-print reader on the FUI/GUI of the scale. The toe print can be used as a secure identification of the user. In other embodiments, the scale-based biometric includes a finger print captured using a user device in communication with the scale (e.g., a cellphone or tablet having finger print recognition technology). In some specific embodiments, a wearable device, such as a ring, wristband, and/or ankle bracelet can be used to positively identify a user, with or without biometrics.

In various embodiments, user devices provide authorization data to the scale to authorize communication between the devices (e.g., for the scale to act as a hub for collecting data). Example authorization data includes data selected from the group consisting of a password, a passcode, a biometric, a cellphone ID, and a combination thereof. A user device-based biometric, in various embodiments, includes biometrics selected from the group consisting of: a finger print, voice recognition, facial recognition, DNA, iris recognition, typing rhythm, and a combination thereof, in various embodiments. Responsive to collecting the authorization data and/or verifying the authorization data as corresponding to the user, the user device outputs the authorization data to the scale. The authorization data is collected, in various embodiments, prior to, during, and/or after, the scale collects various signals. The scale can authorize communication of user data between the scale and the user device in response to verifying that the user data corresponds to the same user as is standing on the scale (e.g., based on a scale-based biometric and data in storage). In some specific embodiments, a wearable device, such as a ring, wristband, and/or ankle bracelet can be used to positively identify a user, with or without biometrics.

The user data collected by the scale, in some embodiments, includes the raw signals, bodyweight, body mass index, heart rate, body-fat percentage, cardiovascular age, balance, tremors, among other non-regulated physiologic data. The user data collected by the scale can further includes force signals, PWV, weight, heartrate, BCG, balance, tremors, respiration, data indicative of one or more of the proceeding data, and/or a combination thereof. In some embodiments, the user data includes the raw force signals and additional physiologic parameter data is determined using external circuitry. Alternatively, the user data can include physiologic parameters such as the PWV, BCG, IPG, ECG that are determined using signals from the data-procurement circuitry and the external circuitry (or the processing circuitry 104 of the scale) can determine additional physiologic parameters (such as determining the PWV using the BCG) and/or assess the user for a condition or treatment using the physiologic parameter. In various embodiments, the processing circuitry 104, with the user display 102, displays at least a portion of the user data to the user. For example, user data that is not regulated is displayed to the user, such as user weight. Alternatively and/or in addition, the user data is stored. For example, the user data is stored on the memory circuit of the processing circuitry (e.g., such as the physiological user-data database 107 illustrated by FIG. 1*a*). The processing circuitry 104, in various embodiments, correlates the collected user-data (e.g., physiologic user-data) with user-corresponding data, such as storing identification metadata that identifies the user with the respective data.

An algorithm to determine the physiologic data from raw signals can be located on the scale, on another device (e.g., external circuitry, cellphone), and on a Cloud system. For example, the Cloud system can learn to optimize the determination and program the scale to subsequently perform the determination locally. The Cloud system can perform the optimization and programming for each user of the scale.

The scale can optionally collect physiologic data from other devices, such as medical devices (implantable or not), user devices, wearable devices, and/or remote-physiological devices. The data can include glucose measurements, blood pressure, ECG or other cardio-related data, body temperature, among other physiologic data. In various embodiments, the user devices can include implantable medical devices and/or other medical devices, such as a pacemaker that securely shares data to the scale. Further, the scale can act as a hub to collect data from a variety of sources. The sources includes the above-noted user devices. The scale can incorporate a web server (URL) that allows secure, remote access to the collected data. For example, the secure access can be used to provide further analysis and/or services to the user. The scale and other device (or external circuitry) can pair and/or otherwise communication in response to a verification or authorization of the communication, which can be based on confirming identification of the other device, and that the same user is using the other device and the scale, and/or a scale-based biometric that is recognized, as further described herein.

As used herein, a user device includes processing circuitry and output circuitry to collect various data (e.g., signals) and communicate the data to the scale and/or other circuitry. Example user devices include cellphones, tablets, standalone servers, among other devices. A wearable device is a user device (and/or a remote user-physiologic device) that is worn by a user, such as on a user's wrist, head, or chest. Example wearable devices include smartwatches and fitness bands, smartglasses, chest heart monitors, etc. A remote user-physiologic device is a user device (and/or a wearable device) that further includes sensor circuitry or other circuit to collect physiologic data from the user, and, can optionally be in secured communication with the scale or other circuitry. Example remote user-physiological devices include smartwatches or fitness bands that collect heart rate and/or ECG and/or body temperature, medical devices, implanted medical devices, smartbeds, among other devices. Example physiologic data collected by remote user-physiologic devices includes glucose measurements, blood pressure, ECG or other cardio-related data, body temperature, among other data. As used herein, the terms "user device", "wearable device", and "remote user-physiologic device" can be interchangeably used, as one of skill may appreciate that in specific examples, a particular device may be considered one or more of a user device, a wearable device, a remote user-physiologic device. As a specific example, a particular remote user-physiologic device is a smartwatch and can be referred to as a wearable device or a user device. In other aspects, the remote user physiologic device may not be a wearable device, such as a medical device that is periodically or temporarily used.

In specific embodiments, in response to the user standing on the scale, the scale collects signals indicative of cardio-physiological measurements (e.g., force signals). The processing circuitry 104, processes the signals to generate cardio-related physiologic data manifested as user data and outputs the user data to the external circuitry. In various embodiments, the processing includes adding (and later storing) data with a time stamp indicating a time at about when the physiologic parameter data is obtained.

In a number of embodiments, the processing circuitry 104 and/or the scale includes an output circuit 106. The output circuit 106 receives the user data and, in response, sends the user data, including the data indicative of the user's identity and the generated cardio-related physiologic data, from the scale for reception at a remote location (e.g., to external circuitry for assessment). The external circuitry is at a remote location from the scale and is not integrated with the scale. The communication, in various embodiments, includes a wireless communication and/or utilizes a cloud system.

In various embodiments, the output circuit 106 provides data to the user via a user interface. The user interface can be integrated with the platform 101 (e.g., internal to the scale) and/or can be integrated with external circuitry that is not located under the platform 101. In some embodiments, the user interface is a plurality of user interfaces, in which at least one user interface is integrated with the platform 101 and at least one user interface is not integrated with the platform 101.

A user interface includes or refers to interactive components of a device (e.g., the scale) and circuitry configured to allow interaction of a user with the scale (e.g., hardware input/output components, such as a screen, speaker components, keyboard, touchscreen, etc., and circuitry to process the inputs). The user interface is integrated with the platform (e.g., internal to the scale) and/or is integrated with external circuitry that is not located under the platform, in various aspects. A user display includes an output surface (e.g., screen) that shows text and/or graphical images (e.g., the FUI or GUI) as an output from a device to a user (e.g., cathode ray tube, liquid crystal display, light-emitting diode, organic light-emitting diode, gas plasma, touch screens, etc.) For example, output circuit 106 can provide data for display on the user display 102 the user's weight and the data indicative of the user's identity and/or the generated cardio-related physiologic data corresponding to the collected signals.

The user interface can be or include a graphical user interface (GUI), a FUI, and/or voice input/output circuitry. The user interface can be integrated with the platform 101 (e.g., internal to the scale) and/or can be integrated with external circuitry that is not located under the platform 101. In some embodiments, the user interface is a plurality of user interfaces, in which at least one user interface is integrated with the platform 101 and at least one user interface is not integrated with the platform 101. Example user interfaces include input/output devices, such as display screens, touch screens, microphones, etc.

A FUI is a user interface that allows for the user to interact with the scale via inputs using their foot and/or via graphic icons or visual indicators near the user's foot while standing on the platform. In specific aspects, the FUI receives inputs from the user's foot (e.g., via the platform) to allow the user to interact with the scale. The user interaction includes the user moving their foot relative to the FUI, the user contacting a specific portion of the user display with their foot, etc. In a specific example, when the user stands on the platform of the scale, and the scale detects touching of the toe, the scale can reject the toe touch (or tap) as a foot signal (e.g., similar to wrist rejection for capacitive tablets with stylus). In some embodiments, the user display includes a touch screen and the user interaction includes the user selecting an icon, an item in a list, a virtual keyboard, among other selections, using a portion of their foot.

For example, the FUI can display various tests and/or functions that can be performed and the user can select one of the test or functions by contacting their toe with an icon of the respective test or function. In response to the selection, the scale performs the test or function. Alternatively and/or in addition, the scale is configured with a haptic, capacitive or flexible pressure-sensing upper surface, the (upper surface/tapping) touching from or by the user is sensed in the region of the surface and processed according to conventional X-Y grid Signal processing in the logic circuitry/CPU that is within the scale. By using one or more of the accelerometers located within the scale at its corners, such user data entry is sensed by each such accelerometer so long as the user's toe, heel or foot pressure associated with each tap provides sufficient force. In some embodiments, the user display is integrated with motion sense circuitry. The user interaction, in such embodiments, include the user moving their foot (with or without touching the user display). In various embodiments, the control of the FUI can be provided to a separate user device, such a user device that has previously been or is paired with the scale and that is detected by the scale. As a specific example, the scale provides a cellphone with control functions to control the display of the FUI in response to detecting the cellphone is within a threshold distance. In a specific example, when the user stands on the platform of the scale, and the scale detects touching of the toe, the scale can reject the toe touch (or tap) as a foot signal (e.g., similar to wrist rejection for capacitive tablets with stylus).

A GUI is a user interface that allows the user to interact with the scale through graphical icons and visual indicators. As an example, the external circuitry includes a GUI, processing circuitry, and output circuitry to communicate with the processing circuitry of the scale. The communication can include a wireless or wired communication. Example external circuitry can include a wired or wireless tablet, a cellphone (e.g., with an application), a smartwatch or fitness band, smartglasses, a laptop computer, among other devices. In other examples, the scale includes a GUI and voice input/output circuitry (as further described below) integrated in the platform 101. The user interact with the scale via graphical icons and visual indicators provided via the GUI and voice commands from the user to the scale.

Voice input/output circuitry (also sometimes referred to as speech input/output) can include a speaker, a microphone, processing circuitry, and other optional circuitry. The speaker outputs computer-generated speech (e.g., synthetic speech, instructions, messages) and/or other sounds (e.g., alerts, noise, recordings, etc.) The computer-generated speech can be predetermined, such as recorded messages, and/or can be based on a text-to-speech synthesis that generates speech from computer data. The microphone captures audio, such a voice commands from the user and produces a computer-readable signal from the audio. For example, the voice input/output circuitry can include an analog-to-digital converter (ADC) that translates the analog waves captured by the microphone (from voice sounds) to digital data. The digital data can be filtered using filter circuitry to remove unwanted noise and/or normalize the captured audio. The processing circuitry (which can include or be a component of the processing circuitry 104) translates the digital data to computer commands using various speech recognition techniques (e.g., pattern matching, pattern and feature matching, language modeling and statistical analysis, and artificial neural networks, among other techniques).

In various embodiments, the external circuitry is part of a scale-based heuristic system. The external circuitry can pool user data from a plurality of scales in a user-specific knowledge database 112. As previously discussed, the user data includes data that is sensitive to the user, e.g., user-sensitive data, and/or that the user would otherwise not want compromised. To prevent the data from being compromised and/or the identity of the user being learned, the processing circuitry 104 of the scale removes portions of the user data that identifies the user and adds an identifier (e.g., code) that uniquely identifies the user and the scale to user data corresponding to each respective user. The removed portions, in some embodiments, includes a user ID, user name, date of birth, location, and a combination thereof. The identifier, in various embodiments, includes a scale ID and a user ID. For example, the scale ID remains the same for each user of the scale and identifies the scale. The user ID, by contrast, is different for each user of the scale and uniquely identifies the respective user profile corresponding to the scale. The identifiers (scale ID or user ID), in some embodiments, includes numeric and/or alphabetic assignment and/or is based on identifying data, such as an IP address of the scale and/or a social security (or part thereof) number of the user.

The external circuitry receives the user data and, in response, replaces the identifier with an alias ID. For example, the external circuitry creates an alias ID corresponding to each identifier and, for certain types of access requests, provides the alias identifier in place of the identifier. Further, the external circuitry stores the user data with the identifier in the user-specific knowledge database 112 and stores the identification of the scale and user that correspond to the alias ID in another database. For security purposes, the identifier is encrypted and access to the encrypted identifier can be restricted. The scale and/or the external circuitry, in various embodiments, encrypt the identifier. In various embodiments, the user data is sent over time. Thereby, the user-specific knowledge database 112 includes historical data for the user. The alias ID, in some embodiments, is associated with a generic user profile such that user data with the alias ID is associated with the same generic user profile over time.

An alias ID, as used herein, is data that is independent of the identifier (e.g., not invertible back to the identifier) and formatted as the identifier is. That is, the alias ID is used in place of the identifier that identifies the user and the scale and that appears in the same format. The alias ID includes a substitute value for the identifier that has no algorithmic relationship with the identifier and is not reversible. The alias ID is provided in place of the identifier for certain types of access requests. Therefore, the alias ID is used in place of the identifier for accessing the user data unless the user data is requested by an authorized user (such as, the user corresponding to the user data and/or a physician for a fee). The system stores the user data in a user-specific knowledge database 112 with the alias IDs, and stores an association of each alias ID to a scale and user in the other database. The user-specific knowledge database 112 is more accessible than the other database, which may be more secure than the user-specific knowledge database 112. The system may maintain the association between the alias ID and the user data, regardless of the form of the sensitive user data. Thus, the association remains the same whether the user data is decrypted, formatted, encrypted or re-encrypted using a different encryption scheme.

An output of the system provides the alias ID in place of the identifier for accesses to the user data unless the sensitive data is specifically requested by an authorized user. The alias IDs are independent of the sensitive user data in that the identifier that indicates identification of the user and the scale cannot be derived directly from the alias IDs. This independence can be implemented using a variety of alias ID creation techniques such as a randomly generated identifier, a sequentially generated identifier, or a non-invertible derivation of the transaction card identifier. The aliases may also be uniquely associated with exactly one scale and one user. In some instances, the user, administrator, or another application using the invention may configure the format of the alias IDs. For example, the user may designate that the alias IDs should be formatted to each contain six capital letters or to each contain nine digits (the numbers "6" and "9" being merely illustrative). In another embodiment, the user may designate a portion of the identifier that is retained and used as a portion of the alias ID. In one such example, the system uses the first number of an identifier as the first number of its corresponding alias.

The alias ID is generated, in some embodiments, as a hash value. For example, the external circuitry generates a hash value for each identifier or encrypted identifier. The external circuitry uses this hash value for searching, sorting, and similar database-related processes. For instance, the hash value may represent alphanumeric, numeric, or other limited values. The hash value may also represent a compression of the identifier. Additionally, the external circuitry may format the hash value further by using another hash algorithm, such as first using Secure Hash Algorithm (SHA-1) and then using Media Digest Algorithm (MD5). Once the hash value has been created, a database application may use the hash when accessing the database. For example, to search for identification of a user of user data in the second database, the system determines the identifier hash value for use in finding records that correspond to the hash value.

The identifier and/or portions of the user data can optionally be encrypted. The scale and/or the external circuitry encrypt the data using a suitable encryption scheme. Examples of encryption schemes that can be used include, but are not limited to, AES, Data Encryption Standard (DES), and International Data Encryption Algorithm (IDEA). For example, in some embodiments, the scale encrypts the identifier and/or the user data. Further, if the user data is not encrypted by the scale, the external circuitry encrypts the data (e.g., a secret) and, optionally, serves as an encryption key for decrypting the indication and/or user data.

The external circuitry can change the alias IDs periodically, in response to an event, and/or in response to access of the user data. For example, each time the scale communicates user data to the external circuitry, the alias ID is changed and the external circuitry associated prior received user data with subsequent user data. The user-specific knowledge database 112 and other databases are updated with the changed alias ID.

In various embodiments, the other database is used to identify the scale and user. For example, the external circuitry, such as a standalone CPU, uses the other database to identify the scale and user corresponding to the alias ID. The identification can be used to provide a notification and/or additional data to the user through the scale. For example, in various embodiments, the user-specific knowledge database 112 is used to identify correlated user data and identify various patterns of risks or conditions or diseases based on the correlation. The user, in some embodiments, is notified of a potential correlation. The notification can be on the user display and/or another user device. The external circuitry can output the correlations that includes user data with alias IDs. For example, output data may not identify that the user has such a problem or correlation but rather generic correlations of user data with alias IDs. The output data, optional, identifies patterns of risk for conditions or disease based on the correlation (without actually identifying the user has the condition or disease but indicating correlation). Further, based on the correlation, the user can receive an advertisement, such as an advertisement for a physician, prescription drug, health program, and/or social group, as discussed further herein.

Although the present embodiments disclose the external circuitry replacing the identifier with an alias ID, embodiments are not so limited. For example, the scale, in some embodiments, removes the identifying information and adds an alias ID. In such embodiments, the external circuitry pools the user data with the alias IDs in the user-specific knowledge database 112 and may not include the other database. That is, the external circuitry may not have the knowledge of the identification of the scale and user that correspond with the user data. Rather, the external circuitry only correlates the user data with specific generic user (non-identifiable) using the alias ID. Alternatively, the scale may separately send the correlation of the alias ID with the scale and the user to the external circuitry for storage in the other database.

Figure 1B:
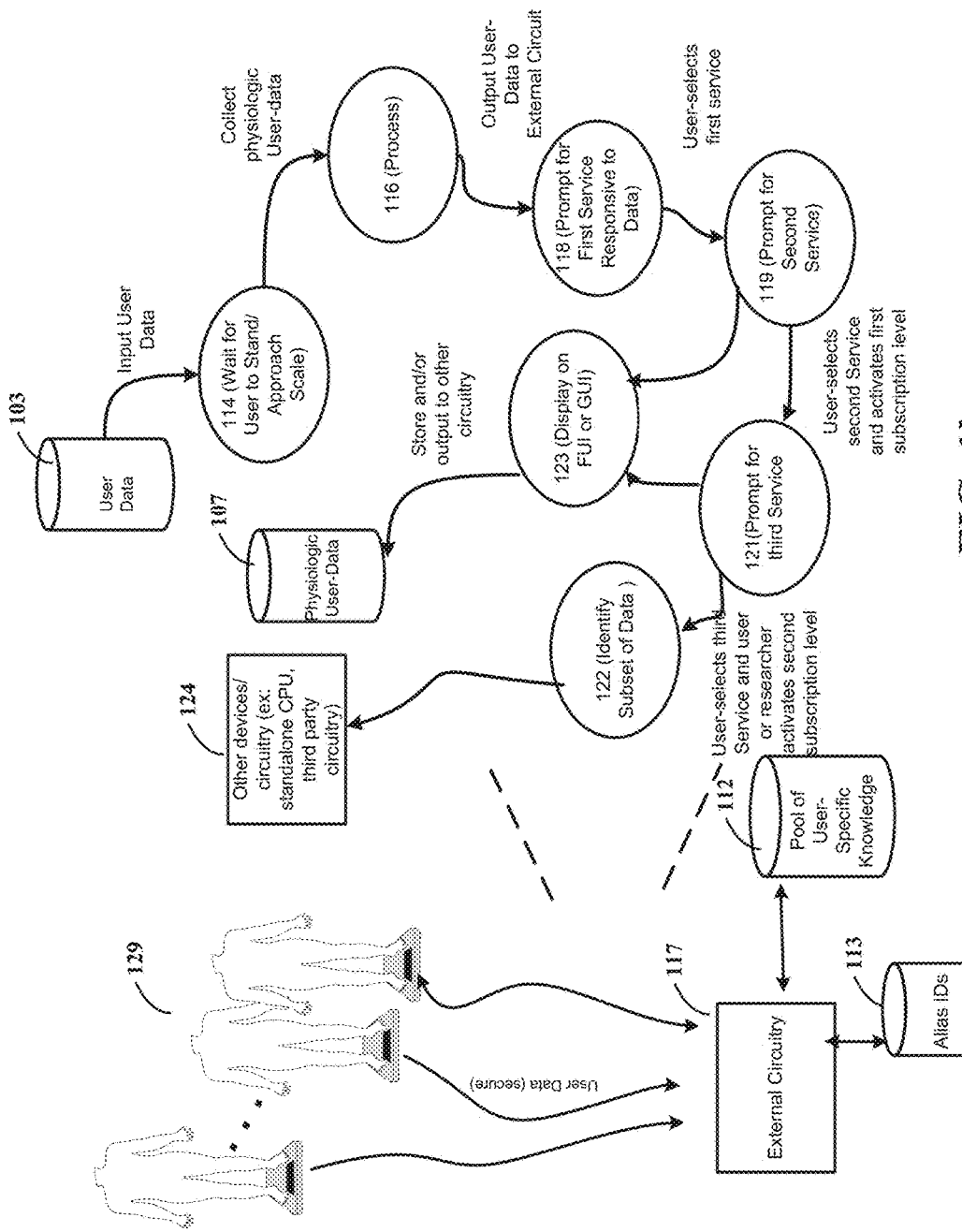
FIG. 1b shows an example of providing a hierarchy of services using scale-based user physiological data and a scale-based user-physiological heuristic system consistent with aspects of the present disclosure.

FIG. 1b shows an example of providing hierarchy of services using scale-based user-physiological data and a scale-based user-physiological heuristic system consistent with aspects of the present disclosure. The scale-based user-physiological heuristic system includes a plurality of scales 129 and external circuitry 117. Each scale is configured to monitor signals from a plurality of users, correlate the respective data with the appropriate user using scale-based biometrics and user profiles, and communicate the signals and/or data to the external circuitry 117.

The external circuitry 117, in various embodiments, includes a processing circuit and a memory circuit. The external circuitry 117 receives the user data from the scales 129 and stores the user data with alias IDs replacing identifying information in the user-specific knowledge database 112. The user data is collected and stored by the external circuitry 117 over time. For example, the external circuitry 117 validates the received user data as corresponding to a particular user associated with an alias ID based on the identifier and correlates the received user data with other user data stored in the user-specific knowledge database 112 and associated with the alias ID. The external circuitry then updates the user-specific knowledge database 112 with the user data and/or other feedback data obtained. In response to not identifying the identifier (in the second database), the external circuitry 117 generates a new alias ID for the respective scale and user. Further, the external circuitry 117 stores an indication of which scale and user corresponds to the alias ID in another database (e.g., the alias ID database 113). For example, the other database (e.g., the alias ID database 113) includes a list of alias IDs to scale ID and user ID to identify the scale corresponding to the alias ID and the respective user of the scale. Alternatively and/or in addition, the scale outputs user data with an alias ID. In some embodiments, the scale outputs the correlation of the alias ID with a respective scale and user to the external circuitry.

Typically, the alias ID is randomly generated, but it also can be generated by other means, such as a sequential generation or by generating a hash value of the sensitive data. The system then stores the alias ID and encrypted user data in a first database. In an example embodiment, the user of the external circuitry determines the format of the alias IDs. In another embodiment, the alias IDs have the same format as the original identifier.

In various embodiments, the scale and/or external circuitry 117 encrypts all and/or portions of the user data. For example, in one embodiment, the encryption and decryption are implemented with a single device (e.g., the external circuitry) capable of both encryption and decryption of data. In other embodiments, encryption is implemented using multiple devices (e.g., one for encryption and one for decryption).

After the alias IDs are generated, the external circuitry 117 provides access to the user data with alias IDs, in various embodiments. The access, in some embodiments, includes the external circuitry using the user data to provide a hierarchy of services. In some embodiments, at least one service provided includes providing portions of the user data to other circuitry 124 for analytic purposes and/or to a particular scale. Typically, when user data is requested, the external circuitry 117 provides the user data with the alias IDs instead of the identifiers. In this manner, user data can be used without supplying the original identification of users/scales that correspond to the user data.

Each scale can include the scale, including the platform 101 and user display 102, as previously illustrated and discussed with regard to FIG. 1a. For example, as illustrated by FIG. 1b, a scale at block 114 waits for a user to stand on the platform, and, optionally is in a reduced power-consumption mode of operation. User-corresponding data 103 is input and/or received prior to and/or in response to the user standing on the scale. In response to the user standing on the scale, the scale collects signals indicative of cardio-physiological measurements (e.g., force signals). At block 116, the scale processes the signals to generate cardio-related physiologic data manifested as user data and outputs the user data to the external circuitry 117. In various embodiments, the processing includes adding (and later storing) data with a time stamp indicating a time at about when the physiologic parameter data is obtained.

As previously discussed, the scales 129 secure the user data by removing portions of the user data that identifies the respective users and adding an identifier that uniquely identifies the user and the scale. The external circuitry 117 receives the user data and replaces the identifiers with alias IDs, stores the user data with the alias IDs in a user-specific knowledge database 112 and identifies which scale and user corresponds to the respective alias ID in another database 113.

As further previously discussed, the hierarchy of services are enabled based on user selection and activation of different service levels of different weighted values. The weighted values, in some embodiments, authorize access to user data and/or functions performed on the user data and is based on the value to the user, provider of the service, and/or a third party. For example, when a user uses a scale, a base-level of services are provided and that have a weighted value of zero. The base-level includes a subscription level zero, in some embodiments, and includes the scale providing weight measurements and collecting user data. In various embodiments, the subscription level zero includes outputting the user data to the external circuitry 117 to identify correlations between users and/or potential risks for conditions.

As a specific example, the user is provided a prompt for a first service, at block 118, based on the external circuitry 117 identifying a correlation. The correlation includes risks, priority of the user data, and/or social groupings. A prompt, as used herein, includes a notification displayed on a user interface, such as the user interface of the scale or a user interface of another user device that is in communication with the scale. The prompt is provided in the middle of another action on the scale/device (e.g., interrupts the user or the device) or provided the next time the user accesses the scale/device. The user is provided with the service, in various embodiments, in response to the user selecting the prompt on the respective user interface and/or activating the service level of the service by providing the weighted value. In a specific embodiment, the user is provided the prompt on a foot-controlled user interface of the scale. The user selects the prompt by moving their foot in relation to the user interface of the scale and verifying authorization of providing the weighted value (e.g., an amount or fee for the subscription level). Alternatively, the user selects the prompt and the weighted value is provided by another party, such as a researcher.

The user data with a priority, as used herein, includes an importance of the user and/or the user data. In accordance with a number of embodiments, the scale is configured to collect data for multiple users and identifies one or more of the multiple users of the scale that have priority user data. The importance of the user is based on parameter values identified and/or user goals, such as the user is an athlete and/or is using the scale to assist in training for an event (e.g., marathon) or is using the scale for other user goals (e.g., a weight loss program). Further, the importance of the user data is based on parameter values and/or user input data indicating a diagnosis of a condition or disease and/or a risk of the user having the condition or disease based on the scale-obtained data. For example, the scale-obtained data of a first user indicates that the user is overweight, recently had an increase in weight, and has a risk of having atrial fibrillation. The first user is identified as a user corresponding with priority user data. A second user of the scale has scale-obtained data indicating a decrease in recovery parameters (e.g., time to return to baseline parameters) and the user inputs an indication that they are training for a marathon.

The second user is also identified as a user corresponding with priority user data. The scale displays indications to the user with the priority user data, in some embodiments, on how to use to the scale to communicate the user data to external circuitry for further processing, correlation, and/or other features, such as social network connections. Further, the scale, in response to the priority, displays various feedback to the user, such as user-targeted advertisements and/or suggestions. In some embodiments, only users with priority user data have data output to the external circuitry to determine risks and/or additional services to offer, although embodiments in accordance with the present disclosure are not so limited.

The first service pertains to the subscription level zero and includes a weighted value of zero. Thereby, any user of a scale can access services of the subscription level zero. In various embodiments, services of subscription level zero include generic health information, social groupings of consumer related interest, advertisements for products or services, and are in response to the user data from the scale.

In various embodiments, the external circuitry 117 identifies correlations between the user data of respective users. For example, the external circuitry 117 identifies various correlations between the user data stored in the user-specific knowledge database 112 and associated with different users. The correlations include various patterns, symptoms, risk, and/or other similar data between user data sets. The correlation, in some embodiments, includes grouping users into groups based on similar symptoms, physiological parameter values, diagnosis, prescription drug user, lifestyle habits, medical history and a combination thereof and identify correlations.

In some embodiments, the external circuitry 117 includes and/is in communication with a database storing reference information. The reference information includes data and statistics of a variety of conditions, symptoms, parameter values indicative of conditions, assessment data of people experiencing the condition, government provided health information and/or databases, and a combination thereof. The reference information is stored in a structured database and/or in an unstructured database. In some embodiments, the reference information includes the user-specific knowledge database 112. The user-specific knowledge database 112 includes pooled user data from a plurality of scales that is updated over time. Thereby, data from the scales, in some embodiments, is used to identify trends, risks, and/or parameter values associated with and/or indicative of particular conditions. In various embodiments, the pooled data is secured (e.g., securely pooled user data) using a variety of security techniques, as described herein.

In response to the user selecting the prompt for the first service, the scale and/or external circuitry provides the first service. For example, the external circuitry 117 provides the scale with generic health information that is based on a risk that the user has a condition and/or is otherwise related to the user data (e.g., lifestyle or user goals). In other embodiments, the first service includes providing the user with a link to a webpage for a social group, such as a forum and/or page of a social network, that is related to a consumer interest and based on the user data. Alternatively and/or in addition, the user is provided with various advertisements based on the user data. In some embodiments, in response to the user selecting the advertisement, the provider of the service and/or scales is provided with a weighted value.

In various embodiments, data resulting from and/or included in the service (e.g., first service, second service, etc.) is displayed on a user interface of the scale and/or a user interface of another device, at block 123. Further, the data is stored on the scale and/or on external circuitry (e.g., physiological data 107). For example, the scale receives the data from the external circuitry 117 and discerns data to display. In some embodiments, the scale includes a display configuration filter (e.g., circuitry and/or computer readable medium) configured to discern the data to display to the user. The display configuration filter discerns which portions of the user data and/or information from the services to display to the user using the user interface of the scale based on various user demographic information (e.g., age, gender, height, diagnosis) and the amount of data. For example, the data may include an amount of data that if all the data is displayed on the user interface of the scale, the data is difficult for a person to read and/or uses multiple display screens.

The display configuration filter discerns portions of the data to display using the user interface based on the data and the demographic information, and discerns other portions of the data to display on another user device. The other user device is selected by the scale (e.g., the filter) based on various communication settings. The communication settings include settings such as user settings (e.g., the user identifying user devices to output data to), scale-based biometrics (e.g., user configures scale, or default settings, to output data to user devices in response to identifying scale-based biometrics), and/or proximity of the user device (e.g., the scale outputs data to the closest user device among a plurality of user devices and/or in response to the user device being within a threshold distance from the scale), among other settings. For example, the scale determines which portions of the information to output to the other particular user device based on user settings/communication authorization (e.g., what user devices are authorized by the user to receive particular user data from the scale), and proximity of the user device to the scale. The determination of which portions to output is based on what type of data is being displayed, how much data is available, and the various user demographic information (e.g., an eighteen year old is able to see better than a fifty year old). For example, the scale includes different modes of communicating, as discussed in further detail herein.

Further, the user selecting the prompt for the first service, in accordance with various embodiments, drives displaying a prompt for a second service, at block 119. The second service includes a service pertaining to a subscription level one. The subscription level one, in various embodiments, provides services of a higher level than the subscription level zero and includes a first weighted value. The first weighted value is greater than zero and is based on the value of the service to the user, the service provider and/or a third party. In various embodiments, services of subscription level one include providing the user data to a physician for diagnosis purposes, physiological social groupings, and/or advertisements for products or services based on diagnosis by the physician, among other services.

In response to the user selecting the prompt for the second service and providing the first weighted value, the first subscription level is activated and the second service is provided to the user. For example, the external circuitry 117 provides the user data to a physician and obtains diagnosis data from the physician in response to their review. Alternatively and/or in addition, the external circuitry 117 identifies other users with the diagnosis and/or similar physiological parameters and groups the users. Data resulting from the second service (e.g., diagnosis data, link to the social group, advertisements based on the diagnosis) is output from the external circuitry 117 to the scale for display to the user, at block 123.

Further, the user selecting the prompt for the second service, in accordance with various embodiments, drives a display of a prompt for a third service, at block 121. The third service includes a service pertaining to a subscription level two. The subscription level two, in various embodiments, provides services of a higher level than the subscription level one and includes a second weighted value. The second weighted value is based on the value of the service to the user, the service provider and/or a third party. In various embodiments, services of subscription level two include providing a subset of user data to a third party for research and/or studies, providing a subset of the user data to the user, providing physician advice and suggestions, providing additional services (e.g., track other data from other devices), professional social groupings, and/or among other services.

In response to the user selecting the prompt for the third service and providing the second weighted value, the second subscription level is activated and the third service is provided to the user. In various embodiments, a third party, such as a requester of the subset of user data provides the second weighted value. For example, in various embodiments, the third service include providing subsets of the user data, at block 122. The data provided includes user data with the alias IDs as stored in the user-specific knowledge database 112, which is provided with the alias IDs to protect the identity of the users.

In various specific embodiments, the hierarchy of services includes providing a subset of the (securely) pooled user data to a requester, such as a physician and/or other researcher, and/or using the scales to participate in a study and/or experiment. The subset of user data provided to a requester is provided, in various embodiments, based on analysis parameters and security parameters. The analysis parameters are input by the requester for the data, and include parameters such as demographics of users, conditions or diseases, parameter values, lifestyle, and/or pseudo-random selection. The security parameters include restrictions on the user data output to protect the identity of the users and the user data, which include sensitive data. For example, various sources/entities request access to the user data. In some instances, the requester for the user data includes a researcher intending to perform research on the user data. Example sources/entities include government entities for research or census studies, environment groups, scientific research groups, including both private, academic, and public source, among other entities. The research is performed on existing user data and/or the requester requests specific data that is consequently obtained. For example, in response to analytics performed and/or prior to, the researcher requests that the external circuitry contact particular user to perform an experiment. Various users are contacted based on the analysis parameters (e.g., the parameters of the research) such as user demographic information, parameter values, and/or lifestyle indicators. The users are contacted through the user display of the scale and asked if they are interested in participating in a statistic study, an experimental study, and/or an observation study. In some embodiments, a portion of the users are used as a control group and the remaining portion as an experimental group. The scale, in some embodiments, is used to perform the study and/or encourage the user to actively participate.

In other embodiments, the requester for the user data includes a user of one of the plurality of scales 129. For example, the user may be interested in learning about a particular disorder. The user may know that they themselves have a disorder/condition or have a goal or may be interested in learning more for someone they know. The user provides the various analysis parameters using their scale and/or another user device. The scale communicates with the external circuitry 117 to authorize the communication and outputs data to the scale. The scale, in some embodiments, outputs the user data to another user device, such that the user can more easily view the data but the communication with the external circuitry 117 is through the scale and responsive to identification of the user.

The external circuitry 117 identifies the various user data to output to the requester based on the analysis parameters and the security parameters. In various embodiments, the analysis parameters identify various types of user data, such as demographics of users, conditions/disorders, lifestyle, user goals, physiological data, etc., that the requester is interested in. In some embodiments, the analysis parameters establish various bias parameters and/or requests for pseudo-random selection to provide analytics on a statistically random sample population. The analysis parameters further include sample size (e.g., number of users) and/or data of the data obtained. In other embodiments, the analysis parameters identify various parameters, conditions or goals the requester is interested in learning about and potential failures, successes, and/or correlated diagnosis. The external circuitry 117 scans the user-specific knowledge database 112 to identify various user's data related to the analysis parameters and collects the respective user data.

Based on the security parameters, the external circuitry 117 removes portions of the respective user data and/or does not include the portions of the user data in the user-specific knowledge database 112. Thereby, the security parameters restrict access to the user data. User data sets corresponding to each user include data that is unrelated to the analysis parameters and/or otherwise not used for the purpose of analysis as requested. Such data is not provided to the requester. In various embodiments, the security parameters include specific data that cannot be accessed by requesters and/or restrictions on combinations of data. The identification is based on the risk of the data, such as location data and/or date of birth.

In various aspects, the user data has a sensitivity value that identifies a security risk of the data. The sensitivity values are set by the external circuitry 117 and/or the users of the scales. User data types with a sensitivity value above a threshold value may not be provided to requesters. Alternatively, data is provided based on a security of the requester. For example, if the requester has a high amount of security measures in place, a greater amount of data and/or data with higher sensitivity values is provided. If the requester has a low amount of security in place, a lower amount of data and/or only data with lower sensitivity values is provide. Examples of security measures in place include firewalls, encryption schemes used, access to the requesters database by external sources, authentication of people when accessing the data, such as tokens, passwords, and/or biometrics, among other security measures.

The scale can define a user data table that defines types of user data and sensitivity values of each type of user data. In specific embodiments, the FUI displays the user data table. In other specific embodiments a user interface of a smartphone, tablet, and/or other computing device displays the user data table. For example, a wired or wireless tablet is used, in some embodiments, to display the user data table. The sensitivity values of each type of user data, in some embodiments, define in which communication mode(s) the data type is communicated and/or which biometric is used to enable communication of the data type. In some embodiments, a default or pre-set user data table is displayed and the user revises the user data table using the FUI. The revisions are in response to user inputs using the user's foot and/or contacting or moving relative to the FUI. Although the embodiments are not so limited, the above (and below) described control and display is provided using a wireless or wired tablet or other computing device as a user interface. The output to the wireless or wired tablet, as well as additional external circuitry, is enabled using biometrics. For example, the user is encouraged, in particular embodiments, to configure the scale with various biometrics. The biometric include scale-based biometrics and biometrics from the tablet or other user computing device. The biometric, in some embodiments, used to enable output of data to the tablet and/or other external circuitry, includes a higher integrity biometric (e.g., higher likelihood of identifying the user accurately) than a biometric used to identify the user and stored data on the scale.

An example user data table is illustrated below:

| | User-data Type | | | | |
|---|---|---|---|---|---|
| | Weight, local weather | Body Mass Index, user specific news | User-Specific Advertisements | Physician-Provided Diagnosis/ Reports | Scale-stored suggestions (symptoms & diagnosis) |
| Sensitivity (10 = highest, 1 = lowest) | 1 | 3 | 5 | 10 | 9 |

The above-displayed table is for illustrative purposes and embodiments in accordance with the present disclosure and can include additional user-data types than illustrated, such as cardiogram characteristics, clinical indications, physiological parameters, user goals, demographic information, etc. In various embodiments, the user data table includes additional rows than illustrated. The rows, in specific embodiments, include different data input sources and/or sub-data types (as discussed below). Data input sources include source of the data, such as physician provided, input from the Internet, user provided, from the external circuitry. The different data from the data input sources, in some embodiments, is used alone or in combination.

In various related embodiments, the security parameters include a set of rules restricting access to combinations of user data. For example, a particular requester is provided user data of particular combinations. The rules may include "can receive 2 out of the three: height, data of birth, and location data." The set of rules prevents the requester from being able to identify the user's identities. Further, the external circuitry 117, in some embodiments, changes the alias IDs each time a requester requests user data to prevent the requester from correlating a first data set with a second data set and obtaining the combination of user data that the set of rules are designed to prevent.

In a number of aspects, the user-specific knowledge database 112 includes a bias. For example, the user of the scale may include health conscious users and/or unhealthy or sick users. In some embodiments, the bias is such that the user-specific knowledge database 112 does not represent a random sample census of user data from a population. The external circuitry 117, optionally, identifies what the potential bias is. The external circuitry 117 provides the identified potential bias to the requester such that the requester can correct for the bias by adjusting the selection of user data and/or the external circuitry 117 can adjust the selection of user data to correct for the bias.

The external circuitry 117 (and/or the scale) can periodically change one or more alias IDs and updates the second database 113. For example, the external circuitry assigns a new alias ID to user data corresponding to a specific user each time the scale sends user data to the external circuitry. If previous data is compromised, such as by a security hacker, subsequent user data is more difficult to correlate to the previously compromised data. The external circuitry identifies that the subsequent user data is correlated with a generic user and previously provided user data based on a correlation of the old alias ID with the new alias ID. For example, the first database, as previously discussed, includes generic user profiles corresponding with the alias IDs. The alias IDs of the generic user profiles, in some embodiments, are updated in response to the changes in alias IDs. Alternatively, the correlation between the old alias ID and changed alias ID is stored in the second database and used to identify correlations of subsequent user data with historical user data.

The correlation can be used to provide generic health information to the user. For example, the external circuitry 117 identifies the scale and user that the particular user data is associated with and outputs data, such as the generic health information, to the identified scale. For example, the external circuitry 117 identifies which scale a particular user data set corresponds to that has an identified correlation or risk using the other database. The identification, in some embodiments, includes identification of the scale, and, optionally, a specific user. The external circuitry 117 identifies generic health information to provide the user and outputs the generic health information to the scale. The generic health information is displayed to the user, such as using the scale display or another user device depending on user preferences. For example, in response to identifying the user standing on the scale using a scale-based biometric, the scale displays an indication that additional information is available to the user and/or a synopsis of the additional information and to log-in to their smartphone or other user device to view the additional information. The generic health information, as discussed further herein, includes various symptoms, risk factors, or advice to provide the user based on the identified correlation.

In various embodiments, the external circuitry 117 revises correlations identified using the (securely) pooled user data in the user-specific knowledge database 112 over time. For example, user data is received from a plurality of scales over time. Additional users receive a scale and provide additional data. Further, over time, the scale obtains additional data from the user. The external circuitry dynamically revises and updates correlations of the user-specific knowledge database based on the additional user data received from the plurality of scales and additional scales added to the system. The user data can be compared against historical user data for the same user and used to analyze if the user's condition/treatment and risk is getting better or worse over time and can be updated over time using the dynamically revised correlations as a service.

For example, the external circuitry receives the user data and identifies a risk that the user has a condition using the user-specific knowledge database 112 and/or reference information and the user data provided by the scale. The risk is identified by comparing the user data to the reference information and (securely) pooled user data and identifying a match. The risk of a condition, as previously discussed, includes a probability that the user has the condition and a severity of the condition.

Although the present example embodiments provided above are in reference to external circuitry performing the determination, embodiments in accordance with the present disclosure are not so limited. For example, the processing circuitry of the scale can determine the risk by accessing the reference information.

In accordance with various embodiments, although not illustrated by FIG. 1a or FIG. 1b, the system includes an additional sensor circuitry that is external to the scale. The additional sensor circuitry can include a communication circuit and is configured and arranged to engage the user with electrical signals and collect therefrom signals indicative of an ECG of the user. The sensor circuitry, which may include and/or be correlated with processing circuitry configured to derive an ECG from the collected signals. The sensor circuitry communicates the ECG to the external circuitry 117 and the scale can communicate a BCG to the external circuitry 117.

In accordance with various embodiments, the external circuitry updates the user-specific knowledge database 112 using various user information. For example, the user-specific knowledge database 112 includes user data from a plurality of scales. The external circuitry and/or the scale updates the database 112 with the user data, the test results, and the responses to the questions. For example, the responses to the questions may identify a diagnosis the user has from a doctor and/or additional symptoms the user is experiencing. This information is used to dynamically update the database 112 and potentially revises (e.g., increase or decreases) risks identified by the external circuitry.

For example, in a number of embodiments, the scale including the processing circuitry provides a number of questions to the user in response to input from the external circuitry. The scale can be used to provide questions to the user and obtain answers from the user. For example, the FUI can display a plurality of questions using the user display. Using user interaction by the user's foot, the FUI receives user inputs (e.g., answers) to each of the questions and, using the output circuit, stores the user inputs within a user profile associated with the user. For example, the FUI provides a number of questions in a question and answer session to identify symptoms, diagnosis, lifestyle data, family medical history, among other questions. The questions can be provided via a speaker component of the scale outputting computer generated natural voice (via a natural language interface), displaying the questions on the user display 102, and/or outputting the questions to another user-device. As previously described, the scale can (alternatively and/or in addition to a FUI or GUI) have a voice input/output circuitry that can obtain user's answers to questions via voice comments and inputs user information in response (e.g., a speaker component to capture voice sounds from the user and processing circuitry to recognize the voice commands and/or speech). The scale provides the input to the external circuitry 117 and the external circuitry 117 verifies or revises the risk identified. Further, the external circuitry updates the user-specific knowledge database 112.

In accordance with the present disclosure, a risk for a condition is identified and/or adjusted based on demographics of the users, disorders, disease, symptoms, prescription or non-prescription drugs, treatments, past medical history, family medical history, genetics, life style (e.g., exercise habits, eating habits, work environment), among other categories and combinations thereof, and based on user data in the stored user database. A particular scale is provided with data indicative of the correlation and using data that has alias IDs. The external circuitry can provide the data in response to an indication that the user is interested in the data and based on scale-obtained data corresponding to the user. In a number of embodiments, various physiological factors are an indicator for a disease and/or disorder. For example, an increase in weight, along with other factors, can indicate an increased risk of atrial fibrillation. Further, atrial fibrillation is more common in men. In some instances, symptoms of a particular disorder can be different for different categories of interest (e.g., symptoms of atrial fibrillation can be different between men and women). For example, in women, systolic blood pressure is associated with atrial fibrillation. In other instances, sleep apnea may be assessed via an ECG and is correlated to the weight of the user. Furthermore, various cardiac conditions can be assessed using an ECG. For example, atrial fibrillation can be characterized and/or identified in response to a user having no or fibrillating p-waves, no QRS complex, and no baseline/inconsistent beat fluctuations. Atrial flutter, by contrast, can be characterized by having no p-wave, variable heart rate, having QRS complexes, and a generally regular rhythm. Ventricular tachycardia (VT) can be characterized by a rate of greater than 120 beats per minute, and short or broad QRS complexes (depending on the type of VT). Atrio-Ventricular (AV) block can be characterized by PR intervals that are greater than normal (e.g., a normal range for an adult is generally 0.12 to 0.20 seconds), normal-waves, QRS complexes can be normal or prolong shaped, and the pulse can be regular (but slow at 20-40 beats per minute). For more specific and general information regarding atrial fibrillation and sleep apnea, reference is made herein to https://www.clevelandclinicmeded.com/medicalpubs/diseasemanagement/cardiology/atri al-fibrillation/ and http://circ.ahajournals.org/content/118/10/1080.full, which are fully incorporated herein for its specific and general teachings. Further, other data and demographics that are known and/or are developed can be added and used to derive the various reference information.

Such generic health information includes life-style suggestions, suggested prescription medicine and/or why it is prescribed, and/or other advice, such as symptoms that the user should watch for. For instance, the user data may suggest that the user has a heart condition and/or disorder. The generic health information suggests prescription medicine to the user to ask their physician about and/or provides potential symptoms that the user should watch for and/or should go to the physician's office or an emergency room if the symptoms arise.

For example, the external circuitry 117 receives the user data that corresponds to the plurality of users from the plurality of scales. The respective user data is received at over-lapping times and/or separate times. In response to receiving the user data, the external circuitry, in various embodiments, identifies the respective plurality of users based on an identifier and/or other identifying data and, correlates the received user data with generic profiles of the respective plurality of users based on an already generated alias ID and/or a newly generated alias ID. Each alias ID identifies that the user data corresponds to a particular user (e.g., and previously stored data corresponding to that particular user) but does not provide an identity of the user. In a number of embodiments, the external circuitry identifies (e.g., determines) risks for conditions or diseases by comparing the user data with reference information. The external circuitry identifies that a particular user is at risk for the condition or disease, identifies the respective user and scale using the second database, and outputs the generic health information to the scale that is tailored to each respective user based on the risk for the condition. The external circuitry further instructs the scales to collect feedback data, including symptoms, experiences, demographic information, medical history information etc., and uses the feedback data to revise and/or verify the risk. In some embodiments, the feedback data and the user data is used to update a user-specific knowledge database 112, which is used to refine the identified risks. Alternatively and/or in addition, the scale can prompt the user to perform additional tests, such as breath hold, valsalva, etc.

Although the present embodiments illustrate discussion of three subscription levels and particular services for subscription levels, the embodiments are not limited to the number of subscription levels described and/or services listed. For example, one or more of the above listed services, in some embodiments, are included in an additional level and/or in a higher or lower level of subscription than described.

Figures 1C, 1D:
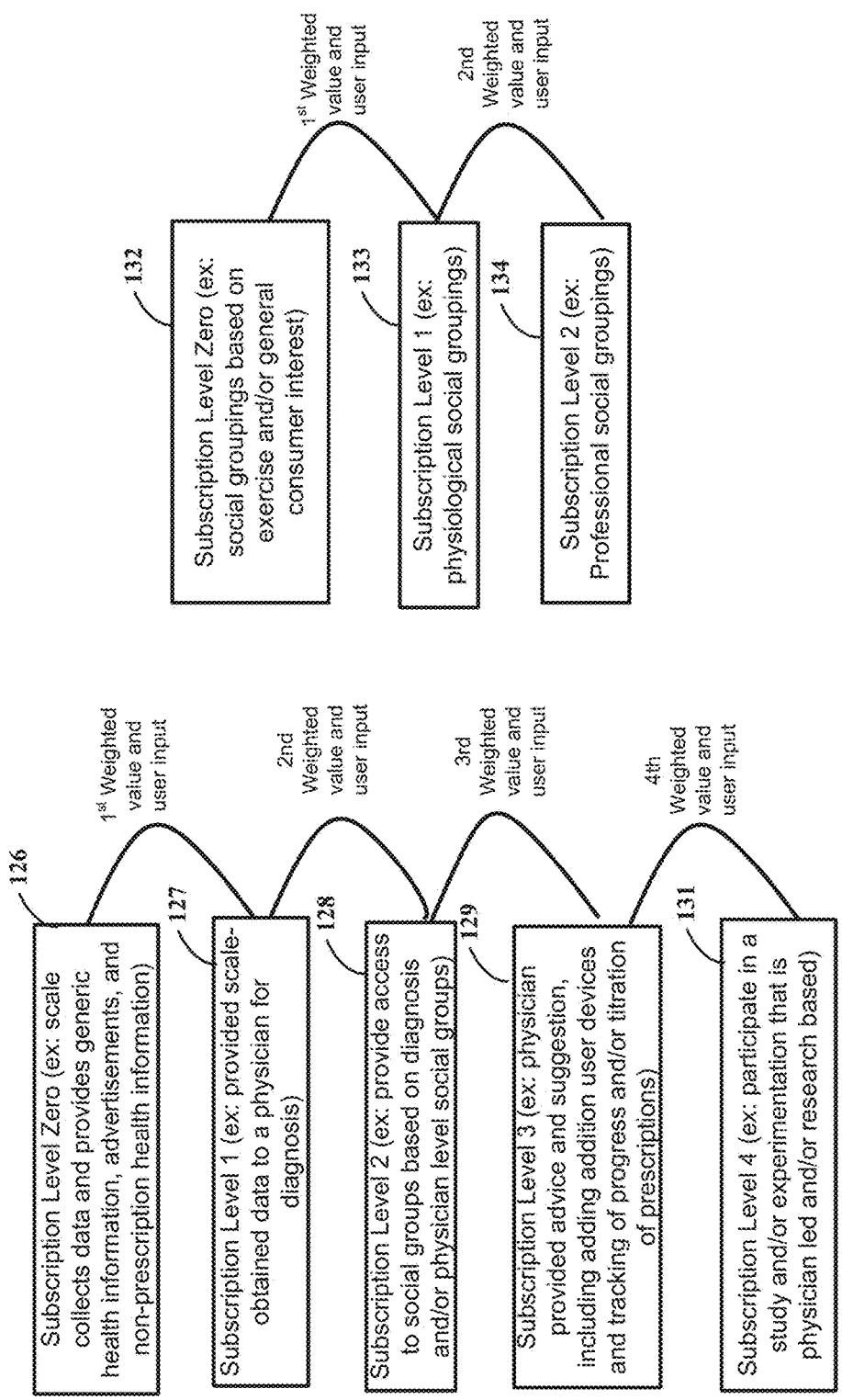
FIGS. 1c-1d show examples of different hierarchies of services provided using scale-based user physiological data consistent with aspects of the present disclosure.
Figure 1C:
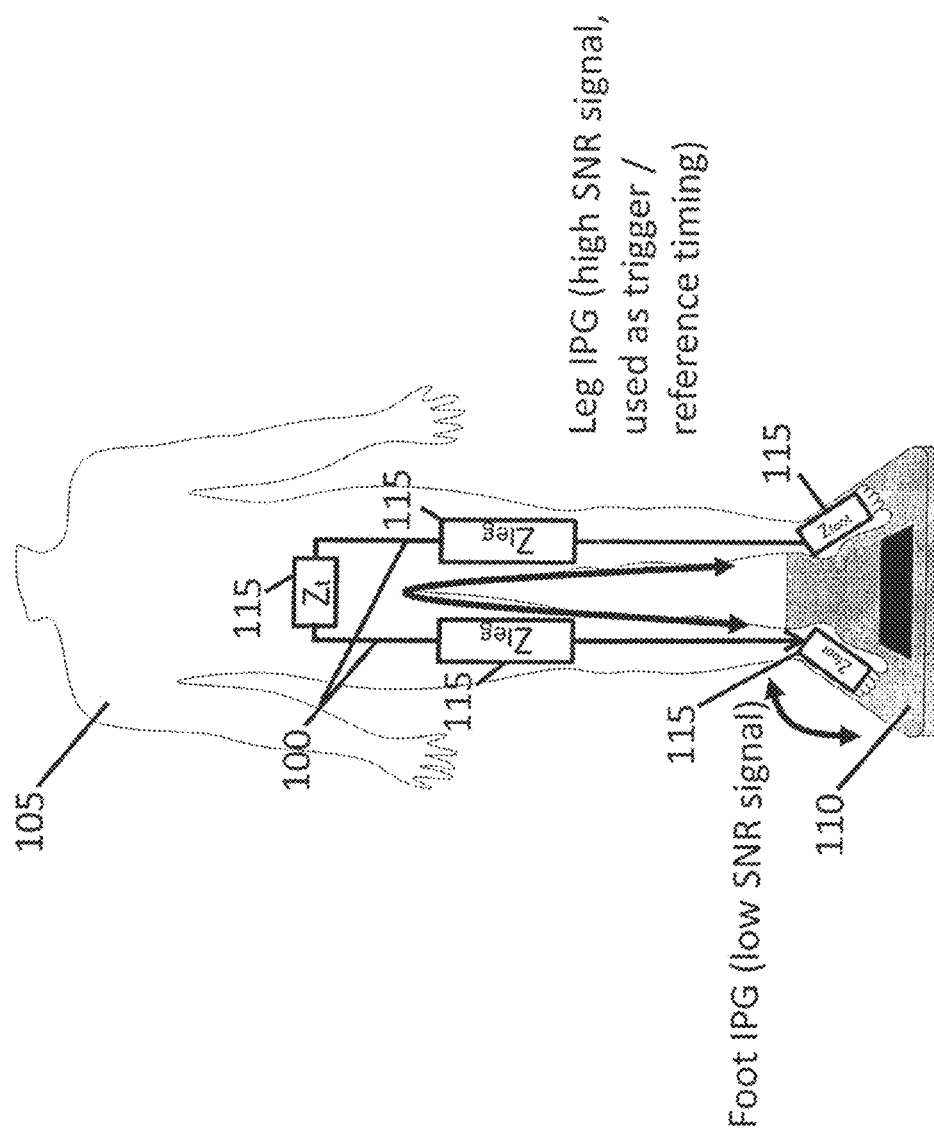

FIGS. 1c-1d show examples of different hierarchies of services provided using scale-based user physiological data consistent with aspects of the present disclosure. For example, FIG. 1c illustrates an example of a hierarchy of services provided from five subscription levels. A prompt for the various services is provided to a particular user in response to scale-obtained data and/or previous selection of a prompt for another service. In this manner, the users of the scales are provided with prompts for information in response to their scale-obtained data indicating risks for conditions and/or based on user-specific interests to prevent users from being over-whelmed with data and/or receiving data that is not interesting. Further, users indicate an interest in obtaining additional data and services by selecting prompts for the services of the hierarchy.

As illustrated, subscription level zero 126 has a weight of zero. A prompt for a service pertaining to subscription level zero 126 is provided to a user of the scale in response to the user data obtained using the scale. Further, the service is provided to the user in response to the user selecting the prompt. Example services for subscription level zero include generic health information, advertisements, and non-prescription health information that is correlated to the scale-obtained user data.

Subscription level one 127 has a first weighted value. A prompt for a service pertaining to subscription level one 127 is provided to a user of the scale in response to the user selecting a prompt for a service of subscription level zero 126. The first weighted value, in various embodiments, is greater than zero. Further, the service is provided to the user in response to the user selecting the prompt and providing the first weighted value. Example services for subscription level one 127 include providing the scale-obtained data to a physician for diagnosis purposes.

Subscription level two 128 has a second weighted value. A prompt for a service pertaining to subscription level two 128 is provided to a user of the scale in response to the user selecting a prompt for a service of subscription level one 127 and activating the subscription level one 127 by providing the first weighted value. The second weighted value, in various embodiments, is greater than the first weighted value. Further, the service is provided to the user in response to the user selecting the prompt and providing the second weighted value. Example services for subscription level two 128 include providing the user access to different social groups based on the diagnosis and/or professional social groups, as discussed further herein.

Subscription level three 129 has a third weighted value. A prompt for a service pertaining to subscription level three 129 is provided to a user of the scale in response to the user selecting a prompt for a service of subscription level two 128 and activating the subscription level two 128 by providing the second weighted value. The third weighted value, in various embodiments, is greater than the second weighted value. Further, the service is provided to the user in response to the user selecting the prompt and providing the third weighted value. Example services for subscription level three 129 include additional physician-provided advices and suggestions, such as titration of prescriptions and/or further tracking of user data, and/or tracking of data from additional devices.

Subscription level four 131 has a fourth weighted value. A prompt for a service pertaining to subscription level four 131 is provided to a user of the scale in response to the user selecting a prompt for a service of subscription level three 129 and activating the subscription level three 129 by providing the third weighted value. The fourth weighted value, in various embodiments, is greater than the third weighted value. Further, the service is provided to the user in response to the user selecting the prompt and providing the fourth weighted value. In some embodiments, the fourth weighted value is provided by a third party, such as a physician and/or researcher. Example services for subscription level four 131 include participation in a study and/or experiment that is physician-led and/or research-based.

The scale can be used by multiple different users. A subset or each of the different users can have user devices that can be synchronized to the scale and/or can be in communication and display scale-obtained data via a GUI of the user device. The multiple users may synchronize their respective user devices to the common scale (or to multiple scales). Each of the different users may have activated a level and/or different subscription levels and the scale can store an indication of the activation. The scale can selectively provide services of the different subscription levels to the respective users by verifying the identity of the user and/or verifying that the user device has verified (or is used by) the same identified user. In specific embodiments, the scale can verify that the user device identified the user within a threshold period of time prior to synchronizing and/or communicating scale-obtained data.

The scale can be used in different setting and/or modes, such as a consumer mode, a professional mode, and a combination mode. A consumer mode includes a scale as used and/or operated in a consumer setting, such as a dwelling. As a specific example, a scale is located in a dwelling with five different people. Each of the five different people use the scale, and three of the five people have activated subscription levels above a zero or base level. Prior to providing a service to a user, the identity of the respective user is verified via the scale using scale-based biometric. As users in a consumer mode may be familiar with one another (e.g., live together), the identification of the user by the scale can be based on weight, body-mass-index, and/or other data. Although embodiments are not so limited and the identification can be based on other biometrics and/or passcodes.

In other instances the scale is used in a professional setting, such as a medical office, and/or in a professional mode. A professional mode includes an operation of the scale as used and/or operated in a professional setting, such as a doctor's office, exercise facility, nursing home, etc. In a professional mode, the scale is used by different users that may not be familiar with one another. The different users may have services with the professional to track and/or aggregate data from the peripheral device. Similar to the consumer mode, the scale can selectively provide the services by verifying the identity of the user. The identification can include higher-level biometrics and/or identifications than the consumer mode. As a specific professional mode example, a scale is located at a doctor's office and is used to obtain data from multiple patients (e.g., 10 in a day, 500 in a year). When a patient checks-in, they stand on the scale and the scale-obtained data is output to external circuitry for document retention and/or other purposes. A subset (or all) of the patients participate or use a service that corresponds with and/or includes acquisition and/or aggregation of data from a user device and the scale, and provides the aggregated data to the doctor (via external circuitry, such as server CPU) for review. For example, a user with atrial fibrillation can wear a smartwatch to track various cardio-related data during exercise and/or other periods of time and which is output to the scale at the doctor's office and/or other external circuitry. The scale, in the professional mode, may be used to obtain data from more users than a scale used in a consumer setting.

The scale can also be in a combination consumer/professional mode. A combination consumer/professional mode includes a scale as used and/or operated in a consumer setting for purposes and/or uses by a professional, and/or in a professional setting for purposes and/or uses by the consumer (e.g., use by the consumer outside of the professional setting and/or in addition to). As a specific example, a scale is located at a user's dwelling and used by multiple family members. A first user of the family is diagnosed with a heart-related condition and the doctor may offer a service to review data from the scale (and optionally another user device) of the first user. When the other family members stand on the scale, the scale operates in the consumer mode. The other family members may or may not have the service activated for the doctor to review data and the scale operates via the consumer mode. When the first user that is diagnosed with heart-related condition stands on the scale, the scale recognizes the user and operates in a professional mode or a combination mode. For example, the scale outputs aggregated data from the scale to external circuitry that is accessible by the doctor of the first user.

The hierarchy of services offered and/or corresponding levels can be different between the different operation modes. In an example consumer mode, the hierarchy of services offered can include services based on scale-obtained data at one or more lower subscription levels, services based on pooled data from a plurality of scales at one or more middle subscription levels, and services based on physician or other professional review at one or more higher subscription levels. For example, in a consumer mode, a first subscription level service may include providing the user access to health magazines that correspond to the user based on scale-obtained data, a second subscription level service may include providing the user access to a social group of the other users with similar demographic background and/or health condition, and a third subscription level may include providing physician diagnosis of the user based on scale-obtained data.

In an example professional mode, the hierarchy of services offered can include services based on scale-obtained data at one or more lower subscription levels, services related to the professional and/or business at one or more middle subscription levels, and services for a study and/or research at one or more higher subscription levels. For example, in a professional mode, a first subscription level service may include providing the user with access to health information that corresponds to the user based on scale-obtained data, a second subscription level service may include the physician tracking various data from the user over time, a third subscription level service may include a physician's using the data obtained from the user in a study. To participate in the study, the user may be given access to a social group and/or purchase (or be provided as compensation) a scale for use at home and to communicate with external circuitry.

In an example combination mode, the hierarchy of services offered can include services based on scale-obtained data at one or more lower subscription levels, services based on data communicated between multiple scales and/or user devices at one or more middle subscription levels, and pooled data from a plurality of scale's at one or more higher subscription levels. For example, in a combination mode, a first subscription level service may include providing the user with access to health information that corresponds to the user based on scale-obtained data, a second subscription level service may include communicating data from the scale to another scale or other circuitry (at the professional location or consumer location, respectively), and a third subscription level service may include a use by the professional or other business, such as a study by the physician, on-demand personal training by an exercise facility, review of the scale-obtained data, generating and monitoring progress toward a goal and/or lifestyle changes, etc. The above described hierarchy of services for different scale operation modes includes examples and the embodiments in accordance with the present disclosure are not so limited.

Data provided to the user and/or the professional can default to be displayed on the FUI of the scale, the GUI of the user device, and/or a GUI of other external circuitry depending on the use of the scale. In a consumer mode and/or combination consumer/professional mode, data can default to display on the FUI of the scale. The defaulted display of data can be revised by the user providing inputs to display the data on the GUI of a user device or a GUI of another external circuitry (e.g., a standalone CPU) and/or automatically by the scale based on past scale-based actions of the user. As a specific example, a first user provided a user input to the scale to display data on the GUI of the user device multiple times (e.g., more than a threshold number of times, such as five times). In response, the scale adjusts the defaulted display and output data to the GUI of the user device. The display on the FUI of the scale and/or GUI of the user device (or other external circuitry) can include an indication that the user device is inaccurate, an available time-synchrony service, and/or an option to override the time-synchrony, among other displays. In a professional mode, the scale is not owned by the user. The user may be uninterested in synchronizing their user device with the professional's scale. The display may default to the GUI of the user device to display an option to synchronize, and/or to override the time-synchrony. Alternatively, the display may default to the FUI of the scale to display an option to synchronize and, responsive to user verification or authority to synchronize, defaults to display on the GUI of the user device. During the combination consumer/professional mode, portions of scale-obtained data for a particular user may default to display on external circuitry, such as a standalone or server CPU that is accessible by the professional.

FIG. 1d shows an example of a hierarchy of social grouping services provided using scale-based user physiological data consistent with aspects of the present disclosure. The social grouping services illustrated by FIG. 1d, in various embodiments, is provided in combination with the services illustrated by FIG. 1c.

In various embodiments, the external circuitry groups respective sets of user data into groups. The groups are based on demographics, user goals, symptoms, physiological parameter values, diagnosis, prescription drug usage, lifestyle habits, medical history, family medical history, and a combination thereof. For example, the external circuitry groups user data based on fitness goals (current or historical). The correlation, in some instances, is provided to the user, without identifying specific other users, such that the user identifies how other users of a similar demographic reached their fitness goals. In other embodiments, the correlation includes users with a specific condition, disorder, and/or disease and causes of improvements or potential lack of improvement of symptoms of the condition, disorder and/or disease, such as lifestyle changes, prescription drugs, and/or change in exercise habits or geographic location. Thereby, the (securely) pooled user data is used to educate users based on other user's successes, failures, and/or general result.

In accordance with a number of embodiments, the hierarchy of services is based on the grouping of users. For example, one or more services of one or more subscription levels includes providing access to different social grouping of users. The access, in some embodiments, includes access to a forum, webpage, and/or application. Alternatively and/or in addition, the access is to reports and/or dashboards of scale-obtained data from the users of the social group over a period of time, such as changes in physiological parameters and/or weights and potential causes of the changes (e.g., treatments, exercise, lifestyle changes). Social groupings, as used herein, includes grouping of a set of scale users based on scale-obtained data. The forum, webpage, and/or application provided as the service includes automatically linking the uses of the group and providing the users access. In various embodiments, the forum, webpage and/or application is automatically populated with reports of the user, such as rankings, progress of the users, new observation, and/or other information. In a number of embodiments, users in the social groupings remain anonymous and are identified by their alias ID and/or another ID selected by the user. In some embodiments, the social groups are intra scale or inter scale. For example, the scale is configured to collect user data for two or more users and correlate the respective data with a user profile of each respective users. The social grouping can include the users of the scale (e.g., intra scale) and/or users of different scales (e.g., inter scale) based on the pooled database of user data.

The social grouping of an intra scale includes grouping the users of the scale and providing various reports, updates, alerts, and/or forums for the users of the group to interact. The forum, blog, and/or webpage, in some embodiments, includes a private (or public) page of a social network webpage that the users of the group access and communicate. A private page, for instance, is only accessible by the users of the group and/or persons authorized by users of the group. In other embodiments, the social groupings are inter scale. For example, an external circuitry, such as a server CPU, may receive user data (with user identifying data removed) from a plurality of scales and identifies various users with correlated user data. The users with correlated user data, such as demographic data and/or scale-obtained data, are grouped by the external circuitry without user input. The external circuitry outputs an indication of an available social group to the scales of the users with the correlated user data and each scale displays, using the user interface of the scale, an alert of an available social group. The user accesses the social grouping using the user interface of the scale and/or a standalone CPU that is in communication with the scale. For example, in response to an alert, the user selects an interest in the social grouping using the user interface of the scale. The scale outputs the indication and a link to a webpage or application associated with the social group (or information on how to access the social grouping) via the standalone CPU, such as a user smartphone or tablet. The webpage includes, in some embodiments, a page of a social network, an application or portal for the user to log-in to, a forum, etc. In various embodiments, data is tracked for users of the social group and reports are provided, such as rankings of the users in the group, progress of the users, new observations, and/or information learned. In other embodiments, the indication includes a notification that a report and/or dashboard is available and/or an alert. Alternatively and/or in addition, the users of the group are provided a forum to discuss various health issues, successes, failures, exercise, eating, etc.

As a specific example, a scale is used by a family training for a marathon. Each member of the family uses the scale to track various physiological parameters, including cardiogram related characteristics, recovery parameters, weight, body-mass-index, and exercise results. The family is grouped into an intra scale social grouping and provided with alerts when reports of progress and/or rankings are available for the family. In another specific example, multiple scales are used by different users located at different locations that have indicators for atrial fibrillation, are female, are over-weight, and are over the age of sixty-years old. The users are grouped into an inter scale social grouping and provided with an alert of an available social grouping. In response to at least a subset of the users selecting an interest in the social grouping, the subset of users are provided with a link to a webpage, portal, application, and/or forum. The subset of users access the link and are connected to one another. In various embodiments, user data (with user identifying data removed) is displayed to the social group so that users can view other users' success and/or failures.

In a number of specific embodiments, social groupings are provided as services in a plurality of different subscription levels. The subscription levels can have various weighted values, as previously described. For example, in a subscription level zero 132, a user is provided access to a social group based on an exercise interest and/or goals or other consumer related interest. A prompt for the social group pertaining to subscription level zero is provided to a user of the scale in response to the user data obtained using the scale. Further, access to the social group is provided to the user in response to the user selecting the prompt.

At a first subscription level 133, a user is provided access to physiological social group, which is based on scale-obtained data and/or diagnosis of the scale-obtained data by a physician. A prompt for a physiological social group pertaining to the first subscription level 133 is provided to a user of the scale in response to the user selecting a prompt for a service of subscription level zero 132. Further, access to the physiological social group is provided to the user in response to selecting the prompt and providing the first weighted value.

At a second subscription level 134, a user is provided access to the (more) professional social group. For example, a physician may participate in the professional social group with other users and/or actively track progress of the user. Alternatively and/or in addition, the physician uses the professional social group to perform a study and/or experiment. A prompt for a professional social group pertaining to second subscription level 134 is provided to a user of the scale in response to the user selecting a prompt for a service of first subscription level 133. Further, access to the professional social group is provided to the user in response to selecting the prompt and providing the second weighted value.

The remaining figures illustrate various ways to collect the physiologic data from the user, electrode configurations, and alternative modes of the processing circuitry 104. For general and specific information regarding the collection of physiologic data, electrode configurations, and alternative modes, reference is made to U.S. patent application Ser. No. 14/338,266 filed on Oct. 7, 2015 (now U.S. Pat. No. 10,130,273), which is hereby fully incorporated by references for its teachings.

FIG. 1e shows current paths 100 through the body of a user 105 standing on a scale 110 for the IPG trigger pulse and Foot IPG, consistent with various aspects of the present disclosure. Impedance measurements 115 are measured when the user 105 is standing and wearing coverings over the feet (e.g., socks or shoes), within the practical limitations of capacitive-based impedance sensing, with energy limits considered safe for human use. The measurements 115 can be made with non-clothing material placed between the user's bare feet and contact electrodes, such as thin films or sheets of plastic, glass, paper or wax paper, whereby the electrodes operate within energy limits considered safe for human use. The IPG measurements can be sensed in the presence of callouses on the user's feet that normally diminish the quality of the signal.

As shown in FIG. 1e, the user 105 is standing on a scale 110, where the tissues of the user's body will be modeled as a series of impedance elements, and where the time-varying impedance elements change in response to cardiovascular and non-cardiovascular movements of the user. ECG and IPG measurements sensed through the feet can be challenging to take due to small impedance signals with (1) low SNR, and because they are (2) frequently masked or distorted by other electrical activity in the body such as the muscle firings in the legs to maintain balance. The human body is unsteady while standing still, and constant changes in weight distribution occur to maintain balance. As such, cardiovascular signals that are measured with weighing scale-based sensors typically yield signals with poor SNR, such as the Foot IPG and standing BCG. Thus, such scale-based signals require a stable and high quality synchronous timing reference, to segment individual heartbeat-related signals for signal averaging to yield an averaged signal with higher SNR versus respective individual measurements.

The ECG can be used as the reference (or trigger) signal to segment a series of heartbeat-related signals measured by secondary sensors (optical, electrical, magnetic, pressure, microwave, piezo, etc.) for averaging a series of heartbeat-related signals together, to improve the SNR of the secondary measurement. The ECG has an intrinsically high SNR when measured with body-worn gel electrodes, or via dry electrodes on handgrip sensors. In contrast, the ECG has a low SNR when measured using foot electrodes while standing on said scale platforms; unless the user is standing perfectly still to eliminate electrical noise from the leg muscles firing due to body motion. As such, ECG measurements at the feet while standing are considered to be an unreliable trigger signal (low SNR). Therefore, it is often difficult to obtain a reliable cardiovascular trigger reference timing when using ECG sensors incorporated in base scale platform devices. Both Inan, et al. (IEEE Transactions on Information Technology in Biomedicine, 14:5, 1188-1196, 2010) and Shin, et al. (Physiological Measurement, 30, 679-693, 2009) have shown that the ECG component of the electrical signal measured between the two feet while standing was rapidly overpowered by the electromyogram (EMG) signal resulting from the leg muscle activity involved in maintaining balance.

The accuracy of cardiovascular information obtained from weighing scales is also influenced by measurement time. The number of beats obtained from heartbeats for signal averaging is a function of measurement time and heart rate. Typically, a resting heart rates range from 60 to 100 beats per minute. Therefore, short signal acquisition periods may yield a low number of beats to average, which may cause measurement uncertainty, also known as the standard error in the mean (SEM). SEM is the standard deviation of the sample mean estimate of a population mean. Where, SE is the standard error in the samples N, which is related to the standard error or the population S. The following is an example SE for uncorrelated noise:

$$SE = \frac{S}{\sqrt{N}}$$

For example, a five second signal acquisition period may yield a maximum of five to eight beats for ensemble averaging, while a 10 second signal acquisition could yield 10-16 beats. However, the number of beats available for averaging and SNR determination is usually reduced for the following factors; (1) truncation of the first and last ensemble beat in the recording by the algorithm, (2) triggering beats falsely missed by triggering algorithm, (3) cardiorespiratory variability, (4) excessive body motion corrupting the trigger and Foot IPG signal, and (5) loss of foot contact with the measurement electrodes.

Sources of noise can require multiple solutions for SNR improvements for the signal being averaged. Longer measurement times increase the number of beats lost to truncation, false missed triggering, and excessive motion. Longer measurement times also reduce variability from cardiorespiratory effects. If shorter measurement times (e.g., less than 30 seconds) are desired for scale-based sensor platforms, sensing improvements need to tolerate body motion and loss of foot contact with the measurement electrodes.

The human cardiovascular system includes a heart with four chambers, separated by valves that return blood to the heart from the venous system into the right side of the heart, through the pulmonary circulation to oxygenate the blood, which then returns to the left side of the heart, where the oxygenated blood is pressurized by the left ventricles and is pumped into the arterial circulation, where blood is distributed to the organs and tissues to supply oxygen. The cardiovascular or circulatory system is designed to ensure oxygen availability and is often the limiting factor for cell survival. The heart normally pumps five to six liters of blood every minute during rest and maximum cardiac output during exercise increases up to seven-fold, by modulating heart rate and stroke volume. The factors that affect heart rate include autonomic innervation, fitness level, age and hormones. Factors affecting stroke volume include heart size, fitness level, contractility or pre-ejection period, ejection duration, preload or end-diastolic volume, afterload or systemic resistance. The cardiovascular system is constantly adapting to maintain a homeostasis (set point) that minimizes the work done by the heart to maintain cardiac output. As such, blood pressure is continually adjusting to minimize work demands during rest. Cardiovascular disease encompasses a variety of abnormalities in (or that affect) the cardiovascular system that degrade the efficiency of the system, which include but are not limited to chronically elevated blood pressure, elevated cholesterol levels, edema, endothelial dysfunction, arrhythmias, arterial stiffening, atherosclerosis, vascular wall thickening, stenosis, coronary artery disease, heart attack, stroke, renal dysfunction, enlarged heart, heart failure, diabetes, obesity and pulmonary disorders.

Each cardiac cycle results in a pulse of blood being delivered into the arterial tree. The heart completes cycles of atrial systole, delivering blood to the ventricles, followed by ventricular systole delivering blood into the lungs and the systemic arterial circulation, where the diastole cycle begins. In early diastole the ventricles relax and fill with blood, then in mid-diastole the atria and ventricles are relaxed and the ventricles continue to fill with blood. In late diastole, the sinoatrial node (the heart's pacemaker) depolarizes then contracting the atria, the ventricles are filled with more blood and the depolarization then reaches the atrioventricular node and enters the ventricular side beginning the systole phase. The ventricles contract and the blood is pumped from the ventricles to arteries.

The ECG is the measurement of the heart's electrical activity and is described in five phases. The P-wave represents atrial depolarization, the PR interval is the time between the P-wave and the start of the QRS complex. The QRS wave complex represents ventricular depolarization. The QRS complex is the strongest wave in the ECG and is frequently used as a timing reference for the cardiovascular cycle. Atrial repolarization is masked by the QRS complex. The ST interval represents the period of zero potential between ventricular depolarization and repolarization. The cycle concludes with the T-wave representing ventricular repolarization.

The blood ejected into the arteries creates vascular movements due to the blood's momentum. The blood mass ejected by the heart first travels headward in the ascending aorta and travels around the aortic arch then travels down the descending aorta. The diameter of the aorta increases during the systole phase due to the high compliance (low stiffness) of the aortic wall. Blood traveling in the descending aorta bifurcates in the iliac branch which transitions into a stiffer arterial region due to the muscular artery composition of the leg arteries. The blood pulsation continues down the leg and foot. Along the way, the arteries branch into arteries of smaller diameter until reaching the capillary beds where the pulsatile blood flow turns into steady blood flow, delivering oxygen to the tissues. The blood returns to the venous system terminating in the vena cava, where blood returns to the right atrium of the heart for the subsequent cardiac cycle.

Surprisingly, high quality simultaneous recordings of the Leg IPG and Foot IPG are attainable in a practical manner (e.g., a user operating the device correctly simply by standing on the impedance body scale foot electrodes), and can be used to obtain reliable trigger fiducial timings from the Leg IPG signal. This acquisition can be far less sensitive to motion-induced noise from the Leg EMG that often compromises Leg ECG measurements. Furthermore, it has been discovered that interleaving the two Kelvin electrode pairs for a single foot, result in a design that is insensitive to foot placement within the boundaries of the overall electrode area. As such, the user is not constrained to comply with accurate foot placement on conventional single foot Kelvin arrangements, which are highly prone to introducing motion artifacts into the IPG signal, or result in a loss of contact if the foot is slightly misaligned. Interleaved designs begin when one or more electrode surfaces cross over a single imaginary boundary line separating an excitation and sensing electrode pair. The interleaving is configured to maintain uniform foot surface contact area on the excitation and sensing electrode pair, regardless of the positioning of the foot over the combined area of the electrode pair.

Various aspects of the present disclosure include a weighing scale platform (e.g., scale 110) of an area sufficient for an adult of average size to stand comfortably still and minimize postural swaying. The nominal scale length (same orientation as foot length) is 12 inches and the width is 12 inches. The width can be increased to be consistent with the feet at shoulder width or slightly broader (e.g., 14 to 18 inches, respectively).

Figure 1F:
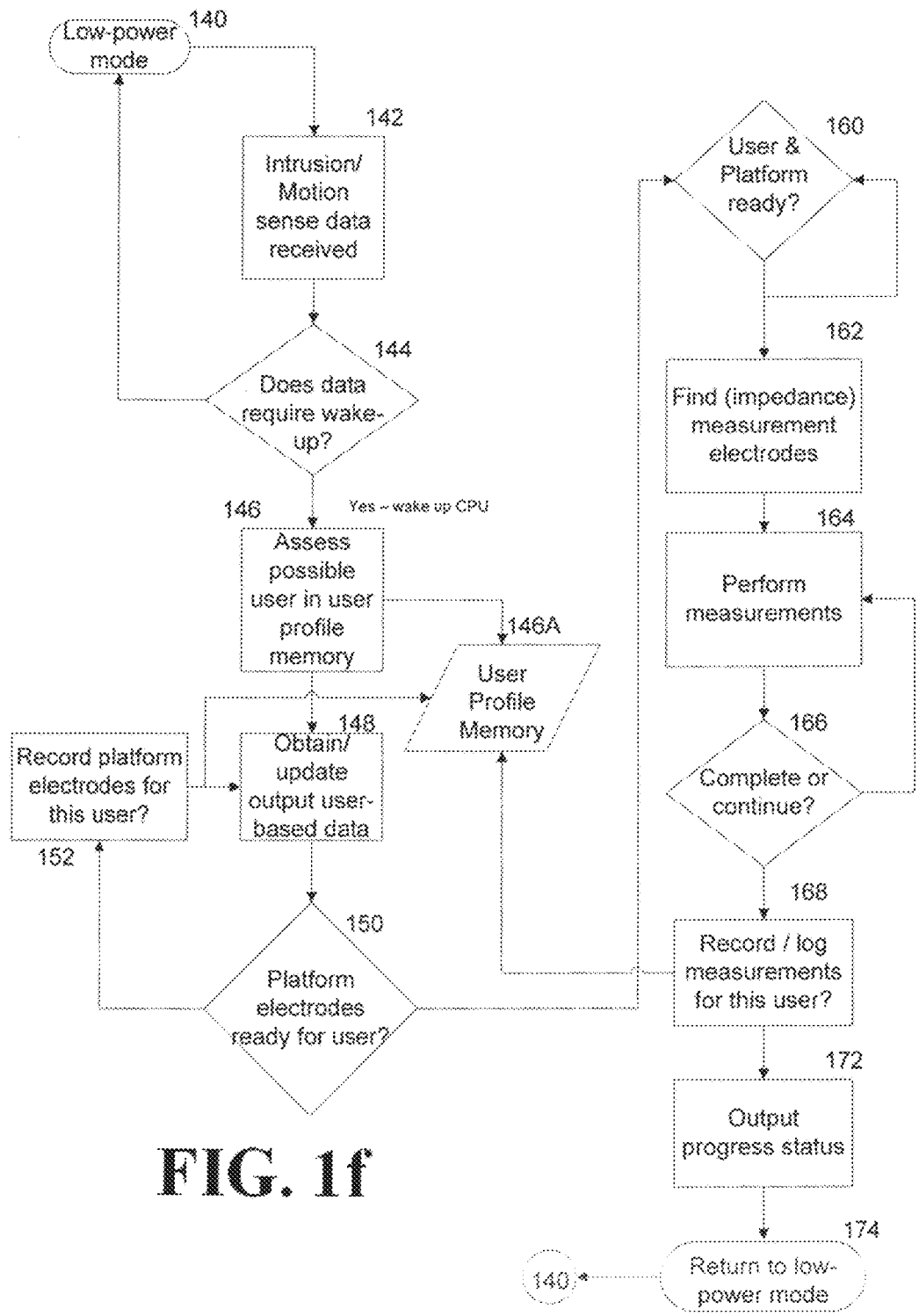
FIG. 1f is a flow chart illustrating an example manner in which a user-specific physiologic meter/scale may be programmed to provide features consistent with aspects of the present disclosure.

FIG. 1f is a flow chart depicting an example manner in which a user-specific physiologic meter or scale may be programmed in accordance with the present disclosure. This flow chart uses a computer processor circuit (or CPU) along with a memory circuit shown herein as user profile memory 146a. The CPU operates in a low-power consumption mode, which may be in off mode or a low-power sleep mode, and at least one other higher power consumption mode of operation. The CPU can be integrated with presence and/or motion sense circuits, such as a passive infrared (PIR) circuit and/or pyroelectric PIR circuit. In a typical application, the PIR circuit provides a constant flow of data indicative of amounts of radiation sensed in a field of view directed by the PIR circuit. For instance, the PIR circuit can be installed behind an upper surface which is transparent to infrared light (and/or other visible light) of the platform and installed at an angle so that the motion of the user approaching the platform apparatus is sensed. Radiation from the user, upon reaching a certain detectable level, wakes up the CPU which then transitions from the low-power mode, as depicted in block 140, to a regular mode of operation. Alternatively, the low-power mode of operation is transitioned from a response to another remote/wireless input used as a presence to awaken the CPU. In other embodiments, user motion can be detected by an accelerometer integrated in the scale or the motion is sensed with a single integrated microphone or microphone array, to detect the sounds of a user approaching.

Accordingly, from block 140, flow proceeds to block 142 where the user or other intrusion is sensed as data received at the platform apparatus. At block 144, the circuitry assesses whether the received data qualifies as requiring a wake up. If not, flow turns to block 140. If however, wake up is required, flow proceeds from block 144 to block 146 where the CPU assesses whether a possible previous user has approached the platform apparatus. This assessment is performed by the CPU accessing the user profile memory 146A and comparing data stored therein for one or more such previous users with criteria corresponding to the received data that caused the wake up. Such criteria includes, for example, the time of the day, the pace at which the user approached the platform apparatus as sensed by the motion detection circuitry, the height of the user as indicated by the motion sensing circuitry and/or a camera installed and integrated with the CPU, and/or more sophisticated biometric data provided by the user and/or automatically by the circuitry in the platform apparatus.

As discussed herein, such sophisticated circuitry can include one or more of the following user-specific attributes: foot length, type of foot arch, weight of user, and/or manner and speed at which the user steps onto the platform apparatus or by user speech (e.g., voice). In some embodiments, facial or body-feature recognition may also be used in connection with the camera and comparisons of images therefrom to images in the user profile memory.

From block 146, flow proceeds to block 148 where the CPU obtains and/or updates user corresponding data in the user profile memory. As a learning program is developed in the user profile memory, each access and use of the platform apparatus is used to expand on the data and profile for each such user. From block 148, flow proceeds to block 150 where a decision is made regarding whether the set of electrodes at the upper surface of the platform are ready for the user, such as may be based on the data obtained from the user profile memory. For example, delays may ensue from the user moving his or her feet about the upper surface of the platform apparatus, as may occur while certain data is being retrieved by the CPU (whether internally or from an external source such as a program or configuration data updates from the Internet cloud) or when the user has stepped over the user display. If the electrodes are not ready for the user, flow proceeds from block 150 to block 152 to accommodate this delay.

Once the CPU determines that the electrodes are ready for use while the user is standing on the platform surface, flow proceeds to block 160. Stabilization of the user on the platform surface may be ascertained by injecting current through the electrodes via the interleaved arrangement thereof. Where such current is returned via other electrodes for a particular foot and/or foot size, and is consistent for a relatively brief period of time, for example, a few seconds, the CPU can assume that the user is standing still and ready to use the electrodes and related circuitry. At block 160, a decision is made that both the user and the platform apparatus are ready for measuring impedance and certain segments of the user's body, including at least one foot.

The remaining flow of FIG. 1f includes the application and sensing of current through the electrodes for finding the optimal electrodes (162) and for performing impedance measurements (block 164). These measurements are continued until completed at block 166 and all such useful measurements are recorded and are logged in the user profile memory for this specific user, at block 168. At block 172, the CPU generates output data to provide feedback as to the completion of the measurements and, as can be indicated as a request via the user profile for this user, as an overall report on the progress for the user and relative to previous measurements made for this user has stored in the user profile memory. Such feedback may be shown on the user display, through a speaker with co-located apertures in the platform for audible reception by the user, and/or by vibration circuitry which, upon vibration under control of the CPU, the user can sense through one or both feet while standing on the scale. From this output at block 172, flow returns to the low power mode as indicated at block 174 with the return to the beginning of the flow at the block 140.

Figure 2A:
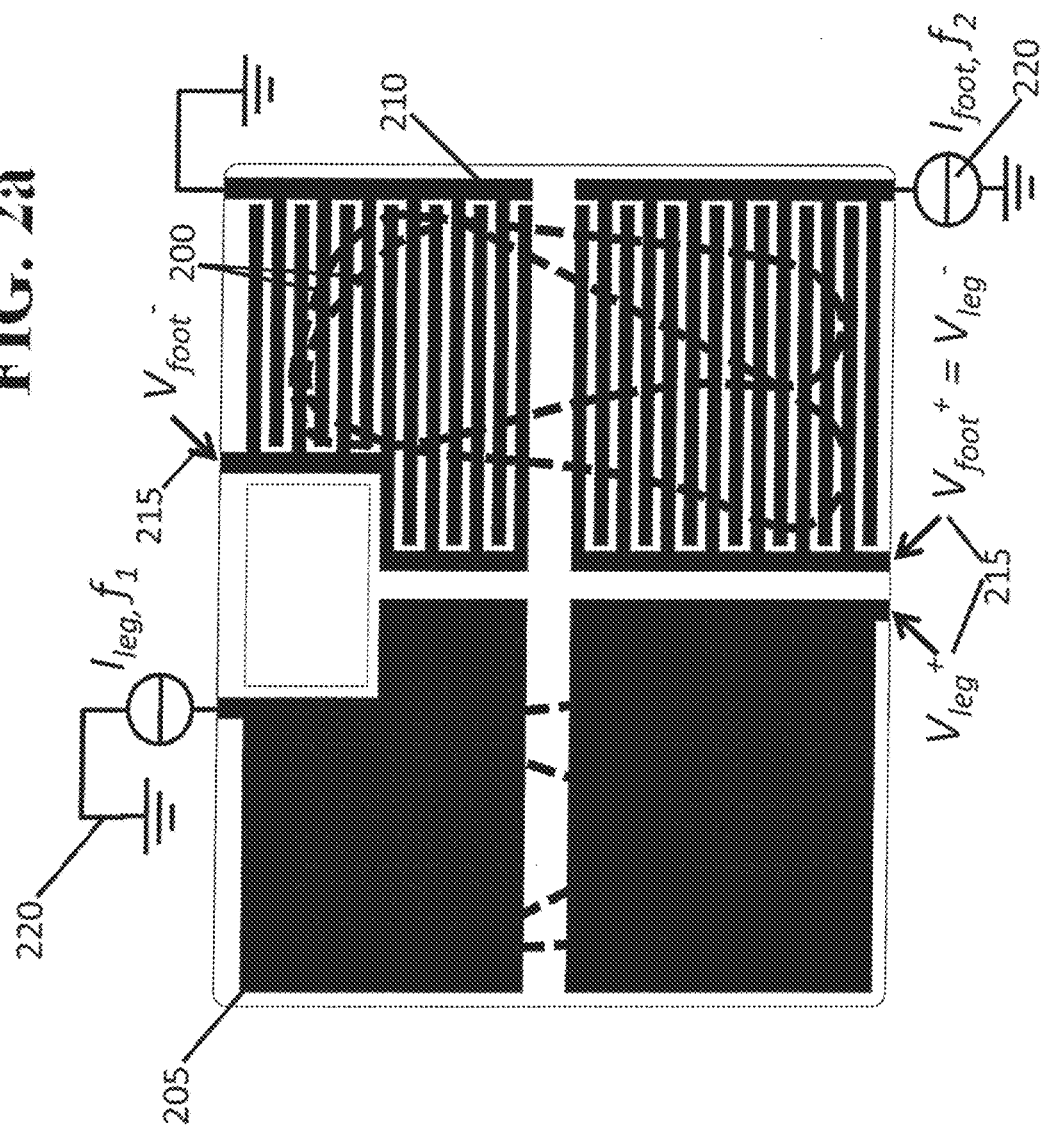
FIG. 2a shows an example of the insensitivity to foot placement on scale electrodes with multiple excitation and sensing current paths, consistent with various aspects of the present disclosure.

FIG. 2a shows an example of the insensitivity to foot placement 200 on scale electrode pairs 205/210 with multiple excitation paths 220 and sensing current paths 215, consistent with various aspects of the present disclosure. An aspect of the platform is that it has a thickness and strength to support a human adult of at least 200 pounds without fracturing, and another aspect of the device platform is comprised of at least six electrodes, where the first electrode pair 205 is solid and the second electrode pair 210 are interleaved. Another aspect is the first and second interleaved electrode pairs 205/210 are separated by a distance of at least 40+/−5 millimeters, where the nominal separation of less than 40 millimeters has been shown to degrade the single Foot IPG signal. Another key aspect is the electrode patterns are made from materials with low resistivity such as stainless steel, aluminum, hardened gold, ITO, index matched ITO (IMITO), carbon printed electrodes, conductive tapes, silver-impregnated carbon printed electrodes, conductive adhesives, and similar materials with resistivity lower than 300 ohms/sq. The resistivity can be below 150 ohms/sq. The electrodes are connected to the electronic circuitry in the scale by routing the electrodes around the edges of the scale to the surface below, or through at least one hole in the scale (e.g., a via hole).

Suitable electrode arrangements for dual Foot IPG measurements can be realized in other embodiments. In certain embodiments, the interleaved electrodes are patterned on the reverse side of a thin piece (e.g., less than 2 mm) of high-ion-exchange (HIE) glass, which is attached to a scale substrate and used in capacitive sensing mode. In certain embodiments, the interleaved electrodes are patterned onto a thin piece of paper or plastic which can be rolled up or folded for easy storage. In certain embodiments, the interleaved electrodes are integrated onto the surface of a tablet computer for portable IPG measurements. In certain embodiments, the interleaved electrodes are patterned onto a kapton substrate that is used as a flex circuit.

In certain embodiments, the scale area has a length of 10 inches with a width of eight inches for a miniature scale platform. Alternatively, the scale may be larger (up to 36 inches wide) for use in bariatric class scales.

Figure 3A:
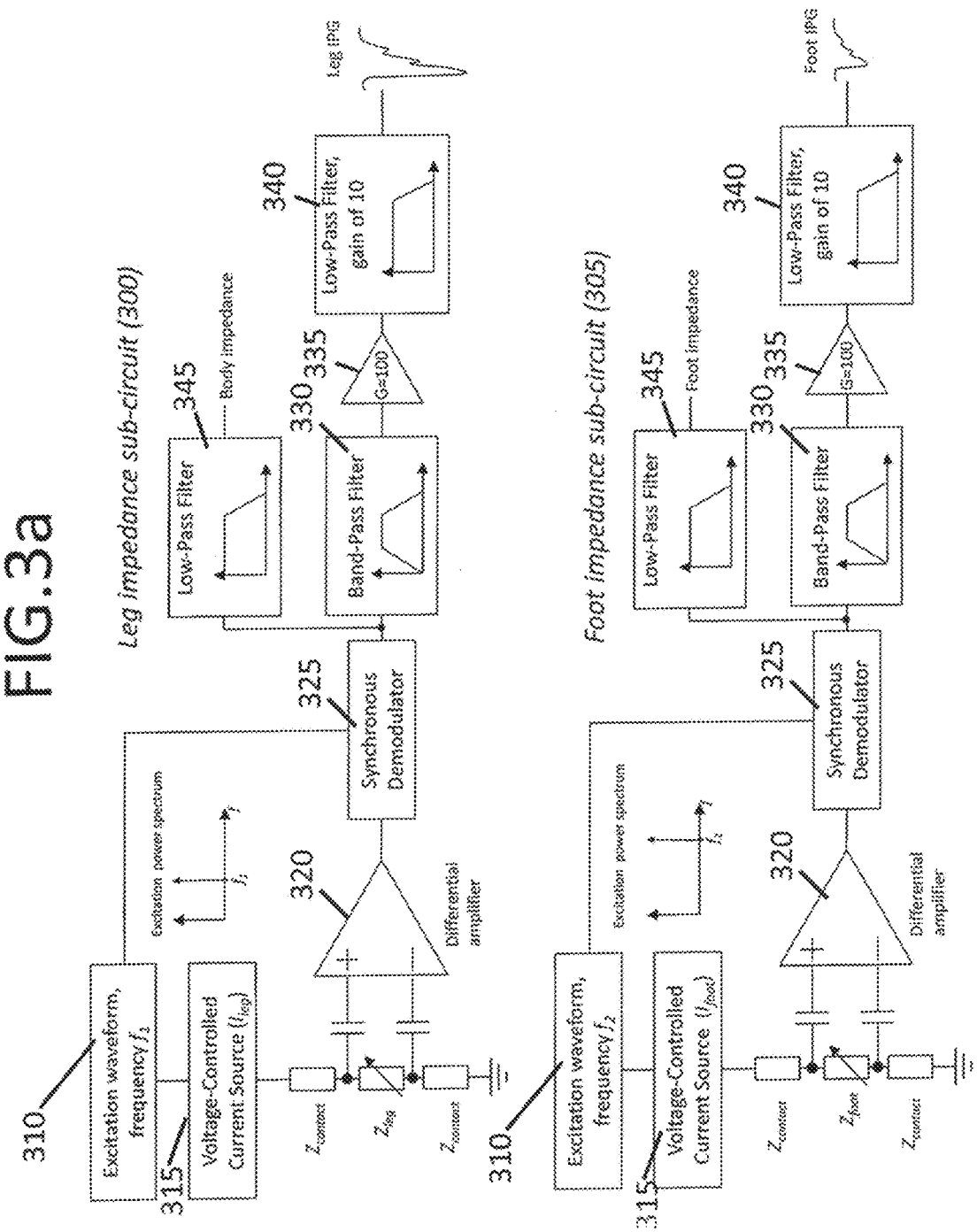
FIGS. 3a-3b show example block diagrams depicting circuitry for sensing and measuring the cardiovascular time-varying IPG raw signals and steps to obtain a filtered IPG waveform, consistent with various aspects of the present disclosure.

In the present disclosure, the leg and foot impedance measurements can be simultaneously carried out using a multi-frequency approach, in which the leg and foot impedances are excited by currents modulated at two or more different frequencies, and the resulting voltages are selectively measured using a synchronous demodulator as shown in FIG. 3a. This homodyning approach can be used to separate signals (in this case, the voltage drop due to the imposed current) with very high accuracy and selectivity.

This measurement configuration is based on a four-point configuration in order to minimize the impact of the contact resistance between the electrode and the foot, a practice well-known in the art of impedance measurement. In this configuration the current is injected from a set of two electrodes (the "injection" and "return" electrodes), and the voltage drop resulting from the passage of this current through the resistance is sensed by two separate electrodes (the "sense" electrodes), usually located in the path of the current. Since the sense electrodes are not carrying any current (by virtue of their connection to a high-impedance differential amplifier), the contact impedance does not significantly alter the sensed voltage.

In order to sense two distinct segments of the body (the legs and the foot), two separate current paths are defined by electrode positioning. Therefore two injection electrodes are used, each connected to a current source modulated at a different frequency. The injection electrode for leg impedance is located under the plantar region of the left foot, while the injection electrode for the Foot IPG is located under the heel of the right foot. Both current sources share the same return electrode located under the plantar region of the right foot. This is an illustrative example. Other configurations may be used.

The sensing electrodes can be localized so as to sense the corresponding segments. Leg IPG sensing electrodes are located under the heels of each foot, while the two foot sensing electrodes are located under the heel and plantar areas of the right foot. The inter-digitated nature of the right foot electrodes ensures a four-point contact for proper impedance measurement, irrespectively of the foot position, as already explained.

Figure 2B:
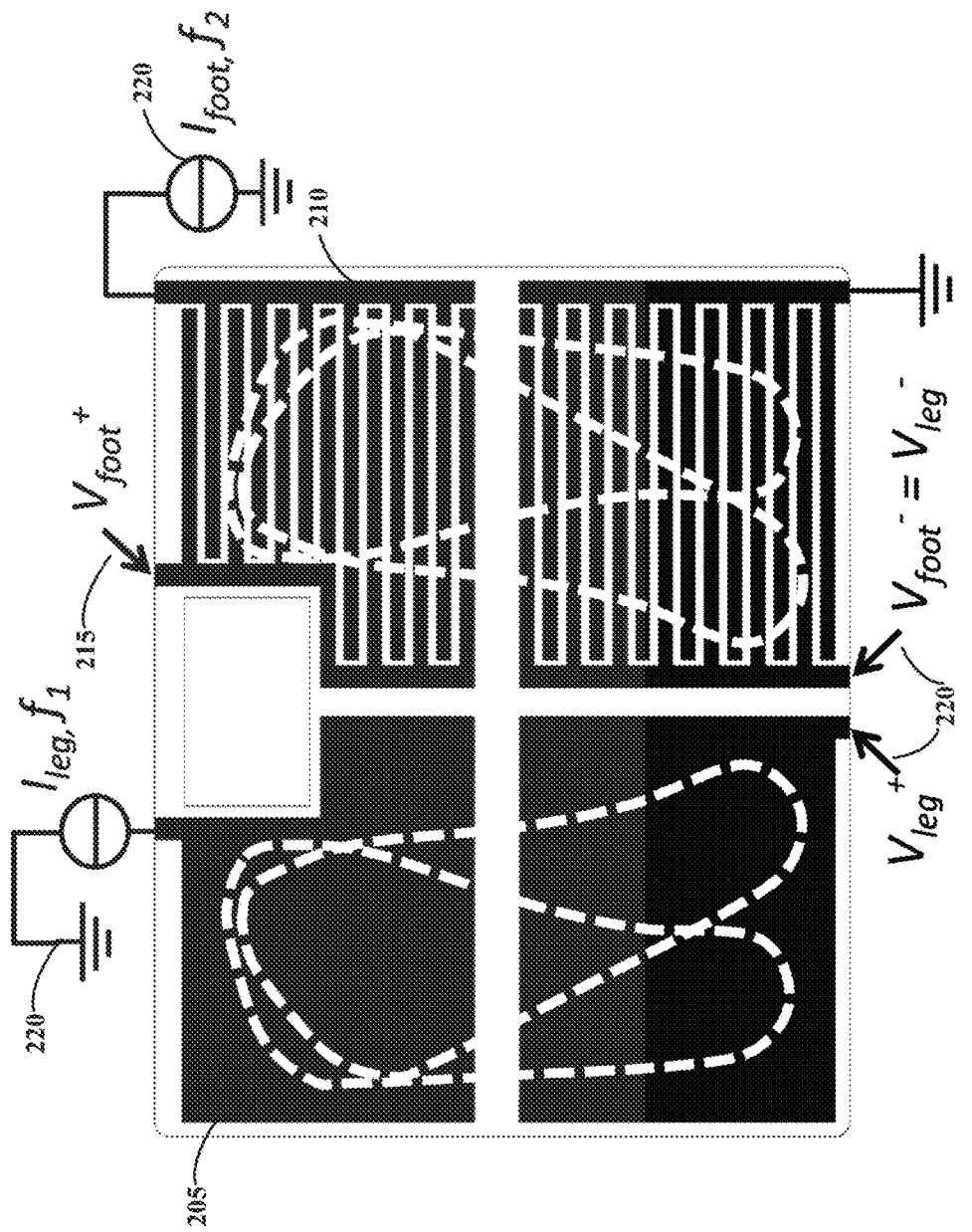
FIGS. 2b-2c show examples of electrode configurations, consistent with various aspects of the disclosure.

FIG. 2b shows an example of electrode configurations, consistent with various aspects of the disclosure. As shown by the electrode connections, in some embodiments, ground is coupled to the heel of one foot of the user (e.g., the right foot) and the foot current injection (e.g., excitation paths 220) is coupled to the toes of the respective one foot (e.g., toes of the right foot). The leg current injection is coupled to the toes of the other foot (e.g., toes of the left foot).

Figure 2C:
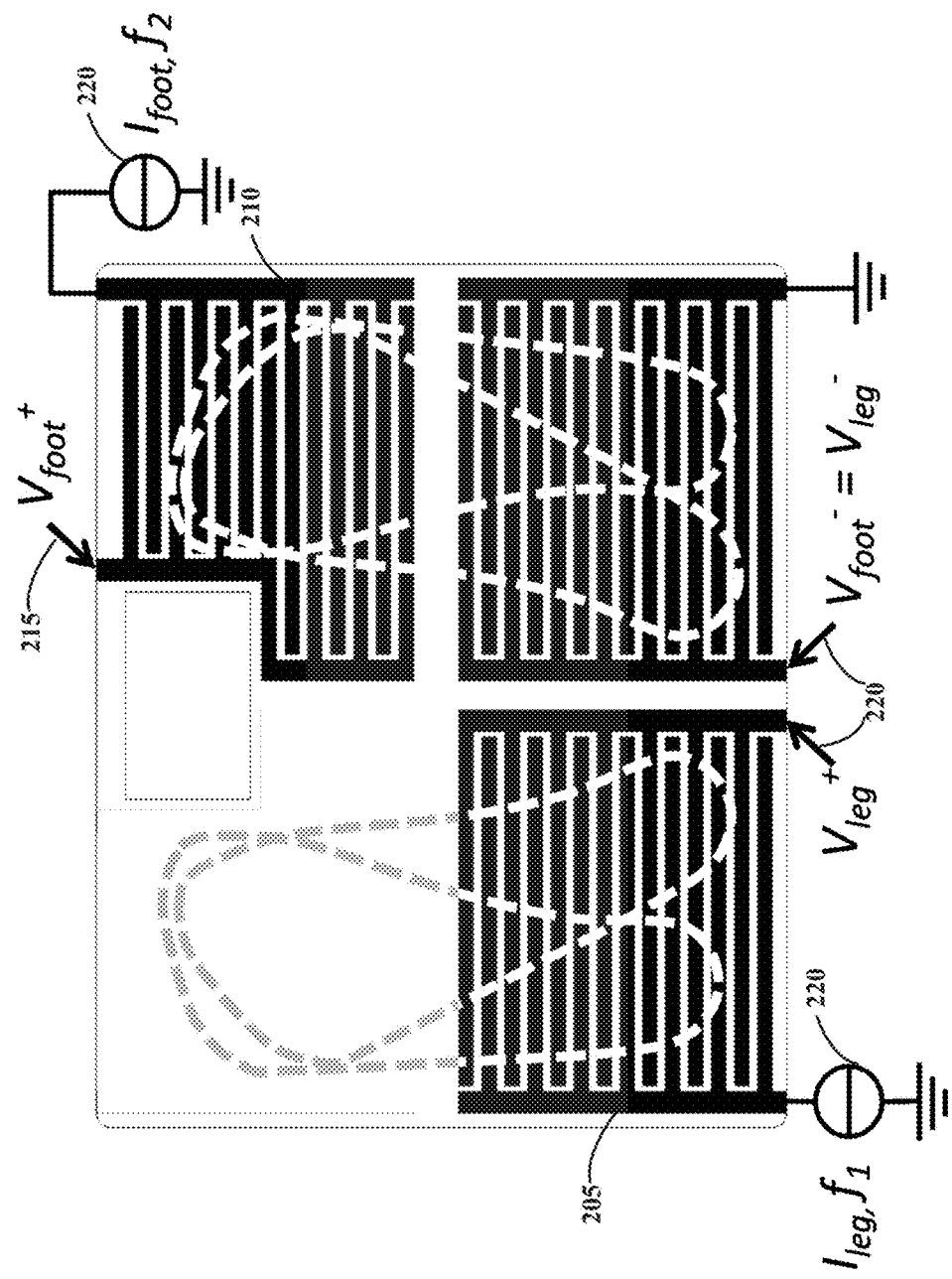

FIG. 2c shows an example of electrode configurations, consistent with various aspects of the disclosure. As shown by the electrode connections, in some embodiments, ground is coupled to the heel of one foot of the user (e.g., the right foot) and the foot current injection (e.g., excitation paths 220) is coupled to the toes of the one foot (e.g., toes of the right foot). The leg current injection is coupled to the heels of the other foot of the user (e.g., heels of the left foot).

Figure 3B:
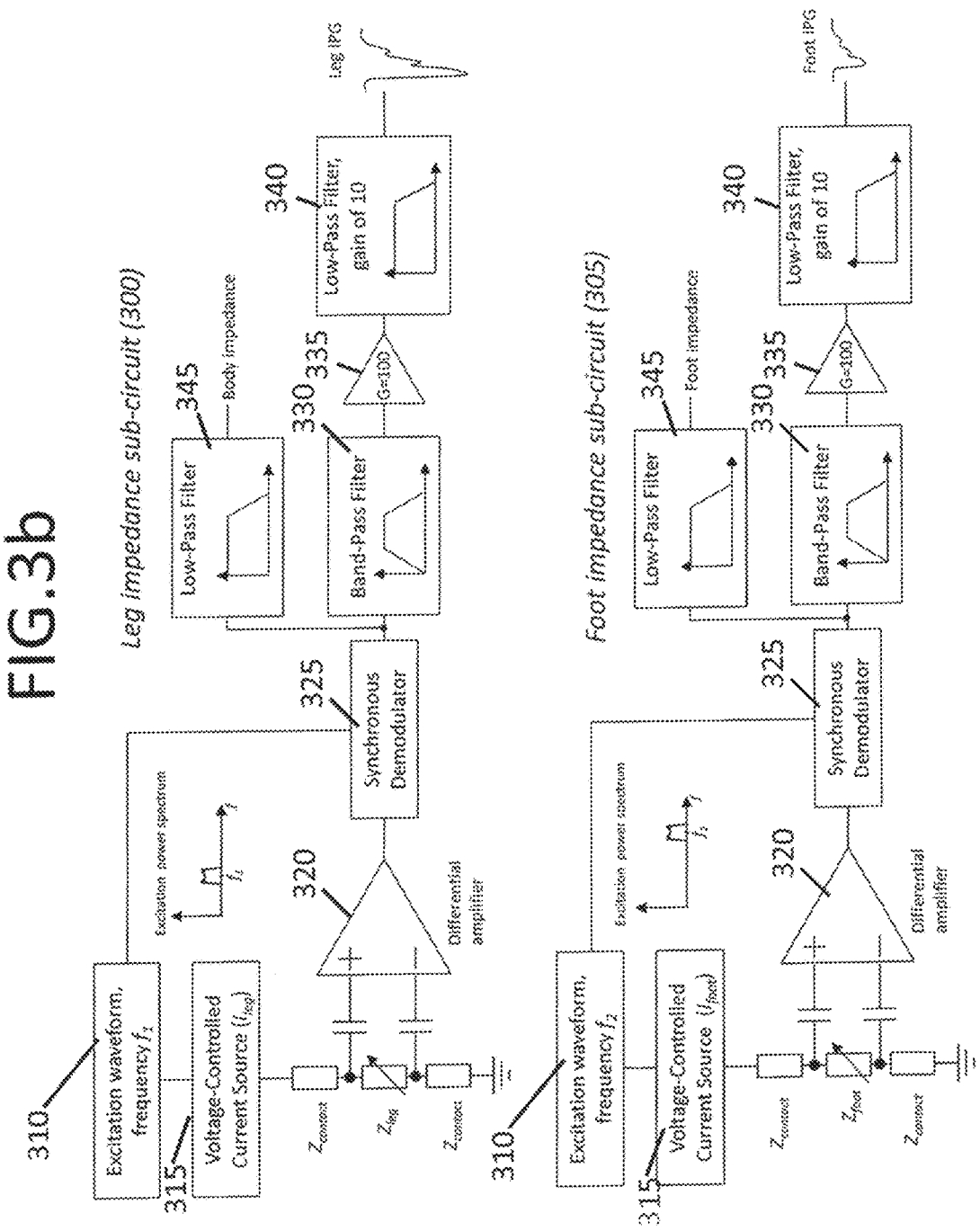

FIGS. 3a-3b show example block diagrams depicting the circuitry for sensing and measuring the cardiovascular time-varying IPG raw signals and steps to obtain a filtered IPG waveform, consistent with various aspects of the present disclosure. The example block diagrams shown in FIGS. 3a-3b are separated in to a leg impedance sub-circuit 300 and a foot impedance sub-circuit 305.

Excitation is provided by way of an excitation waveform circuit 310. The excitation waveform circuit 310 provides a stable amplitude excitation signal by way of various wave shapes of various, frequencies, such as more specifically, a sine wave signal (as is shown in FIG. 3a) or, more specifically, a square wave signal (as shown in FIG. 3b). This excitation waveform (of sine, square, or other wave shape) is fed to a voltage-controlled current source circuit 315 which scales the signal to the desired current amplitude. The generated current is passed through a decoupling capacitor (for safety) to the excitation electrode, and returned to ground through the return electrode (grounded-load configuration). Amplitudes of 1 and 4 mA peak-to-peak are typically used for Leg and Foot IPGs, respectively.

The voltage drop across the segment of interest (legs or foot) is sensed using an instrumentation differential amplifier (e.g., Analog Devices AD8421) 320. The sense electrodes on the scale are AC-coupled to the inputs of the differential amplifier 320 (configured for unity gain), and any residual DC offset is removed with a DC restoration circuit (as exemplified in Burr-Brown App Note Application Bulletin, SBOA003, 1991, or Burr-Brown/Texas Instruments INA118 datasheet). Alternatively, a fully differential input amplification stage can be used which eliminates the need for DC restoration.

The signal is then demodulated with a phase-sensitive synchronous demodulator circuit 325. The demodulation is achieved in this example by multiplying the signal by 1 or −1 synchronously in-phase with the current excitation. Such alternating gain is provided by an operational amplifier (op amp) and an analog switch (SPST), such as an ADG442 from Analog Devices). More specifically, the signal is connected to both positive and negative inputs through 10 kOhm resistors. The output is connected to the negative input with a 10 kOhm resistor as well, and the switch is connected between the ground and the positive input of the op amp. When open, the gain of the stage is unity. When closed (positive input grounded), the stage acts as an inverting amplifier with a gain of −1. Further, fully differential demodulators can alternatively be used which employ pairs of DPST analog switches whose configuration can provide the benefits of balanced signals and cancellation of charge injection artifacts. Alternatively, other demodulators such as analog multipliers or mixers can be used. The in-phase synchronous detection allows the demodulator to be sensitive to only the real, resistive component of the leg or foot impedance, thereby rejecting any imaginary, capacitive components which may arise from parasitic elements associated with the foot to electrode contacts.

Once demodulated, the signal is band-pass filtered (0.4-80 Hz) with a band-pass filter circuit 330 before being amplified with a gain of 100 with a non-inverting amplifier circuit 335 (e.g., using an LT1058 operational amplifier from Linear Technology Inc.). The amplified signal is further amplified by 10 and low-pass filtered (cut-off at 20 Hz) using a low-pass filter circuit 340 such as 2-pole Sallen-Key filter stage with gain. The signal is then ready for digitization and further processing. In certain embodiments, the signal from the demodulator circuit 325 can be passed through an additional low-pass filter circuit 345 to determine body or foot impedance.

In certain embodiments, the generation of the excitation voltage signal, of appropriate frequency and amplitude, is carried out by a microcontroller, such as an MSP430 (Texas Instruments, Inc.) or a PIC18Fxx series (Microchip Technology, Inc.). The voltage waveform can be generated using the on-chip timers and digital input/outputs or pulse width modulation (PWM) peripherals, and scaled down to the appropriate voltage through fixed resistive dividers, active attenuators/amplifiers using on-chip or off-chip operational amplifiers, as well as programmable gain amplifiers or programmable resistors. In certain embodiments, the generation of the excitation frequency signal can be accomplished by an independent quartz crystal oscillator whose output is frequency divided down by a series of toggle flip-flops (such as an ECS-100AC from ECS International, Inc., and a CD4024 from Texas Instruments, Inc.). In certain embodiments, the generation of the wave shape and frequency can be accomplished by a direct digital synthesis (DDS) integrated circuit (such as an AD9838 from Analog Devices, Inc.). In certain embodiments, the generation of the wave shape (either sine or square) and frequency can be accomplished by a voltage-controlled oscillator (VCO) which is controlled by a digital microcontroller, or which is part of a phase-locked loop (PLL) frequency control circuit. Alternatively, the waveforms and frequencies can be directly generated by on- or off-chip digital-to-analog converters (DACs).

In certain embodiments, the shape of the excitation is not square, but sinusoidal. Such configuration can reduce the requirements on bandwidth and slew rate for the current source and instrumentation amplifier. Harmonics, potentially leading to higher electromagnetic interference (EMI), can also be reduced. Such excitation may also reduce electronics noise on the circuit itself. Lastly, the lack of harmonics from sine wave excitation may provide a more flexible selection of frequencies in a multi-frequency impedance system, as excitation waveforms have fewer opportunities to interfere between each other. Due to the concentration of energy in the fundamental frequency, sine wave excitation could also be more power-efficient. In certain embodiments, the shape of the excitation is not square, but trapezoidal. Alternatively, raised cosine pulses (RCPs) could be used as the excitation wave shape, providing an intermediate between sine and square waves. RCPs could provide higher excitation energy content for a given amplitude, but with greatly reduced higher harmonics.

To further reduce potential electromagnetic interference (EMI), other strategies may be used, such as by dithering the square wave signal (i.e., introducing jitter in the edges following a fixed or random pattern) which leads to so-called spread spectrum signals, in which the energy is not localized at one specific frequency (or a set of harmonics), but rather distributed around a frequency (or a set of harmonics). Because of the synchronous demodulation scheme, phase-to-phase variability introduced by spread-spectrum techniques will not affect the impedance measurement. Such a spread-spectrum signal can be generated by, but not limited to, specialized circuits (e.g., Maxim MAX31C80, SiTime SiT9001), or generic microcontrollers (see Application Report SLAA291, Texas Instruments, Inc.). These spread-spectrum techniques can be combined with clock dividers to generate lower frequencies as well.

As may be clear to one skilled in the art, these methods of simultaneous measurement of impedance in the leg and foot can be used for standard Body Impedance Analysis (BIA), aiming at extracting the relative content of total water, free-water, fat mass and other body composition measures. Impedance measurements for BIA are typically done at frequencies ranging from kilohertz up to several megahertz. The multi-frequency synchronous detection measurement methods described above can readily be used for such BIA, provided that low-pass filtering (345, FIGS. 3a and 3b) instead of band-pass filtering (330, FIGS. 3a and 3b) is performed following the demodulation. In certain embodiments, a separate demodulator channel may be driven by the quadrature phase of the excitation signal to allow the imaginary component of the body impedance to be extracted in addition to the real component. A more accurate BIA can be achieved by measuring both the real and imaginary components of the impedance. This multi-frequency technique can be combined with traditional sequential measurements used for BIA, in which the impedance is measured at several frequencies sequentially. These measurements are repeated in several body segments for segmental BIAs, using a switch matrix to drive the current into the desired body segments.

While FIG. 2a shows a circuit and electrode configuration suitable to measure two different segments (legs and one foot), this approach is not readily extendable to more segments due to the shared current return electrode (ground). To overcome this limitation, and provide simultaneous measurements in both feet, the system can be augmented with analog switches to provide time-multiplexing of the impedance measurements in the different segments. This multiplexing can be a one-time sequencing (each segment is measured once), or interleaved at a high-enough frequency that the signal can be simultaneously measured on each segment. The minimum multiplexing rate for proper reconstruction is twice the bandwidth of the measured signal, based on signal processing theory (the Nyquist rate), which equals to about 100 Hz for the impedance signal considered here. The rate must also allow for the signal path to settle in between switching, which usually limits the maximum multiplexing rate. Referring to FIG. 14a, one cycle might start the measurement of the leg impedance and left foot impedances (similarly to previously described, sharing a common return electrode), but then follow with a measurement of the right foot after reconfiguring the switches. For specific information regarding typical switch configurations, reference to U.S. patent application Ser. No. 14/338,266 filed on Oct. 7, 2015 (now U.S. Pat. No. 10,130,273), which is fully incorporated for its specific and general teaching of switch configurations.

Since right and left feet are measured sequentially, one should note that a unique current source (at the same frequency) may be used to measure both, providing that the current source is not connected to the two feet simultaneously through the switches, in which case the current would be divided between two paths. One should also note that a fully-sequential measurement, using a single current source (at a single frequency) successively connected to the three different injection electrodes, could be used as well, with the proper switch configuration sequence (no splitting of the current path).

In certain embodiments, the measurement of various body segments, and in particular the legs, right foot and left foot, is achieved simultaneously due to as many floating current sources as segments to be measured, running at separate frequency so they can individually be demodulated. Such configuration is exemplified in FIG. 14b for three segments (legs, right and left feet). Such configuration has the advantage to provide true simultaneous measurements without the added complexity of time-multiplexing/demultiplexing, and associated switching circuitry. An example of such a floating current source is found in Plickett, et al., Physiological Measurement, 32 (2011). Another approach to floating current sources is the use of transformer-coupled current sources (as depicted in FIG. 14c). Using transformers to inject current into the electrodes enables the use of simpler, grounded-load current sources on the primary, while the electrodes are connected to the secondary. The transformer turns ratio can typically be 1:1, and since frequencies of interest for impedance measurement are typically in the 10-1000 kHz (occasionally 1 kHz for BIA), relatively small pulse transformers can be used. In order to limit the common mode voltage of the body, one of the electrodes in contact with the foot can be grounded.

While certain embodiments presented in the above specification have used current sources for excitation, the excitation can also be performed by a voltage source, where the resulting injection current is monitored by a current sense circuit so that impedance can still be derived by the ratio of the sensed voltage (on the sense electrodes) over the sensed current (injected in the excitation electrodes). It should be noted that broadband spectroscopy methods could also be used for measuring impedances at several frequencies. Combined with time-multiplexing and current switching described above, multi-segment broadband spectroscopy can be achieved.

Various aspects of the present disclosure are directed toward robust timing extraction of the blood pressure pulse in the foot which is achieved by means of a two-step processing. In a first step, the usually high-SNR Leg IPG is used to derive a reference (trigger) timing for each heart pulse. In a second step, a specific timing in the lower-SNR Foot IPG is extracted by detecting its associated feature within a restricted window of time around the timing of the Leg IPG.

Figure 3C:
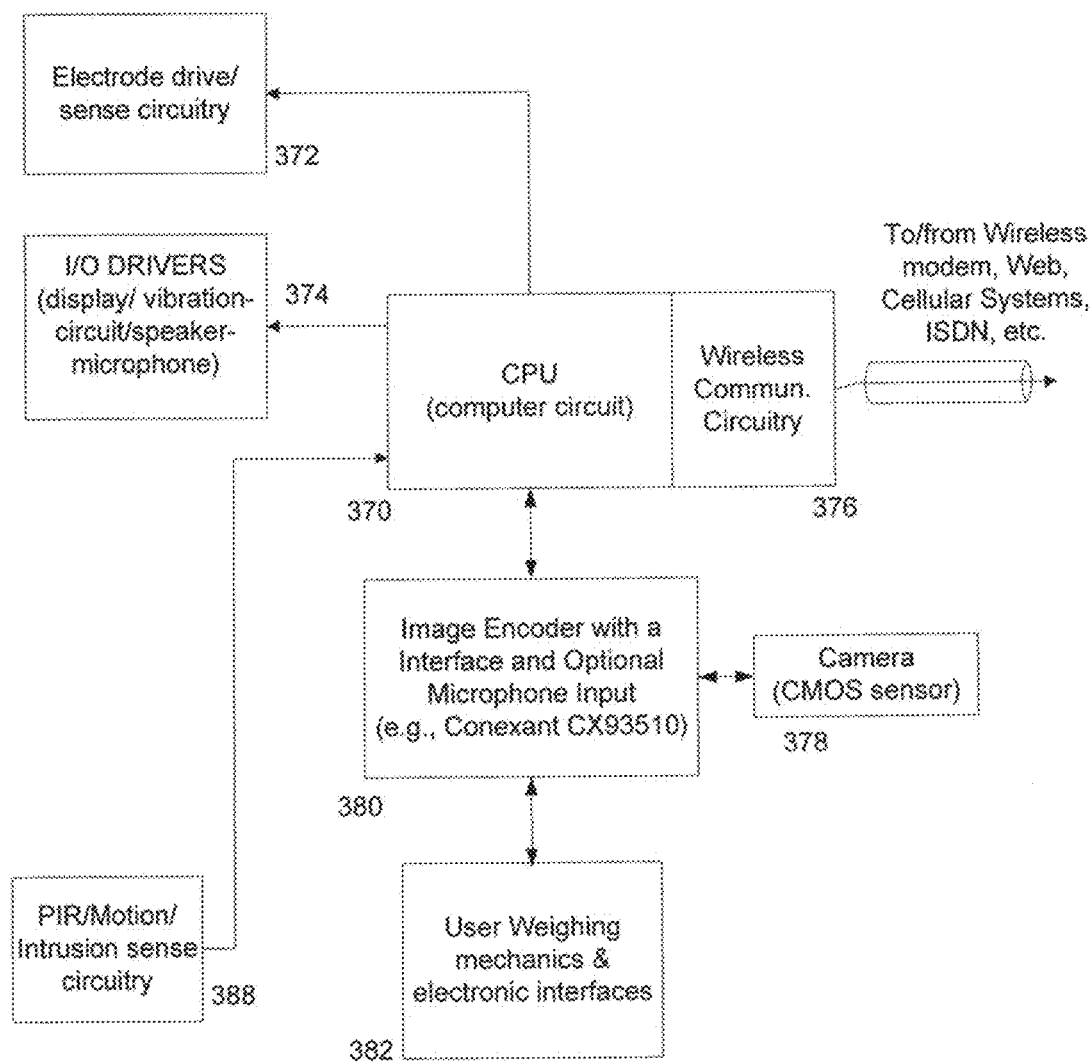
FIG. 3c depicts an example block diagram of circuitry for operating core circuits and modules, including for example those of FIGS. 3a-3b, used in various specific embodiments of the present disclosure.

Consistent with yet further embodiments of the present disclosure, FIG. 3c depicts an example block diagram of circuitry for operating core circuits and modules, including, for example, the operation of the CPU as in FIG. 1a with the related more specific circuit blocks/modules in FIGS. 3A-3B. As shown in the center of FIG. 3c, the computer circuit 370 is shown with other previously-mentioned circuitry in a generalized manner without showing some of the detailed circuitry (e.g., amplification and current injection/sensing (372)). The computer circuit 370 can be used as a control circuit with an internal memory circuit (or as integrated with the memory circuit for the user profile memory 146A of FIG. 1*a*) for causing, processing and/or receiving sensed input signals as at block 372. As discussed, these sensed signals can be responsive to injection current and/or these signals can be sensed by less complex grid-based sense circuitry surrounding the platform as is convention in capacitive touch-screen surfaces which, in certain embodiments, the platform includes.

As noted, the memory circuit can be used not only for the user profile memory, but also as to provide configuration and/or program code and/or other data such as user-specific data from another authorized source such as from a user monitoring his/her logged data and/or profile from a remote desk-top. The remote device or desk-top can communicate with and access such data via a wireless communication circuit 376. For example, the wireless communication circuit 376 provides an interface between an app on the user's cellular telephone/tablet and the apparatus, wherefrom the IPhone is the output/input interface for the platform (scale) apparatus including, for example, an output display, speaker and/or microphone, and vibration circuitry; each of these I/O aspects and components being discussed herein in connection with other example embodiments.

A camera 378 and image encoder circuit 380 (with compression and related features) can also be incorporated as an option. As discussed above, the weighing scale components, as in block 382, are also optionally included in the housing which encloses and/or surrounds the platform.

For long-lasting battery life in the platform apparatus (batteries not shown), at least the CPU 370, the wireless communication circuit 376, and other current draining circuits are inactive unless and until activated in response to the intrusion/sense circuitry 388. As shown, one specific implementation employs a Conexant chip (e.g., CX93510) to assist in the low-power operation. This type of circuitry is designed for motion sensors configured with a camera for visual verification and image and video monitoring applications (such as by supporting JPEG and MJPEG image compression and processing for both color and black and white images). When combined with an external CMOS sensor, the chip retrieves and stores compressed JPEG and audio data in an on-chip memory circuit (e.g., 256 KB/128 KB frame buffer) to alleviate the necessity of external memory. The chip uses a simple register set via the microprocessor interface and allows for wide flexibility in terms of compatible operation with another microprocessor.

In one specific embodiment, a method of using the platform with the plurality of electrodes are concurrently contacting a limb of the user, includes operating such to automatically obtain measurement signals from the plurality of electrodes. As noted above, these measurement signals might initially be through less complex (e.g., capacitive grid-type) sense circuitry. Before or while obtaining a plurality of measurement signals by operating the circuitry, the signal-sense circuitry 388 is used to sense wireless-signals indicative of the user approaching the platform and, in response, causing the CPU circuitry 370 to transition from a reduced power-consumption mode of operation and at least one higher power-consumption mode of operation. After the circuitry is operating in the higher power-consumption mode of operation, the CPU accesses the user-corresponding data stored in the memory circuit and causes a plurality of impedance-measurement signals to be obtained by using the plurality of electrodes while they are contacting the user via the platform; therefrom, the CPU generates signals corresponding to cardiovascular timings of the user.

The signal-sense circuit can be employed as a passive infrared detector and with the CPU programmed (as a separate module) to evaluate whether radiation from the passive infrared detector is indicative of a human. For example, sensed levels of radiation that corresponds to a live being, such as a dog, that is less than a three-foot height, and/or has not moved for more than a couple seconds, can be assessed as being a non-human.

Accordingly, as the user is recognized as being human, the CPU is activated and begins to attempt the discernment process of which user might be approaching. This is performed by the CPU accessing the user-corresponding data stored in the memory circuit (the user profile memory). If the user is recognized based on parameters such as discussed above (e.g., time of morning, speed of approach, etc.), the CPU can also select one of a plurality of different types of user-discernible visual/audible/tactile information and for presenting the discerned user with visual/audible/tactile information that was retrieved from the memory as being specific to the user. For example, user-selected visual/audible data can be outputted for the user. Also, responsive to the motion detection indication, the camera can be activated to capture at least one image of the user while the user is approaching the platform (and/or while the user is on the platform to log confirmation of the same user with the measured impedance information). As shown in block 374 of FIG. 3*c*, where a speaker is also integrated with the CPU, the user can simply command the platform apparatus to start the process and activation proceeds. As previously discussed, the scale can include voice input/output circuitry to receive the user commands via voice commands.

In another method, the circuitry of FIG. 3*c* is used with the electrodes being interleaved and engaging the user, as a combination weighing scale (via block 382) and a physiologic user-specific impedance-measurement device. By using the impedance-measurement signals and obtaining at least two impedance-measurement signals between one foot of the user and another location of the user, the interleaved electrodes assist the CPU in providing measurement results that indicate one or more of the following user-specific attributes as being indicative or common to the user: foot impedance, foot length, and type of arch, and wherein one or more of the user-specific attributes are accessed in the memory circuit and identified as being specific to the user. This information can be later retrieved by the user, medical and/or security personnel, according to a data-access authorization protocol as might be established upon initial configuration for the user.

Figure 3D:
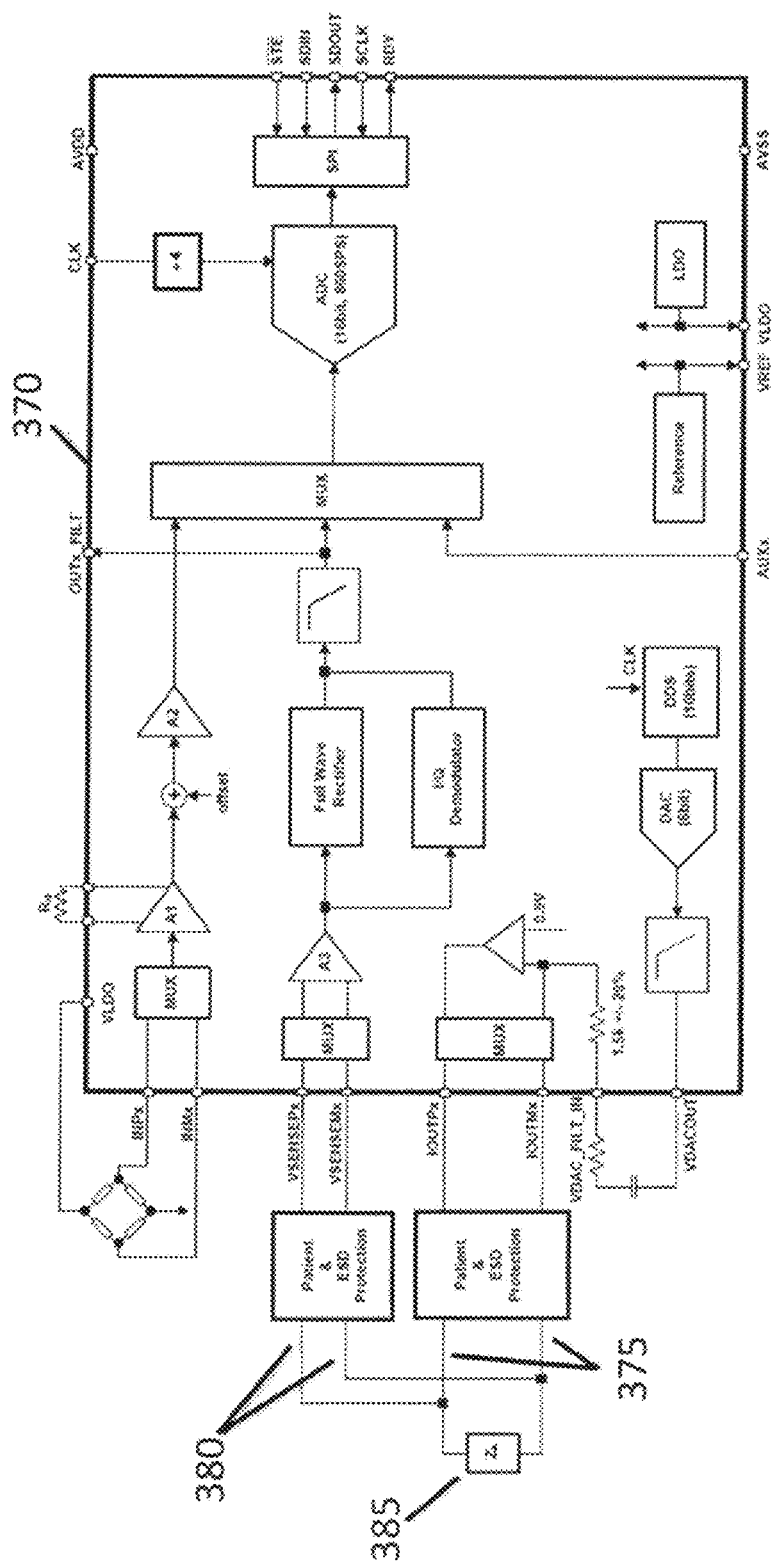
FIG. 3d shows an exemplary block diagram depicting the circuitry for interpreting signals received from electrodes.

FIG. 3*d* shows an exemplary block diagram depicting the circuitry for interpreting signals received from electrodes (e.g., 372 of FIG. 3*c*), and/or CPU 370 of FIG. 3*c*. The input electrodes 375 transmit electrical signals through the patient's body (depending on the desired biometric and physiological test to be conducted) and output electrodes 380 receive the modified signal as affected by a user's electrical impedance 385. Once received by the output electrodes 380, the modified signal is processed by processor circuitry 370 based on the selected test. Signal processing conducted by the processor circuitry 370 is discussed in more detail above (with regard to FIGS. 3*a-b*). In certain embodiments of the present disclosure, the circuitry within 370 is provided by Texas Instruments part # AFE4300.

FIG. 4 shows an example block diagram depicting signal processing steps to obtain fiducial references from the individual Leg IPG "beats," which are subsequently used to obtain fiducials in the Foot IPG, consistent with various aspects of the present disclosure. In the first step, as shown in block 400, the Leg IP and the Foot IPG are simultaneously measured. As shown at 405, the Leg IPG is low-pass filtered at 20 Hz with an 8-pole Butterworth filter, and inverted so that pulses have an upward peak. The location of the pulses is then determined by taking the derivative of this signal, integrating over a 100 ms moving window, zeroing the negative values, removing the large artifacts by zeroing values beyond 15× the median of the signal, zeroing the values below a threshold defined by the mean of the signal, and then searching for local maxima. Local maxima closer than a defined refractory period of 300 ms to the preceding ones are dismissed. The result is a time series of pulse reference timings.

As is shown in 410, the foot IPG is low-pass filtered at 25 Hz with an 8-pole Butterworth filter and inverted (so that pulses have an upward peak). Segments starting from the timings extracted (415) from the Leg IPG (reference timings) and extending to 80% of the previous pulse interval, but no longer than one second, are defined in the Foot IPG. This defines the time windows where the Foot IPG is expected to occur, avoiding misdetection outside of these windows. In each segment, the derivative of the signal is computed, and the point of maximum positive derivative (maximum acceleration) is extracted. The foot of the IPG signal is then computed using an intersecting tangent method, where the fiducial (420) is defined by the intersection between a first tangent to the IPG at the point of maximum positive derivative and a second tangent to the minimum of the IPG on the left of the maximum positive derivative within the segment.

The time series resulting from this two-step extraction is used with another signal to facilitate further processing. These timings are used as reference timings to improve the SNR of BCG signals to extract intervals between a timing of the BCG (typically the I-wave) and the Foot IPG for the purpose of computing the PWV, as previously disclosed in U.S. 2013/0310700 (Wiard). In certain embodiments, the timings of the Leg IPG are used as reference timings to improve the SNR of BCG signals, and the foot IPG timings are used to extract intervals between timing fiducials of the improved BCG (typically the I-wave) and the Foot IPG for the purpose of computing the PTT and the (PWV).

In certain embodiments, the processing steps include an individual pulse SNR computation after individual timings are extracted, either in Leg IPG or Foot IPG. Following the computation of the SNRs, pulses with a SNR below a threshold value are eliminated from the time series, to prevent propagating noise. The individual SNRs may be computed in a variety of methods known to one skilled in the art. For instance, an estimated pulse can be computed by ensemble averaging segments of signal around the pulse reference timing. The noise associated with each pulse is defined as the difference between the pulse and the estimated pulse. The SNR is the ratio of the root-mean-square (RMS) value of the estimated pulse over the RMS value of the noise for that pulse.

In certain embodiments, the time interval between the Leg IPG pulses, and the Foot IPG pulses, also detected by the above-mentioned methods, is extracted. The Leg IPG measuring a pulse occurring earlier in the legs compared to the pulse from the Foot IPG, the interval between these two is related to the propagation speed in the lower body, i.e., the peripheral vasculature. This provides complementary information to the interval extracted between the BCG and the Foot IPG for instance, and is used to decouple central versus peripheral vascular properties. It is also complementary to information derived from timings between the BCG and the Leg ICG.

Figure 5:
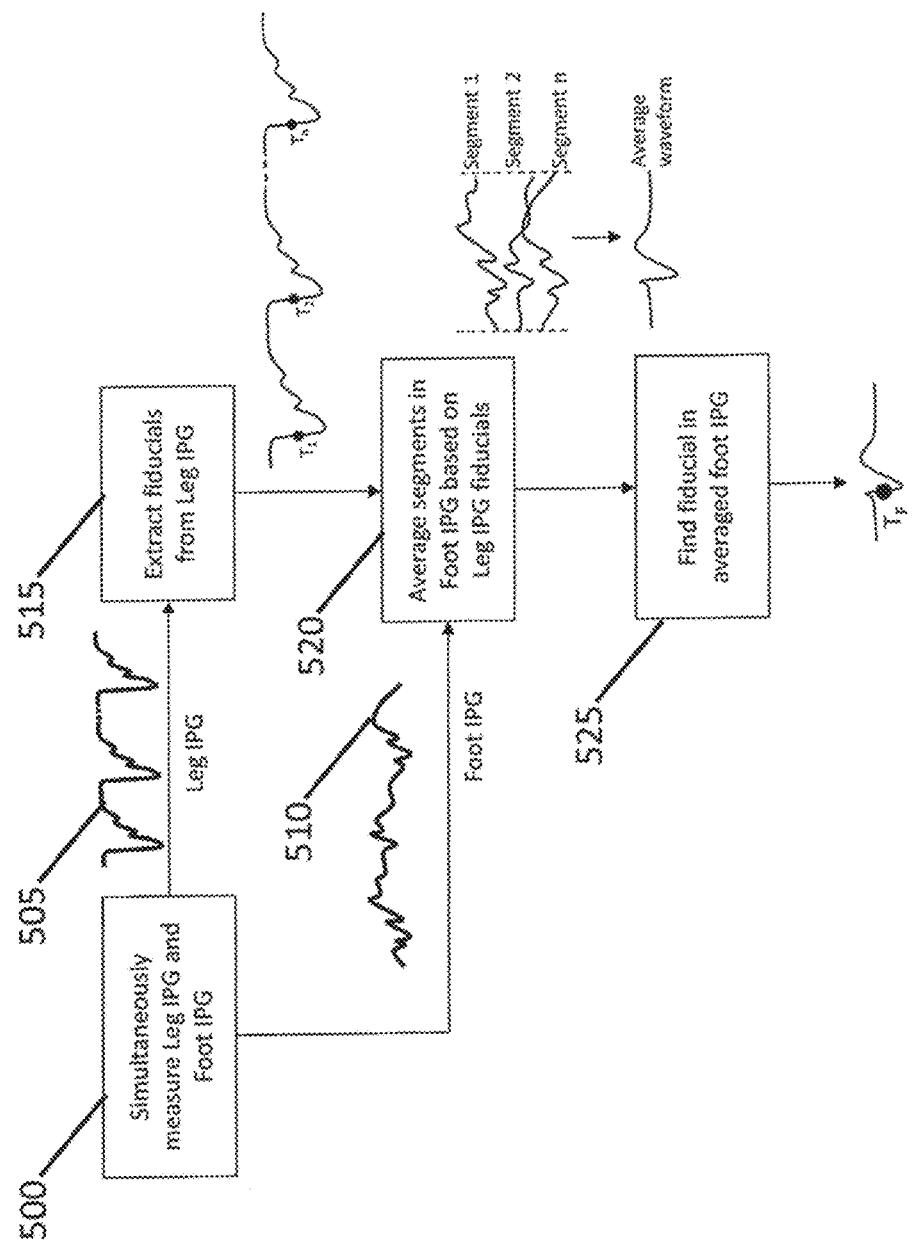
FIG. 5 shows an example flowchart depicting signal processing to segment individual Foot IPG "beats" to produce an averaged IPG waveform of improved SNR, which is subsequently used to determine the fiducial of the averaged Foot IPG, consistent with various aspects of the present disclosure.
Figure 7:
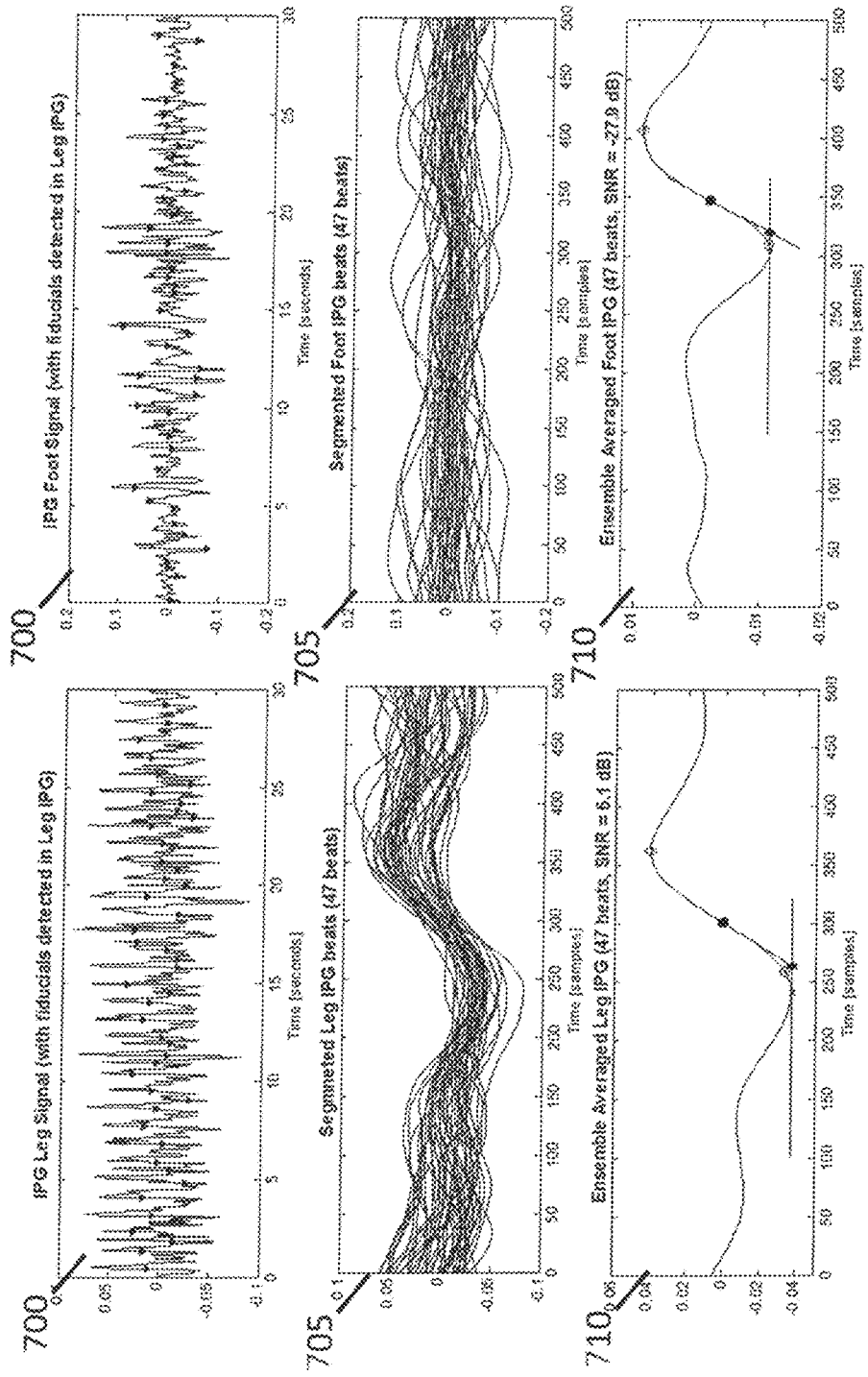
FIG. 7a shows examples of the Leg IPG signal with fiducials; the segmented Leg IPG into beats; and the ensemble averaged Leg IPG beat with fiducials and calculated SNR, for an exemplary low-quality recording, consistent with various aspects of the present disclosure.
FIG. 7b shows examples of the Foot IPG signal with fiducials derived from the Leg IPG fiducials; the segmented Foot IPG into beats; and the ensemble-averaged Foot IPG beat with fiducials and calculated SNR, for an exemplary low-quality recording, consistent with various aspects of the present disclosure.

FIG. 5 shows an example flowchart depicting signal processing to segment individual Foot IPG "beats" to produce an averaged IPG waveform of improved SNR, which is subsequently used to determine the fiducial of the averaged Foot IPG, consistent with various aspects of the present disclosure. Similar to the method shown in FIG. 4, the Leg IP and the Foot IPG are simultaneously measured (500), the Leg IPG is low-pass filtered (505), the foot IPG is low-pass filtered (510), and segments starting from the timings extracted (515) from the Leg IPG (reference timings). The segments of the Foot IPG extracted based on the Leg IPG timings are ensemble-averaged (520) to produce a higher SNR Foot IPG pulse. From this ensemble-averaged signal, the start of the pulse is extracted using the same intersecting tangent approach as described earlier. This approach enables the extraction of accurate timings in the Foot IPG even if the impedance signal is dominated by noise, as shown in FIG. 7b. These timings are used together with timings extracted from the BCG for the purpose of computing the PTT and (PWV). Timings derived from ensemble-averaged waveforms and individual waveforms can also be both extracted, for the purpose of comparison, averaging and error-detection.

Specific timings extracted from the IPG pulses (from either leg or foot) are related (but not limited) to the peak of the pulse, the minimum preceding the peak, or the maximum second derivative (maximum rate of acceleration) preceding the point of maximum derivative. An IPG pulse and the extraction of a fiducial (525) in the IPG can be performed by other signal processing methods, including (but not limited to) template matching, cross-correlation, wavelet-decomposition, or short window Fourier transform.

Figure 6:
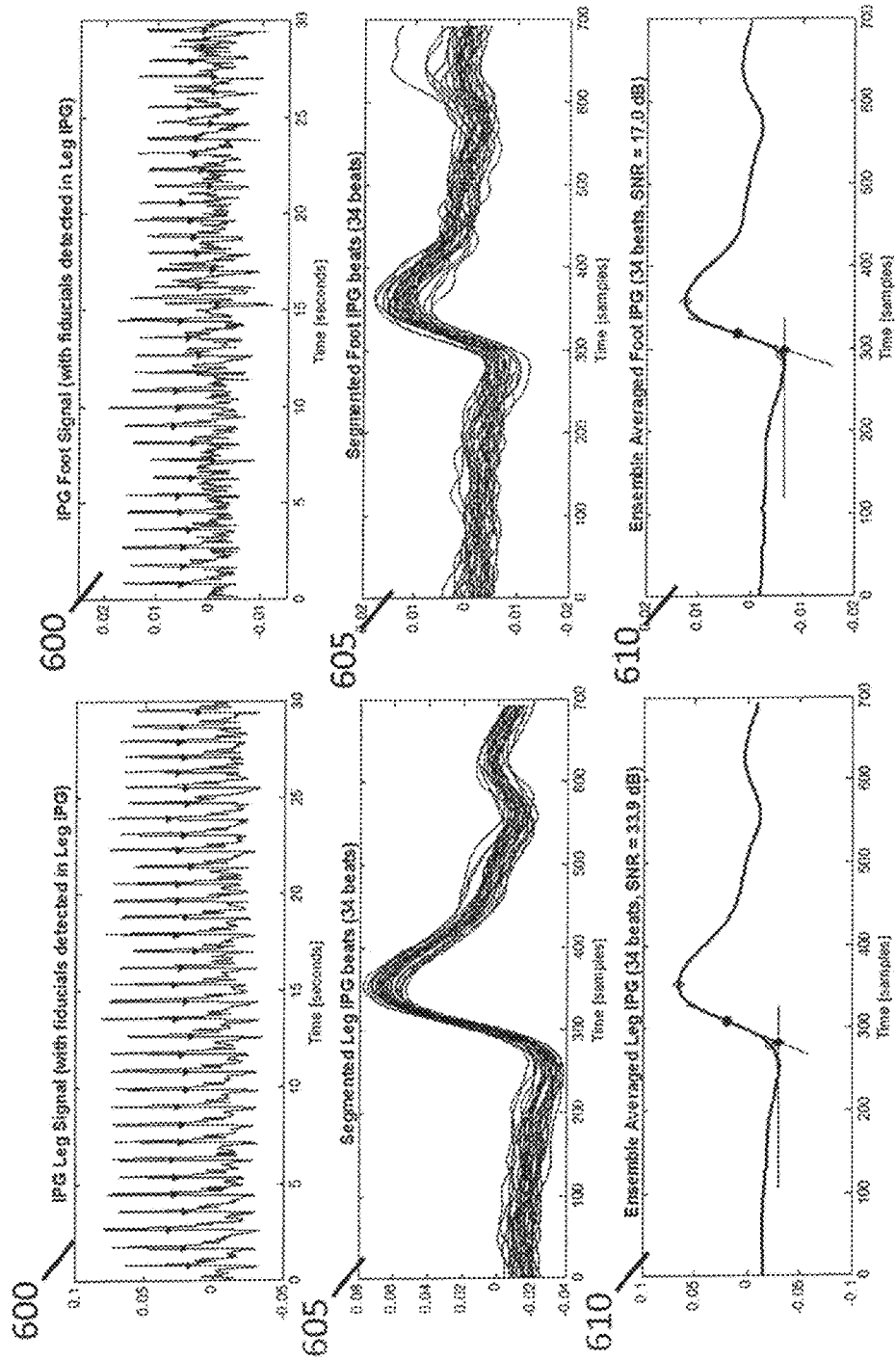
FIG. 6a shows examples of the Leg IPG signal with fiducials; the segmented Leg IPG into beats; and the ensemble-averaged Leg IPG beat with fiducials and calculated SNR, for an exemplary high-quality recording, consistent with various aspects of the present disclosure.
FIG. 6b shows examples of the Foot IPG signal with fiducials derived from the Leg IPG fiducials; the segmented Foot IPG into beats; and the ensemble-averaged Foot IPG beat with fiducials and calculated SNR, for an exemplary high-quality recording, consistent with various aspects of the present disclosure.

FIG. 6a shows examples of the Leg IPG signal with fiducials (plot 600); the segmented Leg IPG into beats (plot 605); and the ensemble-averaged Leg IPG beat with fiducials and calculated SNR (plot 610), for an exemplary high-quality recording, consistent with various aspects of the present disclosure.

FIG. 6b shows examples of the Foot IPG signal with fiducials derived from the Leg IPG fiducials (plot 600); the segmented Foot IPG into beats (plot 605); and the ensemble-averaged Foot IPG beat with fiducials and calculated SNR (plot 610), for an exemplary high-quality recording, consistent with various aspects of the present disclosure.

FIG. 7a shows examples of the Leg IPG signal with fiducials (plot 700); the segmented Leg IPG into beats (plot 705); and the ensemble averaged Leg IPG beat with fiducials and calculated SNR (plot 710), for an exemplary low-quality recording, consistent with various aspects of the present disclosure.

FIG. 7b shows examples of the Foot IPG signal with fiducials derived from the Leg IPG fiducials (plot 700); the segmented Foot IPG into beats (plot 705); and the ensemble-averaged Foot IPG beat with fiducials and calculated SNR (plot 710), for an exemplary low-quality recording, consistent with aspects of the present disclosure.

Figure 8:
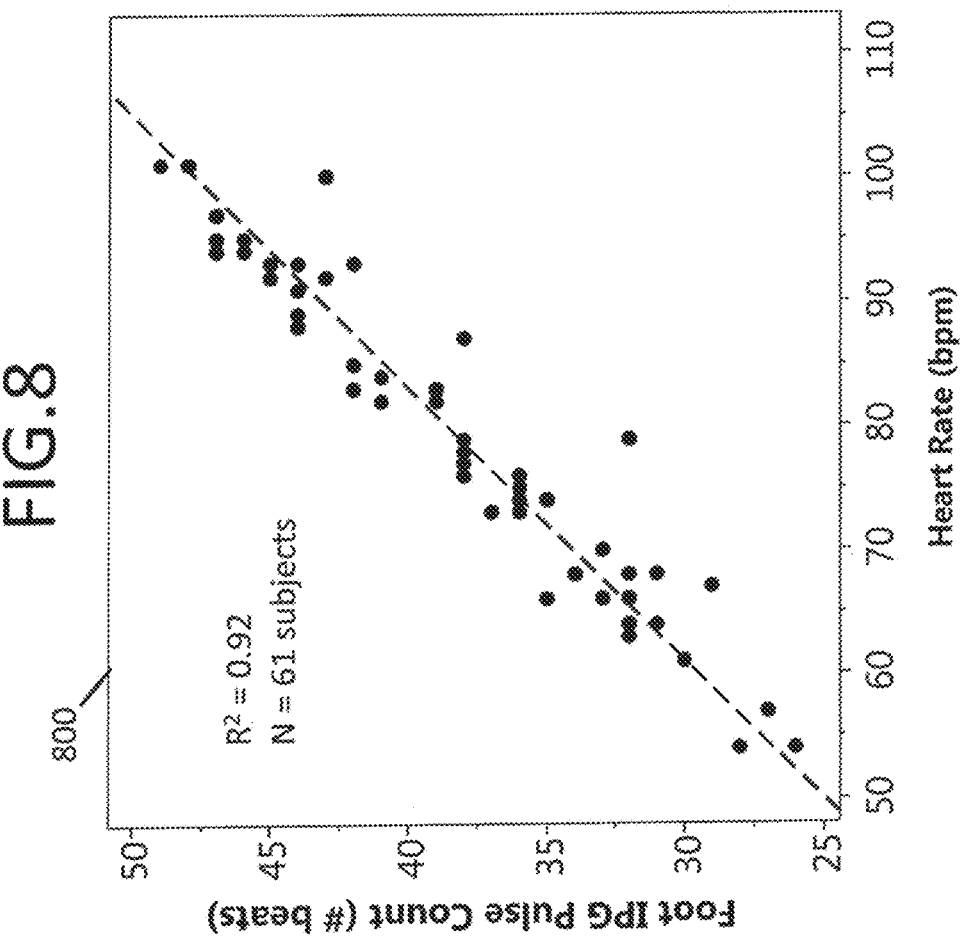
FIG. 8 shows an example correlation plot for the reliability in obtaining the low SNR Foot IPG pulse for a 30-second recording, using the first impedance signal as the trigger pulse, from a study including 61 test subjects with various heart rates, consistent with various aspects of the present disclosure.

FIG. 8 shows an example correlation plot 800 for the reliability in obtaining the low SNR Foot IPG pulse for a 30-second recording, using the first impedance signal as the trigger pulse, from a study including 61 test subjects with various heart rates, consistent with various aspects of the present disclosure.

In certain embodiments, a dual-Foot IPG is measured, allowing the detection of blood pressure pulses in both feet.

Such information can be used for diagnostic of peripheral arterial diseases (PAD) by comparing the relative PATs in both feet to look for asymmetries. It can also increase the robustness of the measurement by allowing one foot to have poor contact with electrodes (or no contact at all). SNR measurements can be used to assess the quality of the signal in each foot, and to select the best one for downstream analysis. Timings extracted from each foot can be compared and set to flag potentially inaccurate PWV measurements due to arterial peripheral disease, in the event these timings are different by more than a threshold. Alternatively, timings from both feet are pooled to increase the overall SNR if their difference is below the threshold.

In certain embodiments, the disclosure is used to measure a PWV, where the IPG is augmented by the addition of BCG sensing into the weighing scale to determine characteristic fiducials between the BCG and Leg IPG trigger, or the BCG and Foot IPG. The BCG sensors are comprised typically of the same strain gage set used to determine the bodyweight of the user. The load cells are typically wired into a bridge configuration to create a sensitive resistance change with small displacements due to the ejection of the blood into the aorta, where the circulatory or cardiovascular force produce movements within the body on the nominal order of 1-3 Newtons. BCG forces can be greater than or less than the nominal range in cases such as high or low cardiac output.

Figure 9A:
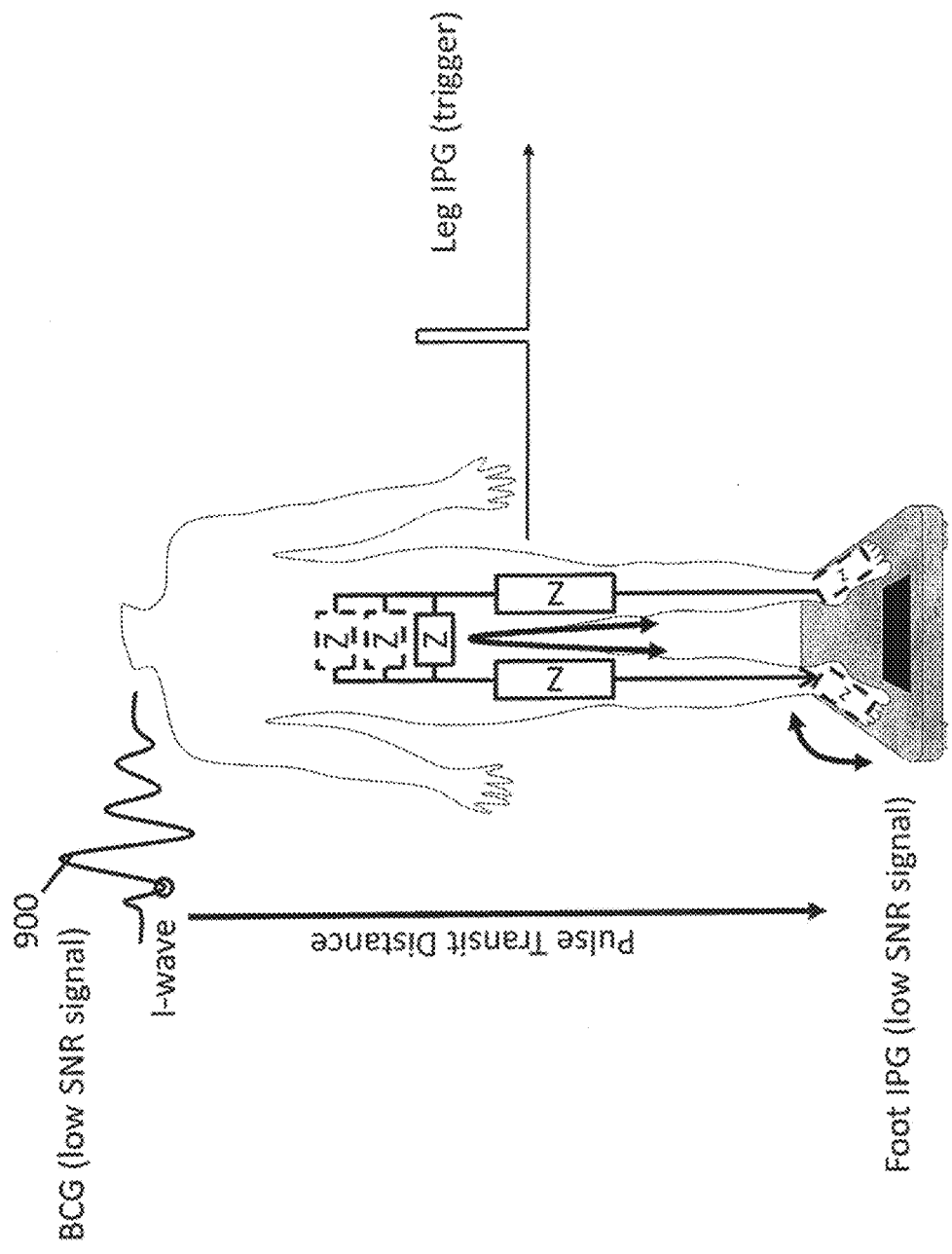
FIGS. 9a-b show an example configuration to obtain the pulse transit time (PTT), using the first IPG as the triggering pulse for the Foot IPG and ballistocardiogram (BCG), consistent with various aspects of the present disclosure.
Figure 9B:
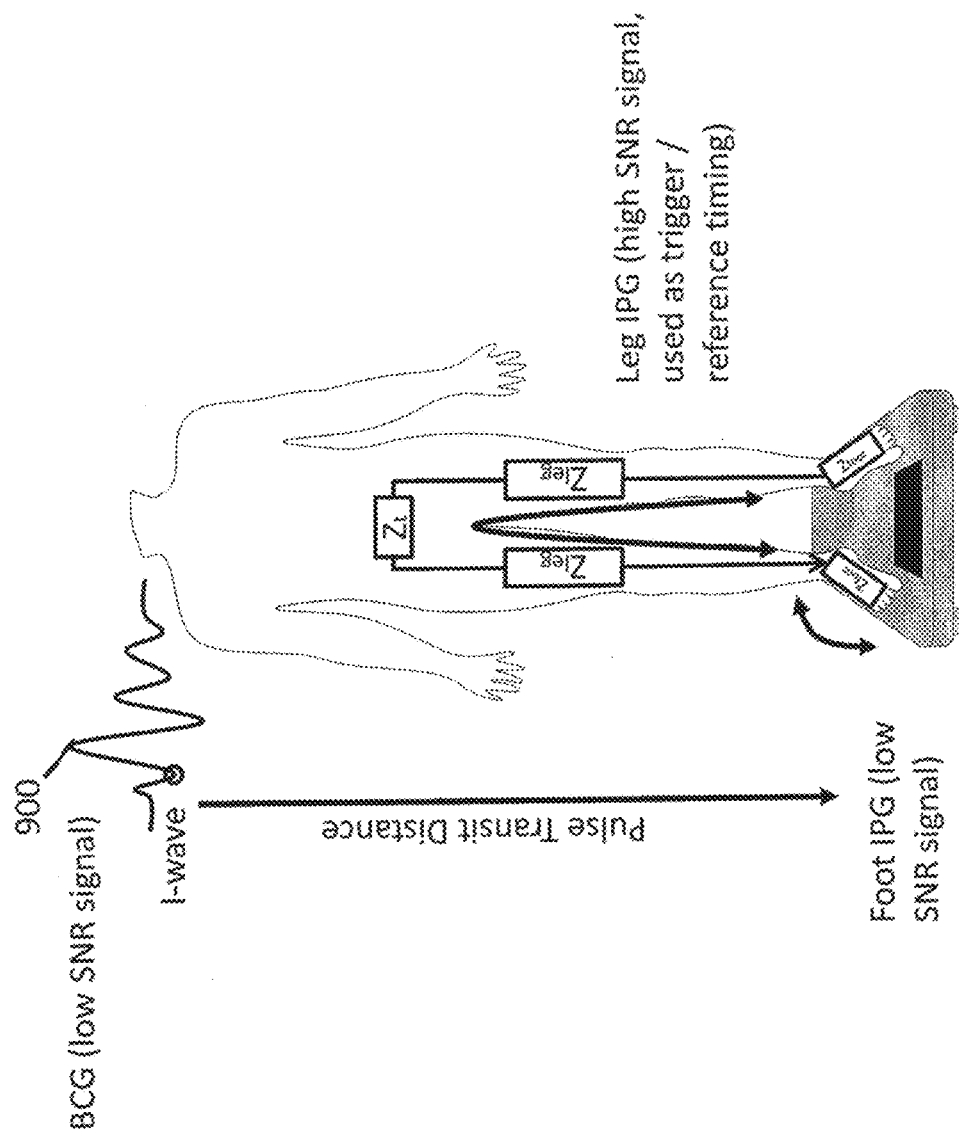

FIGS. 9*a-b* show example configurations to obtain the PTT, using the first IPG as the triggering pulse for the Foot IPG and BCG, consistent with various aspects of the present disclosure. The I-wave of the BCG 900 normally depicts the headward force due to cardiac ejection of blood into the ascending aorta which is used as a timing fiducial indicative of the pressure pulse initiation of the user's proximal aorta relative to the user's heart. The J-wave is indicative of timings in the systole phase and also incorporates information related to the strength of cardiac ejection and the ejection duration. The K-Wave provides systolic and vascular information of the user's aorta. The characteristic timings of these and other BCG waves are used as fiducials that can be related to fiducials of the IPG signals of the present disclosure.

Figure 10:
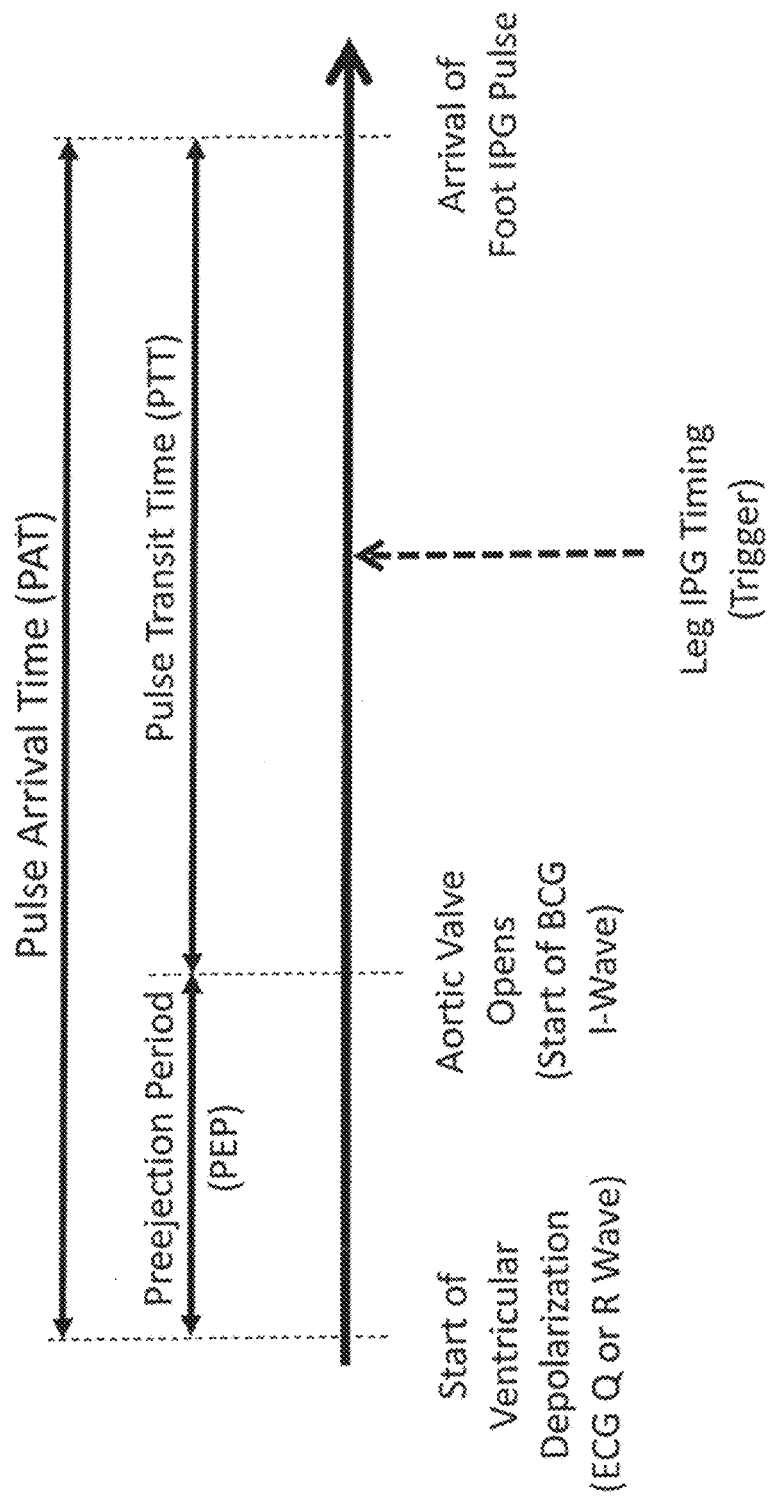
FIG. 10 shows nomenclature and relationships of various cardiovascular timings, consistent with various aspects of the present disclosure.

FIG. 10 shows nomenclature and relationships of various cardiovascular timings, consistent with various aspects of the present disclosure.

Figure 11:
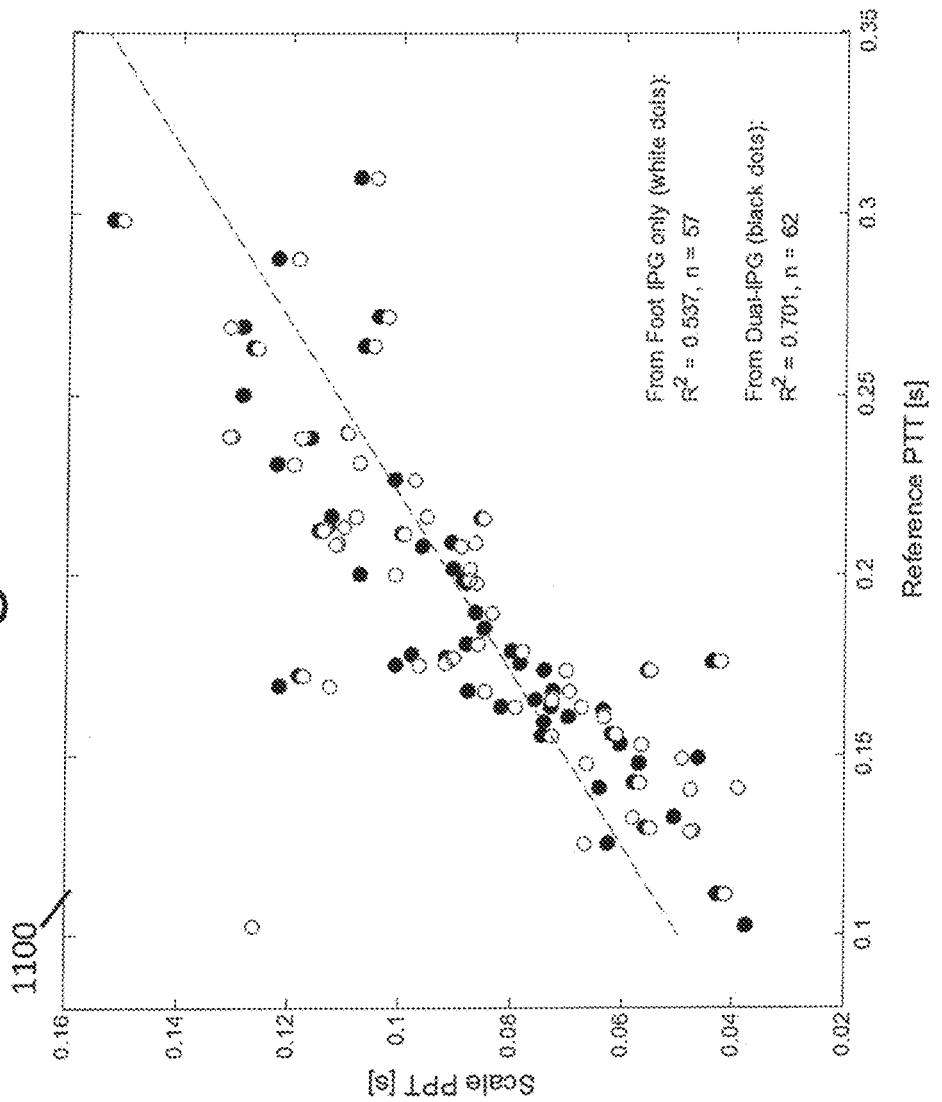
FIG. 11 shows an example graph of PTT correlations for two detection methods (white dots) Foot IPG only, and (black dots) Dual-IPG method, consistent with various aspects of the present disclosure.
Figure 12:
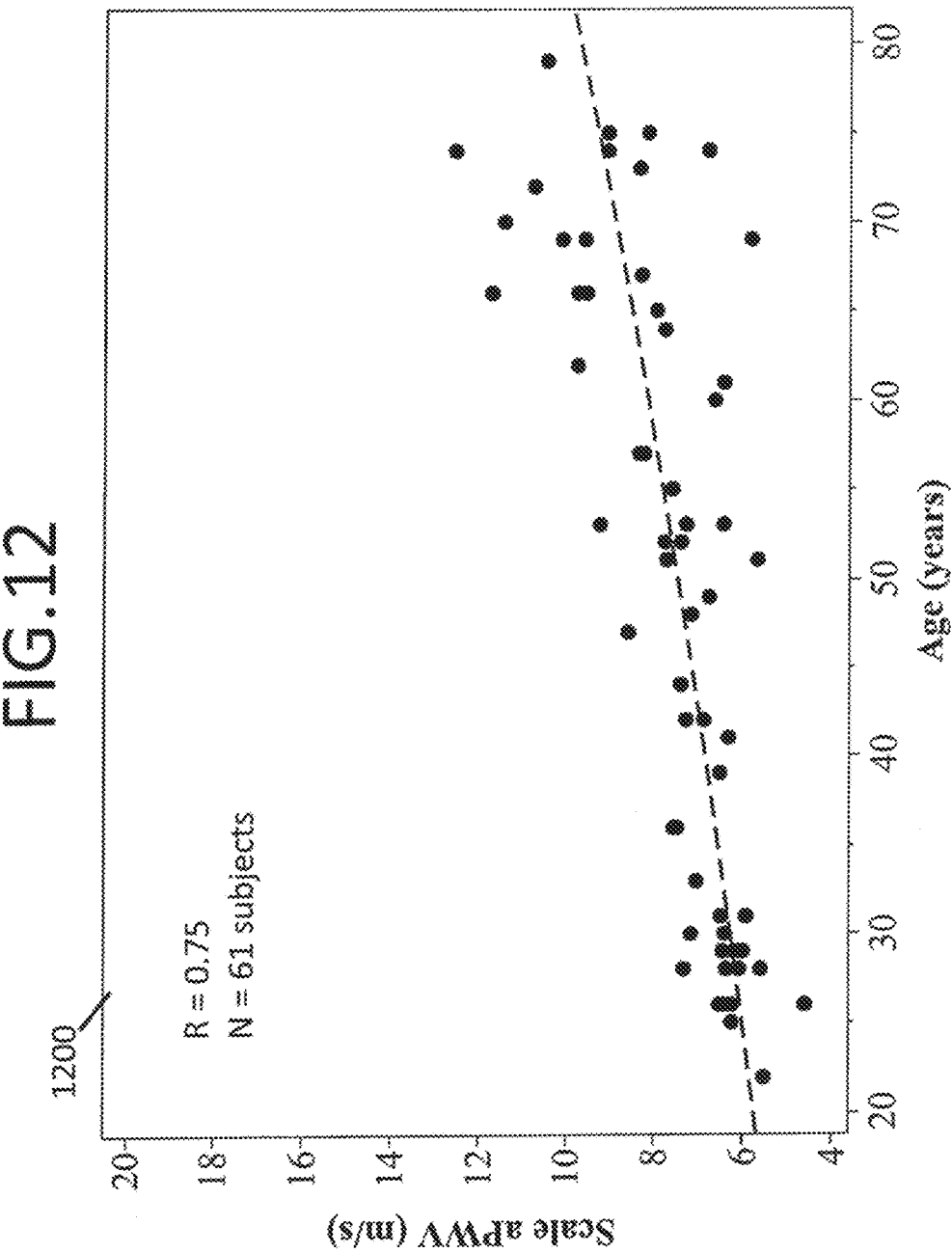
FIG. 12 shows an example graph of pulse wave velocity (PWV) obtained from the present disclosure compared to the ages of 61 human test subjects, consistent with various aspects of the present disclosure.

FIG. 11 shows an example graph 1100 of PTT correlations for two detection methods (white dots) Foot IPG only, and (black dots) Dual-IPG method; and FIG. 12 shows an example graph 1200 of PWV obtained from the present disclosure compared to the ages of 61 human test subjects, consistent with various aspects of the present disclosure.

Figure 13:
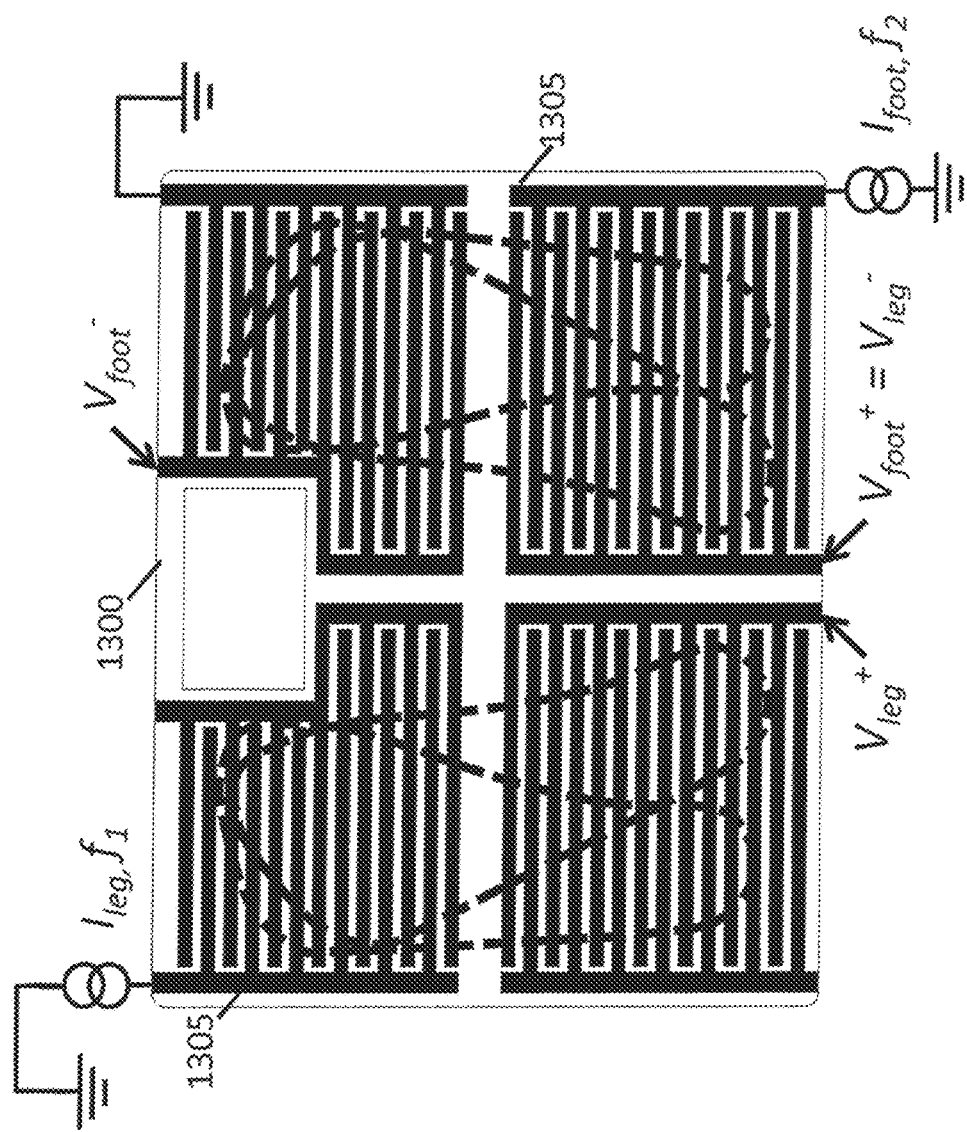
FIG. 13 shows another example of a scale with interleaved foot electrodes to inject and sense current from one foot to another foot, and within one foot, consistent with various aspects of the present disclosure.

FIG. 13 shows an example of a scale 1300 with integrated foot electrodes 1305 to inject and sense current from one foot to another foot, and within one foot.

Figure 14B:
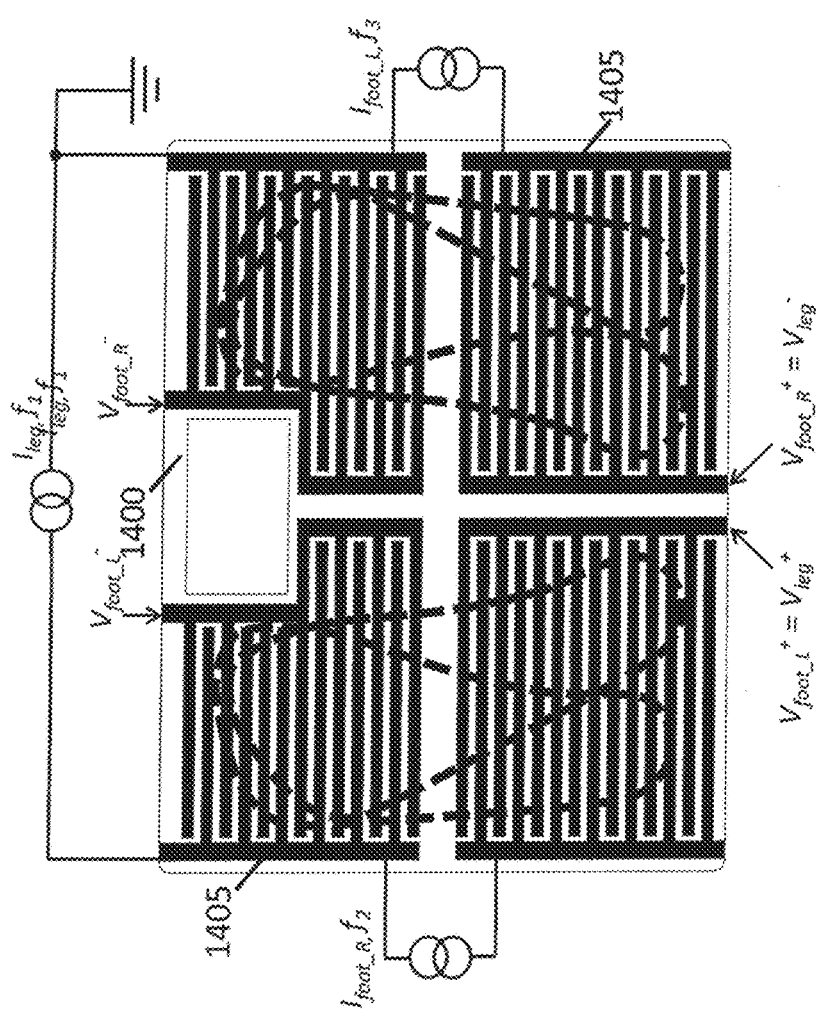
FIG. 14b shows another example of a scale with interleaved foot electrodes to inject and sense current from one foot to another foot, and measure Foot IPG signals in both feet, consistent with various aspects of the present disclosure.
Figure 14C:
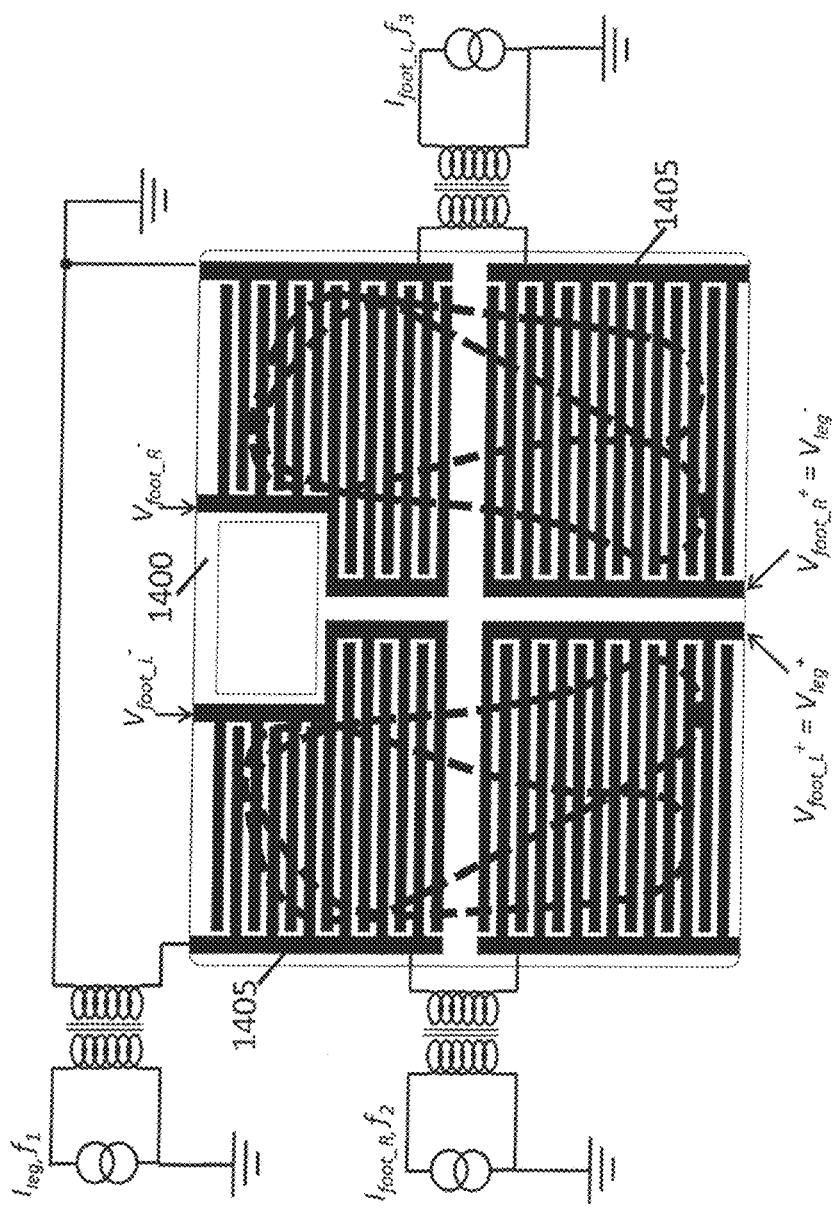
FIG. 14c shows another example approach to floating current sources is the use of transformer-coupled current sources, consistent with various aspects of the present disclosure.

FIG. 14*a-c* shows various examples of a scale 1400 with interleaved foot electrodes 1405 to inject/sense current from one foot to another foot, and measure Foot IPG signals in both feet.

FIGS. 15*a-d* shows an example breakdown of a scale 1500 with interleaved foot electrodes 1505 to inject and sense current from one foot to another foot, and within one foot.

Figure 16:
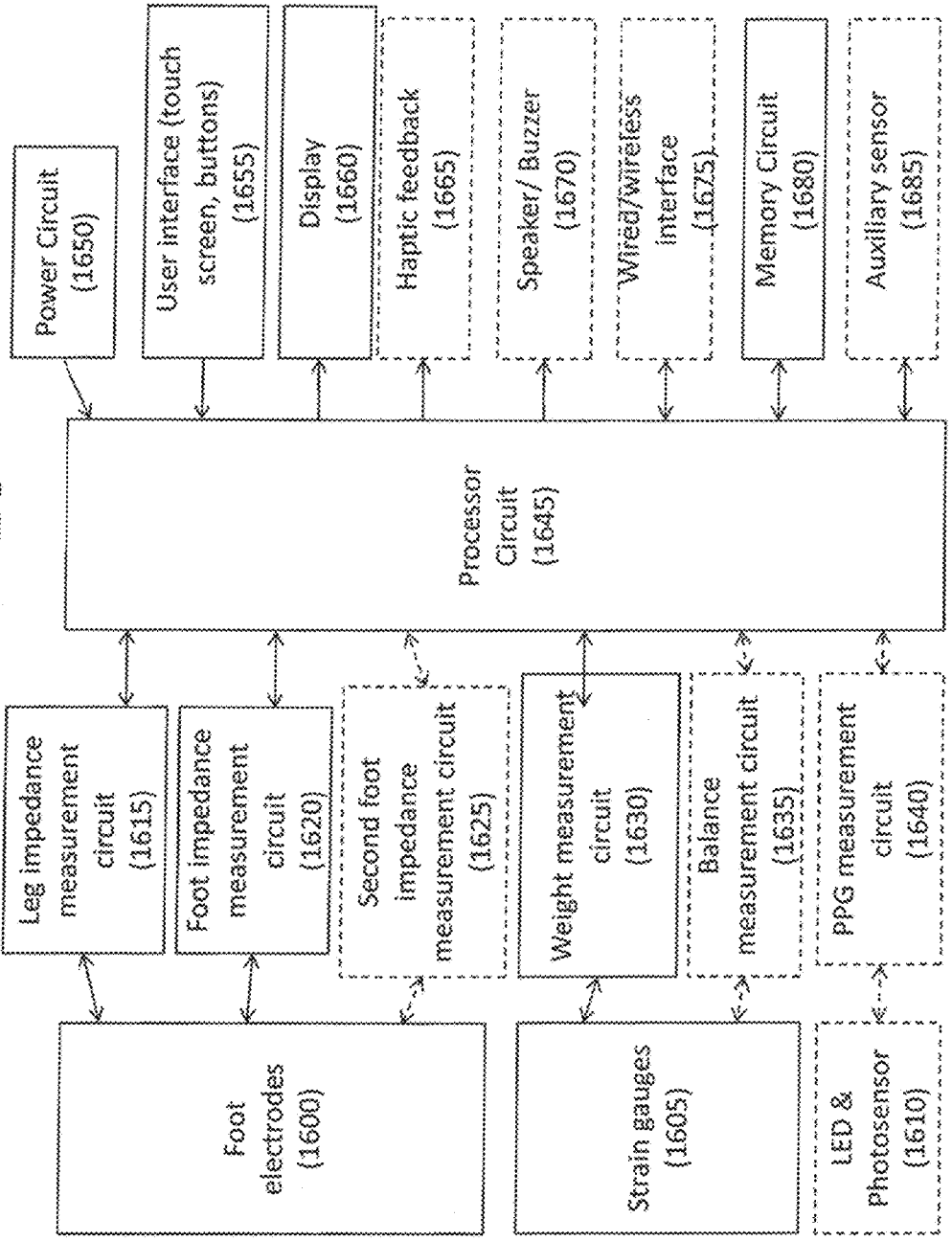
FIG. 16 shows an example block diagram of circuit-based building blocks, consistent with various aspects of the present disclosure.

FIG. 16 shows an example block diagram of circuit-based building blocks, consistent with various aspects of the present disclosure. The various circuit-based building blocks shown in FIG. 16 can be implemented in connection with the various aspects discussed herein. In the example shown, the block diagram includes foot electrodes 1600 that can collect the IPG signals. Further, the block diagram includes strain gauges 1605, and an LED/photosensor 1610. The foot electrodes 1600 is configured with a leg impedance measurement circuit 1615, a foot impedance measurement circuit 1620, and an optional second foot impedance measurement circuit 1625. The leg impedance measurement circuit 1615, the foot impedance measurement circuit 1620, and the optional second foot impedance measurement circuit 1625 report the measurements collected to a processor circuitry 1645.

The processor circuitry 1645 collects data from a weight measurement circuit 1630 and an optional balance measurement circuit 1635 that are configured with the strain gauges 1605. Further, an optional photoplethysmogram (PPG) measurement circuit 1640, which collects data from the LED/photosensor 1610, provides data to the processor circuitry 1645.

The processor circuitry 1645 is powered via a power circuit 1650. Further, the processor circuitry 1645 collects user input data from a user interface 1655 (e.g., iPad®, smart phone and/or other remote user handy/CPU with a touch screen and/or buttons). The data collected/measured by the processor circuitry 1645 is shown to the user via a display 1660. Additionally, the data collected/measured by the processor circuitry 1645 can be stored in a memory circuit 1680. Further, the processor circuitry 1645 can optionally control a haptic feedback circuit 1665, a speaker or buzzer 1670, a wired/wireless interface 1675, and an auxiliary sensor 1685 for one-way or two-way communication between the scale and the user.

Figure 17:
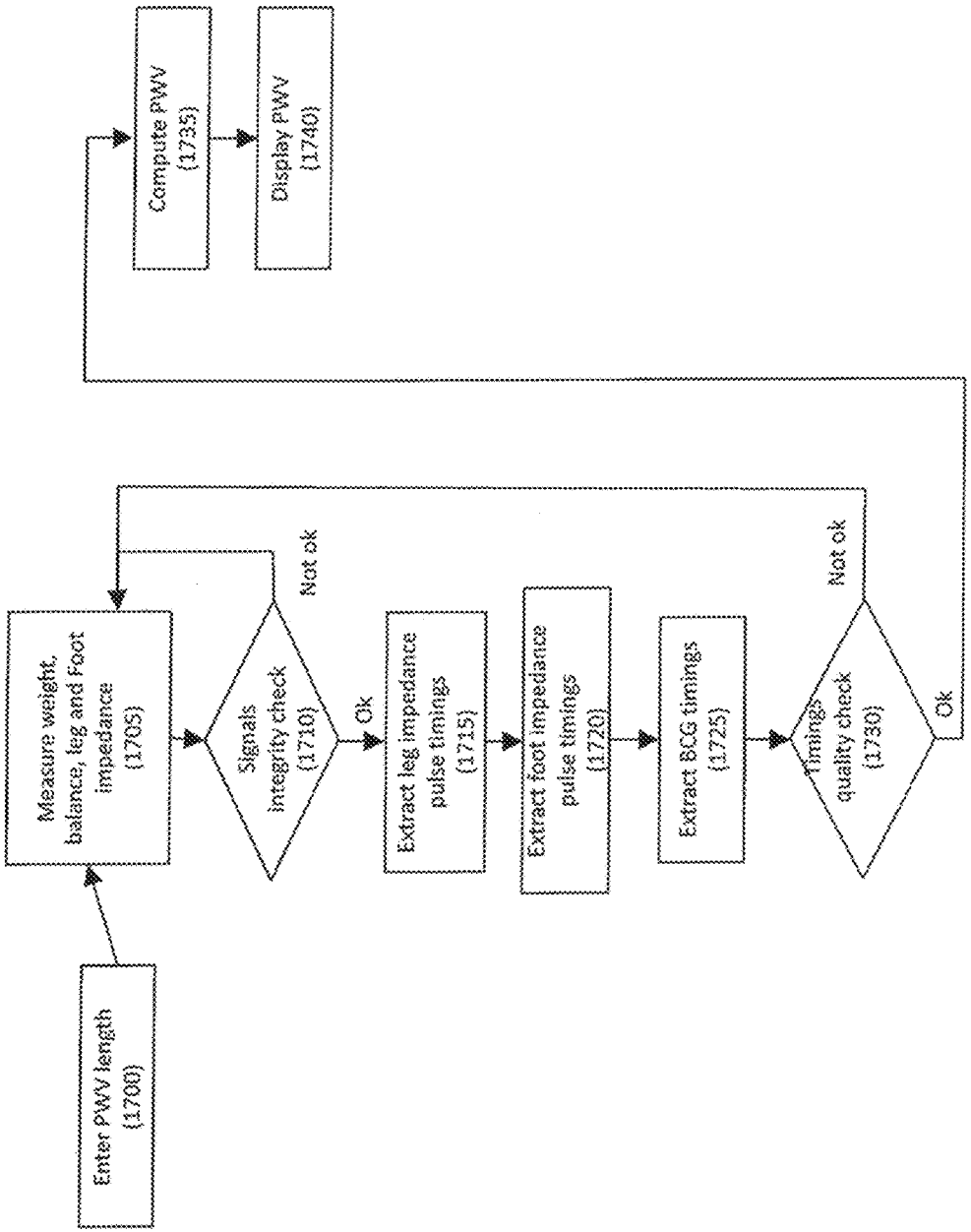
FIG. 17 shows an example flow diagram, consistent with various aspects of the present disclosure.

FIG. 17 shows an example flow diagram, consistent with various aspects of the present disclosure. At block 1700, a PWV length is entered. At block 1705, a user's weight, balance, leg, and foot impedance are measured. At 1710, the integrity of signals is checked (e.g., SNR). If the signal integrity check is not met, the user's weight, balance, leg, and foot impedance are measured again (block 1705), if the signals integrity check is met, the leg impedance pulse timings are extracted (as is shown at block 1715). At block 1720, foot impedance and pulse timings are extracted, and at block 1725, BCG timings are extracted. At block 1730, a timings quality check is performed. If the timings quality check is not validated, the user's weight, balance, leg and foot impedance are again measured (block 1705). If the timings quality check is validated, the PWV is calculated (as is shown at block 1735). At block 1740, the PWV is displayed to the user.

Figure 18:
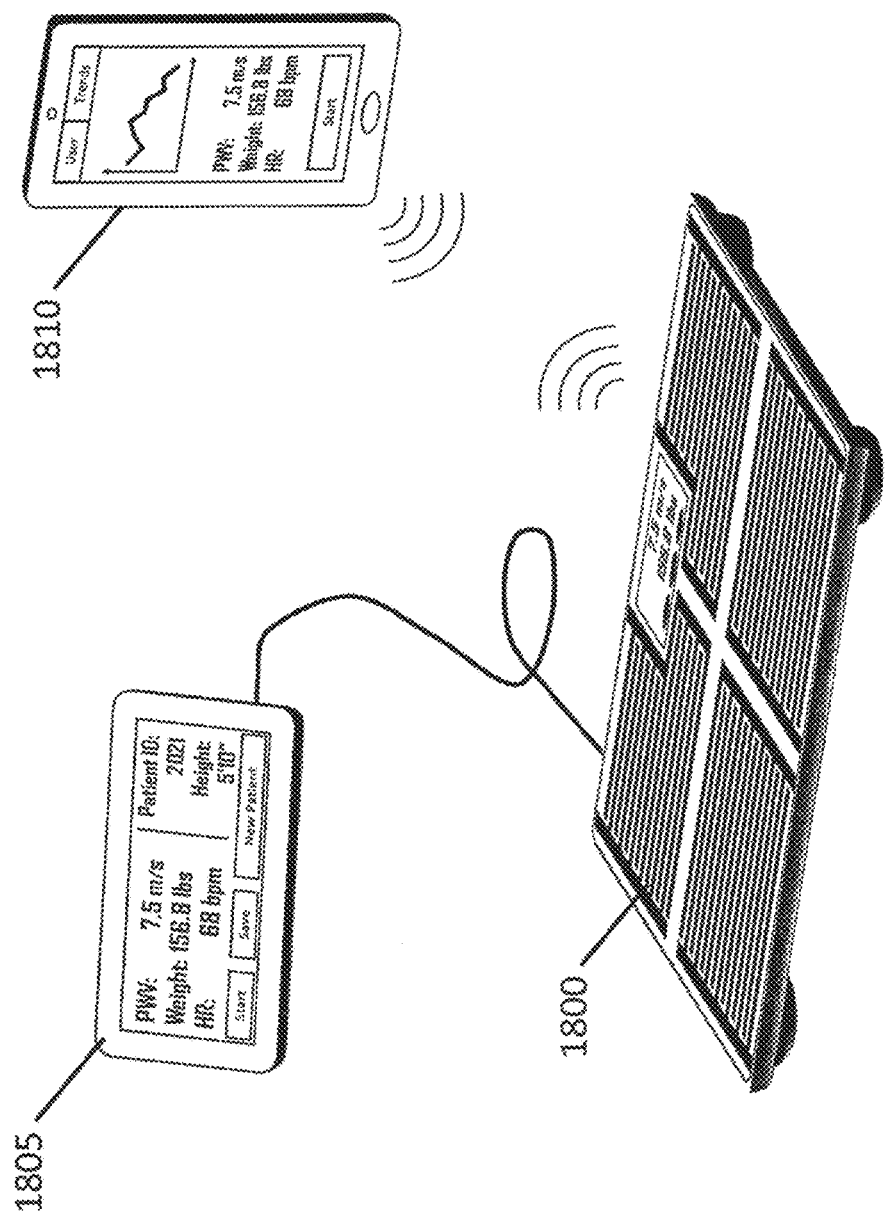
FIG. 18 shows an example scale communicatively coupled to a wireless device, consistent with various aspects of the present disclosure.

FIG. 18 shows an example scale 1800 communicatively coupled to a wireless device, consistent with various aspects of the present disclosure. As described herein, a display 1805 displays the various aspects measured by the scale 1800. The scale, in various embodiments, wirelessly broadcast the measurements to a wireless device 1810. The wireless device 1810, in some aspects, is implemented as an iPad®, smart phone or other CPU to provide input data for configuring and operating the scale.

As an alternative or complementary user interface, the scale includes a FUI which is enabled/implementable by one or more foot-based biometrics (for example, with the user being correlated to previously-entered user weight, toe print, an ECG-to-BCG timing relationship, and/or foot size/shape). The user foot-based biometric, in some embodiments, is implemented by the user manually entering data (e.g., a password) on the upper surface or display area of the scale. In implementations in which the scale is configured with a haptic, capacitive or flexible pressure-sensing upper surface, the (upper surface/tapping) touching from or by the user is sensed in the region of the surface and processed according to conventional X-Y grid Signal processing in the logic circuitry/CPU that is within the scale. By using one or more of the accelerometers located within the scale at its corners, such user data entry is sensed by each such accelerometer so long as the user's toe, heel or foot pressure associated with each tap provides sufficient force. Although the present discussion refers to a FUI, embodiments are not so limited. Various embodiments include internal or external GUIs that are in communication with the scale and used to obtain a biometric and that can be in place of the FUI and/or in combination with a FUI. For example, a user device having a GUI, such as tablet, is in communication with the scale via a wired or wireless connection. The user device obtains a biometric, such a finger print, and communicates the biometric to the scale.

In various embodiments, the above discussed user-interface is used with other features described herein for the purpose of storing and securing user sensitive data such as: the configuration data input by the user, the biometric and/or passwords entered by the user, and the user-specific health related data which might include data that is less sensitive to the user (e.g., the user's weight) and data that is more sensitive to the user (e.g., the user's scale obtains cardiograms and other data generated by or provided to the scale and associated with the user's symptoms and/or diagnoses). For such user-sensitive data, the above described biometrics are used as directed by the user for indicating and defining protocol to permit such data to be exported from the scale to other remote devices. In more specific embodiments, the scale operates in different modes of data security including, for example: a default mode in which the user's body mass and/or weight is displayed regardless of any biometric which would associate with the specific user standing on the scale; another mode in which complicated data (or data reviewed infrequently) is only exported from the scale under specific manual commands provided to the scale under specific protocols; and another mode or modes in which the user-specific data that is collected from the scale is processed and accessed based on the type of data. Such data categories include categories of different level of importance and/or sensitivities such as the above-discussed high and low level data and other data that might be very specific to a symptom and/or degrees of likelihood for diagnoses. Optionally, the CPU in the scale is also configured to provide encryption of various levels of sensitivity of the user's data.

For example, in accordance with various embodiments, the above-described FUI is used to provide portions of the user data, clinical indications (e.g., scale-obtained physiological data), generic health information, and/or other feedback to the user. In some embodiments, the scale includes a display configuration filter (e.g., circuitry and/or computer readable medium) configured to discern the data to display to the user and display portion. The display configuration filter discerns which portions of the user data, clinical indications, generic health information and/or other feedback to display to the user on the FUI based on various user demographic information (e.g., age, gender, height, diagnosis) and the amount of data. For example, the generic health information may include an amount of data that if all the data is displayed on the FUI the data is difficult for a person to read and/or uses multiple display screens.

The display configuration filter discerns portions of the data to display using the scale user interface, such as synopsis of the generic health information (or user data or feedback) and an indication that additional data is displayed on another user device, and other portions to display on the other user device. The other user device is selected by the scale (e.g., the filter) based on various communications settings. The communication settings include settings such as user settings (e.g., the user identifying user devices to output data to), scale-based biometrics (e.g., user configures scale, or default settings, to output data to user devices in response to identifying scale-based biometrics), and/or proximity of the user device (e.g., the scale outputs data to the closest user device among a plurality of user devices and/or in response to the user device being within a threshold distance from the scale), among other settings. For example, the scale determines which portions of the used data, clinical indication, generic health information and/or other feedback to output and outputs the remaining portion of the user data, clinical indication, generic health information and/or other feedback to a particular user device based on user settings/communication authorization (e.g., what user devices are authorized by the user to receive particular user data from the scale), and proximity of the user device to the scale. The determination of which portions to output is based on what type of data is being displayed, how much data is available, and the various user demographic information (e.g., an eighteen year old is able to see better than a fifty year old).

For example, in some specific embodiments, the scale operates in different modes of data security and communication. The different modes of data security and communication are enabled in response to biometrics identified by the user and using the FUI. In some embodiments, the scale is used by multiple users and/or the scale operates in different modes of data security and communication in response to identifying the user and based on biometrics. The different modes of data security and communication include, for example: a first mode (e.g., default mode) in which the user's body mass and/or weight is displayed regardless of any biometric which would associate with the specific user standing on the scale and no data is communicated to external circuitry; a second mode in which complicated/more-sensitive data (or data reviewed infrequently) is only exported from the scale under specific manual commands provided to the scale under specific protocols and in response to a biometric; and third mode or modes in which the user-specific data that is collected from the scale is processed and accessed based on the type of data and in response to a biometric. Such data categories include categories of different levels of importance and/or sensitivities such as the above-discussed high and low level data and other data that might be very specific to a symptom and/or degrees of likelihood for diagnoses. Optionally, the CPU in the scale is also configured to provide encryption of various levels of sensitivity of the user's data.

In some embodiments, the different modes of data security and communication are enabled in response to recognizing the user standing on the scale using a biometric and operating in a particular mode of data security and communication based on user preferences and/or services activated. For example, the different modes of operation include the default mode (as discussed above) in which certain data (e.g., categories of interest, categories of user data, or historical user data) is not communicated from the scale to external circuitry, a first communication mode in which data is communicated to external circuitry as identified in a user profile, a second or more communication modes in which data is communicated to a different external circuitry for further processing. The different communication modes are enabled based on biometrics identified from the user and user settings in a user profile corresponding with each user. Although the different communications are referred to as "modes", one of skill in the art may appreciate that the communications in the different modes may not (or may) include different media and channels. The different communication modes can include different devices communicated to and/or different data that is communicated based on sensitivity of the data and/or security of the devices.

In a specific embodiment, a first user of the scale may not be identified and/or have a user profile set up. In response to the first user standing on the scale, the scale operates in a default mode. During the default mode, the scale displays the user's body mass and/or weight on the user display and does not output user data. The scale, in various embodiments, displays a prompt (e.g., an icon) on the FUI indicating the first user can establish a user profile. In response to the user selecting the prompt, the scale enters an initialization mode. During the initialization mode, the scale asks the users various questions, such as identification of external circuitry to send data to, identification information of the first user, and/or demographics of the user. The user provides inputs using the FUI to establish various communication modes associated with the user profile and scale-based biometrics to enable the one or more communication modes. The scale further collects user data to identify the scale-based biometrics and stores an indication of the scale-based biometric in the user profile such that during subsequent measurements, the scale recognizes the user and authorizes a particular communication mode. Alternatively, the user provides inputs for the initialization mode using another device that is external to the scale and in communication with the scale (e.g., a cellphone).

A second user of the scale has a user profile set up that indicates the user would like data communicated to a computing device of the user. When the second user stands on the scale, the scale recognizes the second user based on a biometric and operates in a first communication mode. During the first communication mode, the scale outputs at least a portion of the user data to an identified external circuitry. For example, the first communication mode allows the user to upload data from the scale to a user identified external circuitry (e.g., the computing device of the user). The information may include user data and/or user information that has low-user sensitivity, such as user weight and/or bmi. In the first communication mode, the scale performs the processing of the raw sensor data and/or the external circuitry can. For example, the scale sends the raw sensor data and/or additional health information to a user device of the user. The computing device may not provide access to the raw sensor data to the user and/or can send the raw sensor data to another external circuitry for further processing in response to a user input. For example, the computing device can ask the user if the user would like generic health information and/or regulated health information as a service. In response to receiving an indication the user would like the generic health information and/or regulated health information, the computing device outputs the raw sensor data and/or non-regulated health information to another external circuitry for processing, providing to a physician for review, and controlling access, as discussed above.

In one or more additional communication modes, the scale outputs raw sensor data to an external circuitry for further processing. For example, during a second communication mode and a third communication, the scale sends the raw sensor data and/or other data to external circuitry for processing. Using the above-provided example, a third user of the scale has a user profile set up that indicates the third user would like scale-obtained data to be communicated to an external circuitry for further processing, such as to determine generic health information. When the third user stands on the scale, the scale recognizes the third user based on one or more biometrics and operates in a second communication mode. During the second communication mode, the scale outputs raw sensor data to the external circuitry. The external circuitry identifies one or more risks, and, optionally, derives generic health information. In some embodiments, the external circuitry outputs the generic health information to the scale. The scale, in some embodiments, displays a synopsis of the generic health information and/or outputs a full version of the generic health information to another user device for display (such as, using the filter described above) and/or an indication that generic health information can be accessed.

A fourth user of the scale has a user profile set up that indicates the fourth user has enabled a service to access regulated health information. When the fourth user stands on the scale, the scale recognizes the user based on one or more biometrics and operates in a fourth communication mode. In the fourth communication mode, the scale outputs raw sensor data to the external circuitry, and the external circuitry processes the raw sensor data and controls access to the data. For example, the external circuitry may not allow access to the regulated health information until a physician reviews the information. In some embodiments, the external circuitry outputs data to the scale, in response to physician review. For example, the output data can include the regulated health information and/or an indication that regulated health information is ready for review. The external circuitry may be accessed by the user, using the scale and/or another user device. In some embodiments, using the foot-controlled user-interface of the scale, the scale displays the regulated health information to the user. The scale, in some embodiments, displays a synopsis of the regulated health information (e.g., clinical indication) and outputs the full version of regulated health information to another user device for display (such as, using the filter described above) and/or an indication that the regulated health information can be accessed to the scale to display. In various embodiments, if the scale is unable to identify a particular (high security) biometric that enables the fourth communication mode, the scale may operate in a different communication mode and may still recognize the user. For example, the scale may operate in a default communication mode in which the user data collected by the scale is stored in a user profile corresponding to the fourth user and on the scale. In some related embodiments, the user data is output to the external circuitry at a different time.

Although the present embodiments illustrates a number of security and communication modes, embodiments in accordance with the present disclosure can include additional or fewer modes. Furthermore, embodiments are not limited to different modes based on different users. For example, a single user may enable different communication modes in response to particular biometrics of the user identified and/or based on user settings in a user profile.

In various embodiments, the scale defines a user data table that defines types of user data and sensitivity values of each type of user data, as previously illustrated herein. In specific embodiments, the FUI displays the user data table. In other specific embodiments a user interface of a smartphone, tablet, and/or other computing device displays the user data table. For example, a wired or wireless tablet is used, in some embodiments, to display the user data table. The sensitivity values of each type of user data, in some embodiments, define in which communication mode(s) the data type is communicated and/or which biometric is used to enable communication of the data type. In some embodiments, a default or pre-set user data table is displayed and the user revises the user data table using the FUI. The revisions are in response to user inputs using the user's foot and/or contacting or moving relative to the foot-controlled user interface. Although the embodiments are not so limited, the above (and below) described control and display is provided using a wireless or wired tablet or other computing device as a user interface. The output to the wireless or wired tablet, as well as additional external circuitry, is enabled using biometrics. For example, the user is encouraged, in particular embodiments, to configure the scale with various biometrics. The biometric include scale-based biometrics and biometrics from the tablet or other user computing device. The biometric, in some embodiments, used to enable output of data to the tablet and/or other external circuitry includes a higher integrity biometric (e.g., higher likelihood of identifying the user accurately) than a biometric used to identify the user and stored data on the scale.

In accordance with various embodiments, the scale uses a cardiogram of the user and/or other scale-obtained biometrics to differentiate between two or more users. The scale-obtained data includes health data that is user-sensitive, such that unintentional disclosure of scale-obtained data is not desired. Differentiating between the two or more users and automatically communicating (e.g., without further user input) user data responsive to scale-obtained biometrics, in various embodiments, provides a user-friendly and simple way to communicate data from a scale while avoiding and/or mitigating unintentional (and/or without user consent) communication. For example, the scale, such as during an initialization mode for each of the two or more users and as previously discussed, collects user data to identify the scale-based biometrics and stores an indication of the scale-based biometrics in a user profile corresponding with the respective user. During subsequent measurements, the scale recognizes the particular user by comparing collected signals to the indication of the scale-based biometrics in the user profile. The scale, for example, compares the collected signals to each user profile of the two or more users and identifies a match between the collected signals and the indication of the scale-based biometrics. A match, in various embodiments, is within a range of values of the indication stored. Further, in response to verifying the scale-based biometric(s), a particular communication mode is authorized.

In accordance with a number of embodiments, the scale identifies one or more of the multiple users of the scale that have priority user data. The user data with a priority, as used herein, includes an importance of the user and/or the user data. In various embodiments, the importance of the user is based on parameter values identified and/or user goals, such as the user is an athlete and/or is using the scale to assist in training for an event (e.g., marathon) or is using the scale for other user goals (e.g., a weight loss program). Further, the importance of the user data is based on parameters values and/or user input data indicating a diagnosis of a condition or disease and/or a risk of the user having the condition or disease based on the scale-obtained data. For example, the scale-obtained data of a first user indicates that the user is overweight, recently had an increase in weight, and has a risk of having atrial fibrillation. The first user is identified as a user corresponding with priority user data. A second user of the scale has scale-obtained data indicating a decrease in recovery parameters (e.g., time to return to baseline parameters) and the user inputs an indication that they are training for a marathon. The second user is also identified as a user corresponding with priority user data. The scale displays indications to user with the priority user data, in some embodiments, on how to use to the scale to communicate the user data to external circuitry for further processing, correlation, and/or other features, such as social network connections. Further, the scale, in response to the priority, displays various feedback to the user, such as user-targeted advertisements and/or suggestions. In some embodiments, only users with priority user data have data output to the external circuitry to determine risks, although embodiments in accordance with the present disclosure are not so limited.

In some embodiments, one or more users of the scale have multiple different scale-obtained biometrics used to authorize different communication modes. The different scale-obtained biometrics are used to authorize communication of different levels of user-sensitive data, such as the different user-data types and sensitivity values as illustrated in the above-table. For example, in some specific embodiments, the different scale-obtained biometrics include a high security biometric, a medium security biometric, and a low security biometric. Using the above illustrated table as an example, the three different biometrics are used to authorize communication of the user-data types of the different sensitivity values. For instance, the high security biometric authorizes communication of user-data types with sensitivity values of 8-10, the medium security biometric authorizes communication of user-data types with sensitivity values of 4-7, and the low security biometric authorizes communication of user-data types with sensitivity values of 1-3. The user, in some embodiments, can adjust the setting of the various biometrics and authorization of user data types.

In a specific example, low security biometrics includes estimated weight (e.g., a weight range), and a toe tap on the FUI. Example medium security biometrics includes one or more the low security biometric in addition to length and/or width or other shape of the user's foot, and/or a time of day or location of the scale. For example, as illustrated by FIGS. 2a and 13 and discussed with regard to FIG. 3c, the scale includes impedance electrodes that are interleaved and engage the feet of the user. The interleaved electrodes assist in providing measurement results that are indicative of the foot length, foot width, and type of arch. Further, a specific user, in some embodiments, may use the scale at a particular time of the day and/or authorize communication of data at the particular time of the day, which is used to verify identity of the user and authorize the communication. The location of scale, in some embodiments, is based on Global Positioning System (GPS) coordinates and/or a Wi-Fi code. For example, if the scale is moved to a new house, the Wi-Fi code used to communicate data externally from the scale changes. Example high security biometrics include one or more low security biometrics and/or medium security biometrics in addition to cardiogram characteristics and, optionally, a time of day and/or heart rate. Example cardiogram characteristics include a QRS complex, and QRS complex and P/T wave, BCG wave characteristics, and an ECG-to-BCG timing relationship.

In various embodiments, the user adjusts the table displayed above to revise the sensitivity values of each data type. Further, although the above-illustrated table includes a single sensitivity value for each data type, in various embodiments, one or more of the data types are separated into sub-data types and each sub-data type has a sensitivity value. As an example, the user-specific advertisement is separated into: prescription advertisement, external device advertisements, exercise advertisements, and diet plan advertisement. Alternatively and/or in addition, the sub-data types for user-specific advertisement include generic advertisements based on a demographic of the user and advertisements in response to scale collected data (e.g., advertisement for a device in response to physiologic parameters), as discussed further herein.

For example, weight data includes the user's weight and historical weight as collected by the scale. In some embodiments, weight data includes historical trends of the user's weight and correlates to dietary information and/or exercise information, among other user data. Body mass index data, includes the user's body mass index as determined using the user's weight collected by the scale and height. In some embodiments, similar to weight, body mass index data includes history trends of the user's body mass index and correlates to various other user data.

User-specific advertisement data includes various prescriptions, exercise plans, dietary plans, and/or other user devices and/or sensors for purchase, among other advertisements. The user-specific advertisements, in various embodiments, are correlated to input user data and/or scale-obtained data. For example, the advertisements include generic advertisements that are relevant to the user based on a demographic of the user. Further, the advertisements include advertisements that are responsive to scale collected data (e.g., physiological parameter includes a symptom or problem and advertisement is correlated to the symptom or problem). A number of specific examples include advertisements for beta blockers to slow heart rate, advertisements for a user wearable device (e.g., Fitbit®) to monitor heart rate, and advertisements for a marathon exercise program (such as in response to an indication the user is training for a marathon), etc.

Physician provided diagnosis/report data includes data provided by a physician and, in various embodiments, is in responsive to the physician reviewing the scale-obtained data. For example, the physician provided diagnosis/report data includes diagnosis of a disorder/condition by a physician, prescription medication prescribed by a physician, and/or reports of progress by a physician, among other data. In various embodiments, the physician provided diagnosis/reports are provided to the scale from external circuitry, which includes and/or accesses a medical profile of the user.

Suggestion data includes data that provides suggestions or advice for symptoms, diagnosis, and/or user goals. For example, the suggestions include advice for training that is user specific (e.g., exercise program based on user age, weight, and cardiogram data or exercise program for training for an event or reducing time to complete an event, such as a marathon), suggestions for reducing symptoms including dietary, exercise, and sleep advice, and/or suggestions to see a physician, among other suggestions. Further, the suggestions or advice include reminders regarding prescriptions. For example, based on physician provided diagnosis/report data and/or user inputs, the scale identifies the user is taking a prescription medication. The identification includes the amount and timing of when the user takes the medication, in some embodiments. The scale reminds the user and/or asks for verification of consumption of the prescription medication using the FUI.

As further specific examples, recent discoveries may align and associate different attributes of scale-based user data collected by the scale to different tools, advertisements, and physician provided diagnosis. For example, it has recently been discovered that atrial fibrillation is more directly correlated with obesity. The scale collects various user data and monitors weight and various components/symptoms of atrial fibrillation. In a specific embodiment, the scale recommends/suggests to the user to: closely monitor weight, recommends a diet, goals for losing weight, and correlates weight gain and losses for movement in cardiogram data relative to arrhythmia. The movement in cardiogram data relative to arrhythmia, in specific embodiments, is related to atrial fibrillation. For example, atrial fibrillation is associated with indiscernible p-waves and beat to beat fluctuations. Thereby, the scale correlates weight gain/loss with changes in amplitude (e.g., discernibility) of a p-wave of a cardiogram (preceding a QRS complex) and changes in beat to beat fluctuations.

FIGS. 19*a-c* show example impedance as measured through different parts of the foot based on the foot position, consistent with various aspects of the present disclosure. For instance, example impedance measurement configurations may be implemented using a dynamic electrode configuration for measurement of foot impedance and related timings. Dynamic electrode configuration may be implemented using independently-configurable electrodes to optimize the impedance measurement. As shown in FIG. 19*a*, interleaved electrodes 1900 are connected to an impedance processor circuit 1905 to determine foot length, foot position, and/or foot impedance. As is shown in FIG. 19*b*, an impedance measurement is determined regardless of foot position 1910 based on measurement of the placement of the foot across the electrodes 1900. This is based in part in the electrodes 1900 that are engaged (blackened) and in contact with the foot (based on the foot position 1910), which is shown in FIG. 19*c*.

More specifically regarding FIG. 19*a*, configuration includes connection/de-connection of the individual electrodes 1900 to the impedance processor circuit 1905, their configuration as current-carrying electrodes (injection or return), sense electrodes (positive or negative), or both. The configuration is preset based on user information, or updated at each measurement (dynamic reconfiguration) to optimize a given parameter (impedance SNR, measurement location). The system algorithmically determines which electrodes under the foot to use in order to obtain the highest SNR in the pulse impedance signal. Such optimization algorithm may include iteratively switching configurations and measuring the impedance, and selecting the best suited configuration. Alternatively, the system first, through a sequential impedance measurement between each individual electrode 1900 and another electrode in contact with the body (such as an electrode in electrode pair 205 on the other foot), determine which electrodes are in contact with the foot. By determining the two most apart electrodes, the foot size is determined. Heel location can be determined in this manner, as can other characteristics such as foot arch type. These parameters are used to determine programmatically (in an automated manner by CPU/logic circuitry) which electrodes are selected for current injection and return (and sensing if a Kelvin connection issued) to obtain the best foot IPG.

In various embodiments involving the dynamically reconfigurable electrode array 1900/1905, an electrode array set is selected to measure the same portion/segment of the foot, irrespective of the foot location on the array. FIG. 19*b* illustrates the case of several foot positions on a static array (a fixed set of electrodes are used for measurement at the heel and plantar/toe areas, with a fixed gap of an inactive electrode or insulating material between them). Depending on the position of the foot, the active electrodes are contacting the foot at different locations, thereby sensing a different volume/segment of the foot. If the IPG is used by itself (e.g., for heart measurement), such discrepancies may be non-consequential. However, if timings derived from the IPG are referred to other timings (e.g., R-wave from the ECG, or specific timing in the BCG), such as for the calculation of a PTT or PWV, the small shifts in IPG timings due to the sensing of slightly different volumes in the foot (e.g., if the foot is not always placed at the same position on the electrodes) can introduce an error in the calculation of the interval. With respect to FIG. 19b, the timing of the peak of the IPG from the foot placement on the right (sensing the toe/plantar region) is later than from the foot placement on the left, which senses more of the heel volume (the pulse reaches first the heel, then the plantar region). Factors influencing the magnitude of these discrepancies include foot shape (flat or not) and foot length.

Various embodiments address challenges relating to foot placement. FIG. 19c shows an example embodiment involving dynamic reconfiguration of the electrodes to reduce such foot placement-induced variations. As an example, by sensing the location of the heel first (as described above), it is possible to activate a subset of electrodes under the heel, and another subset of electrodes separated by a fixed distance (1900). The other electrodes (e.g., unused electrodes) are left disconnected. The sensed volume will therefore be the same, producing consistent timings. The electrode configuration leading to the most consistent results may be informed by the foot impedance, foot length, the type of arch (all of which can be measured by the electrode array as shown above), but also by the user ID (foot information can be stored for each user, then looked up based on automatic user recognition or manual selection (e.g., in a look-up-table stored for each user in a memory circuit accessible by the CPU circuit in the scale).

In certain embodiments, the apparatus measures impedance using a plurality of electrodes contacting one foot and with at least one other electrode (typically many) at a location distal from the foot. The plurality of electrodes (contacting the one foot) is arranged on the platform and in a pattern configured to inject current signals and sense signals in response thereto, for the same segment of the foot so that the timing of the pulse-based measurements does not vary because the user placed the one foot at a slightly different position on the platform or scale. In FIG. 19a, the foot-to-electrode locations for the heel are different locations than that shown in FIGS. 19b and 19c. As this different foot placement can occur from day to day for the user, the timing and related impedance measurements are for the same (internal) segment of the foot. By having the processor circuit inject current and sense responsive signals to first locate the foot on the electrodes (e.g., sensing where positions of the foot's heel plantar regions and/or toes), the pattern of foot-to-electrode locations permits the foot to move laterally, horizontally and both laterally and horizontally via the different electrode locations, while collecting impedance measurements relative to the same segment of the foot.

The BCG/IPG system can be used to determine the PTT of the user, by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. In certain embodiments, the BCG/IPG system is used to determine the PWV of the user, by identification of the characteristic length representing the length of the user's arteries, and by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. The system of the present disclosure and alternate embodiments may be suitable for determining the arterial stiffness (or arterial compliance) and/or cardiovascular risk of the user regardless of the position of the user's feet within the bounds of the interleaved electrodes. In certain embodiments, the weighing scale system incorporated the use of strain gage load cells and six or eight electrodes to measure a plurality of signals including: bodyweight, BCG, body mass index, fat percentage, muscle mass percentage, and body water percentage, heart rate, heart rate variability, PTT, and PWV measured simultaneously or synchronously when the user stands on the scale to provide a comprehensive analysis of the health and wellness of the user.

In other certain embodiments, the PTT and PWV are computed using timings from the Leg IPG or Foot IPG for arrival times, and using timings from a sensor located on the upper body (as opposed to the scale measuring the BCG) to detect the start of the pulse. Such sensor may include an impedance sensor for impedance cardiography, a hand-to-hand impedance sensor, a photoplethysmogram on the chest, neck, head, arms or hands, or an accelerometer on the chest (seismocardiograph) or head.

Communication of the biometric information is another aspect of the present disclosure. The biometric results from the user are stored in the memory on the scale and displayed to the user via a display on the scale, audible communication from the scale, and/or the data is communicated to a peripheral device such as a computer, smart phone, tablet computing device. The communication occurs to the peripheral device with a wired connection, or can be sent to the peripheral device through wireless communication protocols such as Bluetooth or WiFi. Computations such as signal analyses described therein may be carried out locally on the scale, in a smartphone or computer, or in a remote processor (cloud computing).

Other aspects of the present disclosure are directed toward apparatuses or methods that include the use of at least two electrodes that contacts feet of a user. Further, circuitry is provided to determine a pulse arrival time at the foot based on the recording of two or more impedance signals from the set of electrodes. Additionally, a second set of circuitry is provided to extract a first pulse arrival time from a first impedance signal and use the first pulse arrival time as a timing reference to extract and process a second pulse arrival time in a second impedance signal.

Reference may also be made to published patent documents U.S. Patent Publication 2010/0094147 and U.S. Patent Publication 2013/0310700, which are, together with the references cited therein, herein fully incorporated by reference for the purposes of sensors and sensing technology. The aspects discussed therein may be implemented in connection with one or more of embodiments and implementations of the present disclosure (as well as with those shown in the figures). In view of the description herein, those skilled in the art will recognize that many changes may be made thereto without departing from the spirit and scope of the present disclosure.

Various embodiments are implemented in accordance with, and fully incorporating by reference for their general teachings, the above-identified PCT Applications and U.S. Provisional applications (including PCT Ser. No. PCT/US2016/062484 and PCT Ser. No. PCT/US2016/062505), which teachings are also incorporated by reference specifically concerning physiological scales and related measurements and communications such as exemplified by disclosure in connection with FIGS. 1a, 1b, 1e, 1f, 1n, 10, 1p, and 2b-2e in PCT Ser. No. PCT/US2016/062484 and FIGS. 1a, 1k, 1l, and 1m in PCT. Ser. No. PCT/US2016/062505, and related disclosure in the above-identified U.S. Provisional applications. For example, U.S. Provisional application (Ser. No. 62/258,238), which teachings are also incorporated by reference specifically concerning obtaining derivation data, assessing a condition or treatment of the user features and aspects as exemplified by disclosure in connection with FIGS. 1a-1b of the underlying provisional; U.S. Provisional application (Ser. No. 62/266,403), which teachings are also incorporated by reference specifically concerning providing different levels of services to scale users by selectively prompting the user and responsive to different weighted values features and aspects as described in connection with FIGS. 1a-1d in the underlying provisional; and U.S. Provisional application (Ser. No. 62/266,523), which teachings are also incorporated by reference specifically concerning grouping users into inter and intra scale social groups based on aggregated user data sets, and providing normalized user data to other users in the social group aspects as exemplified by disclosure in connection with FIGS. 1a-1c of the underlying provisional. For instance, embodiments herein and/or in the PCT and/or provisional applications may be combined in varying degrees (including wholly). Reference may also be made to the experimental teachings and underlying references provided in the PCT and/or provisional applications. Embodiments discussed in the provisional applicants are not intended, in any way, to be limiting to the overall technical disclosure.

As illustrated herein, various circuit-based building blocks and/or modules may be implemented to carry out one or more of the operations/activities described herein shown in the block-diagram-type figures. In such contexts, these building blocks and/or modules represent circuits that carry out these or related operations/activities. For example, in certain embodiments discussed above (such as the pulse circuitry modularized as shown in FIGS. 3a-b), one or more blocks/modules are discrete logic circuits or programmable logic circuits for implementing these operations/activities, as in the circuit blocks/modules shown. In certain embodiments, the programmable circuit is one or more computer circuits programmed to execute a set (or sets) of instructions (and/or configuration data). The instructions (and/or configuration data) can be in the form of firmware or software stored in and accessible from a memory circuit. As an example, first and second modules/blocks include a combination of a CPU hardware-based circuit and a set of instructions in the form of firmware, where the first module/block includes a first CPU hardware circuit with one set of instructions and the second module/block includes a second CPU hardware circuit with another set of instructions.

Based upon the above discussion and illustrations, those skilled in the art will readily recognize that various modifications and changes may be made to the present disclosure without strictly following the exemplary embodiments and applications illustrated and described herein. For example, the input terminals as shown and discussed may be replaced with terminals of different arrangements, and different types and numbers of input configurations (e.g., involving different types of input circuits and related connectivity). Further, the various features and operations/actions, in accordance with various embodiments, can be combined with various different features and operations/actions and in various combinations. For example, the feature of providing a hierarchy of services can be used in combination with discerning which data to display on the user interface of the scale and which data to display on another device. Such modifications do not depart from the true spirit and scope of the present disclosure, including that set forth in the following claims.

What is claimed is:

1. An apparatus comprising:
a weighing scale including:
a platform including force sensor circuitry and a plurality of electrodes integrated with the platform, and configured and arranged to engage a user with electrical signals and collect signals indicative of the user's identity and cardio-related physiologic data while the user is standing on the platform; and
processing circuitry, including a CPU and a memory circuit with user-corresponding data stored in the memory circuit, configured and arranged with the force sensor circuitry and the plurality of electrodes and being configured to:
collect scale-obtained data including cardio-related physiologic data from the user while the user is standing on the platform and output at least portions of the cardio-related physiologic data as user data; and
provide a hierarchy of health-information services pertaining to the scale-obtained data in response to the user selecting a scale-generated prompt for a service corresponding to a subscription level, wherein the hierarchy of health-information services include different services enabled in response to user selection of one or more of the different services and activation of subscription levels of different values weighted relative to a degree of health-information sensitivity of data provided to the user.

2. The apparatus of claim 1, wherein the scale is configured to provide the hierarchy of services by providing a prompt for a first service in response to scale-obtained data using the scale, and in response to the user selecting the prompt providing a prompt for a second service that pertains to a subscription level with a weighted value, wherein the weighted valued pertains to a value of the one of the different services to the user, a service provider, and/or a third party.

3. The apparatus of claim 1, wherein the hierarchy of services include a service that provides access to different social groups, wherein the different social groups includes a consumer based social group with no weighted value and pertaining to a first subscription level, a physiological social group with a first weighted value and pertaining to a second subscription level, and a profession a social group with a second weighted value and pertaining to a third subscription level.

4. The apparatus of claim 1, wherein the hierarchy of services include generic health information pertaining to the scale-obtained data, products or services correlated to the scale-obtained data, and/or additional tests to perform responsive to the scale-obtained data.

5. The apparatus of claim 1, wherein the hierarchy of services include subscription levels of various weighted values.

6. The apparatus of claim 1, wherein the scale is configured to provide a first prompt to the user to access a first service of a first subscription level and in response to the user selecting the first prompt and the scale providing the first service to the user, the scale is configured to provide a second prompt to the user to access a second service of a second subscription level that has a weighted value which is greater than the first subscription level.

7. The apparatus of claim 6, wherein the scale is configured to provide a prompt for a third service of the first subscription level in response to the user not selecting the prompt for the second service.

8. The apparatus of claim 1, further including external circuitry is configured to securely pool user data from a plurality of scales, including the weighing scale, and communicate subsets of the securely pooled user data to other external circuitry, wherein the subsets of the securely pooled user data communicated has identifiers that indicates an identity of the scale and the users replaced with alias IDs.

9. The apparatus of claim 8, wherein the external circuitry identifies respective users and scales that are associated with the subsets of securely pooled user data communicated to the other external circuitry and outputs a prompt to the respective scales to indicate a request by a researcher, and
the respective scale's provide an indication of the request responsive to the output from the external circuitry.

10. The apparatus of claim 8, wherein the external circuitry is configured to identify respective users and scales that are associated with the subsets of securely pooled user data communicated to the other external circuitry and outputs a prompt to the respective scales to indicate a request by a researcher, wherein the external circuitry is configured to provide outputs to a portion of the users for a control group of a study and the remaining users as an experimental group, wherein the respective scales direct the user to perform the study and to encourage proper participation in the study in response to an user input indicating an interest in participating in the study.

11. The apparatus of claim 8, wherein the external circuitry is configured to identify the subsets of securely pooled user data to output to the other external circuitry based on analysis parameters provided by a requester and security parameters,
wherein the analysis parameters include parameters selected from the group consisting of:
types of physiological data, demographic of users, and a combination thereof; and
the security parameters include restrictions on combinations of data or specific data.

12. The apparatus of claim 11, wherein the security parameters include a threshold sensitivity value of user data that a requester is restricted from accessing, wherein the threshold sensitivity value is a function of the security of the requester.

13. The apparatus of claim 8, wherein the external circuitry is configured to identify the subsets of securely pooled user data to output to the external circuitry based on analysis parameters provided by a requester and security parameters, and identify a potential bias in the subsets of securely pooled user data output to the external circuitry and/or adjust the output securely pooled user data to correct for the bias.

14. The apparatus of claim 8, wherein at least one of the different services includes providing the user with access to a social group of users with an identified correlation.

15. The apparatus of claim 1, wherein the processing circuitry is configured and arranged to activate the subscription level of the different weighted values by providing a prompt to the user, and in response to the user selecting the prompt, which provides the respective weighted value, activating the subscription level.

16. The apparatus of claim 1, wherein the processing circuitry is configured and arranged to activate the service includes providing a prompt to the user indicative of participating in a clinical study, in response to the user selecting the prompt.

* * * * *